United States Patent [19]
Malfroy-Camine et al.

[11] Patent Number: 6,046,188
[45] Date of Patent: Apr. 4, 2000

[54] SYNTHETIC CATALYTIC FREE RADICAL SCAVENGERS USEFUL AS ANTIOXIDANTS FOR PREVENTION AND THERAPY OF DISEASE

[75] Inventors: Bernard Malfroy-Camine, Arlington; Susan Robin Doctrow, Roslindale, both of Mass.

[73] Assignee: Eukarion, Inc., Bedford, Mass.

[21] Appl. No.: 08/973,577

[22] PCT Filed: Jun. 6, 1996

[86] PCT No.: PCT/US96/10037

§ 371 Date: Mar. 11, 1998

§ 102(e) Date: Mar. 11, 1998

[87] PCT Pub. No.: WO96/40148

PCT Pub. Date: Dec. 19, 1996

Related U.S. Application Data

[63] Continuation-in-part of application No. 08/485,489, Jun. 7, 1995, Pat. No. 5,696,109.

[51] Int. Cl.⁷ .................................................. A61K 31/555
[52] U.S. Cl. ......................... 514/185; 514/184; 514/492; 514/501; 514/502; 514/505

[58] Field of Search ...................... 514/185, 184, 514/492, 501, 502, 505

[56] References Cited

U.S. PATENT DOCUMENTS

| | | | |
|---|---|---|---|
| 5,106,841 | 4/1992 | Scheer | 514/185 |
| 5,223,538 | 6/1993 | Fridovich et al. | 514/616 |
| 5,403,834 | 4/1995 | Malfroy-Camine et al. | 514/185 |
| 5,696,109 | 12/1997 | Malfroy-Camine et al. | 514/185 |

*Primary Examiner*—James H. Reamer
*Attorney, Agent, or Firm*—Townsend & Townsend & Crew LLP

[57] ABSTRACT

The invention provides antioxidant salen-metal complexes, compositions of such antioxidant salen-metal complexes having superoxide activity, catalase activity, and/or peroxidase activity, compositions of salen-metal complexes in a form suitable for pharmaceutical administration to treat or prevent a disease associated with cell or tissue damage produced by free radicals such as superoxide, and cosmetic and free radical quenching formulations of salen metal compounds.

24 Claims, 16 Drawing Sheets

|     | R₁  | R₂  | R₃  | R₄  | X   |
| --- | --- | --- | --- | --- | --- |
| C7  | H   | H   | H   | H   | Cl  |
| C31 | H   | H   | H   | H   | OAc |
| C36 | F   | H   | H   | H   | OAc |
| C37 | F   | H   | H   | H   | Cl  |
| C41 | H   | H   | OMe | H   | Cl  |
| C38 | H   | H   | OMe | H   | OAc |
| C32 | OMe | H   | H   | H   | OAc |
| C40 | OMe | H   | H   | H   | Cl  |
| C35 | H   | OMe | H   | OMe | OAc |
| C39 | H   | OMe | H   | OMe | Cl  |
| C33 | H   | OMe | H   | H   | OAc |
| C34 | H   | OMe | H   | H   | Cl  |

C42

C43

C44

C45

C46

C47

C48

C49

C50

C51

C52

| COMPOUND | CATALASE RATE | CATALASE ENDPOINT | PEROXIDASE RATE | SOD ACTIVITY |
|---|---|---|---|---|
| C7/C31 | 1.0 | 1.0 | 1.0 | 1.0 |
| C32 | 1.9 | 3.2 | 1.6 | 0.9 |
| C42 | 2.1 | 3.0 | 1.7 | 1.3 |
| C43 | 4.6 | 5.7 | 0.8 | 1.4 |
| C44 | 4.3 | 7.7 | 0.4 | ND |
| C45 | 5.7 | 10.4 | 0.2 | ND |
| C46 | 7.4 | 12.9 | 0.2 | ND |
| C47 | 3.3 | 4.8 | 0.9 | ND |
| C48 | 5.4 | 9.8 | 0.8 | ND |
| C49 | 1.5 | 4.4 | 1.6 | ND |
| C50 | 1.4 | 2.3 | 1.5 | ND |
| C51 | 0.4 | 0.4 | 0 | ND |
| C52 | 0.6 | 0.3 | 0 | ND |

SYNTHETIC CATALYTIC FREE RADICAL SCAVENGERS USEFUL AS ANTIOXIDANTS FOR PREVENTION AND THERAPY OF DISEASE

This is a CIP of Ser. No. 08/485,489, filed Jun. 7, 1995, U.S. Pat. No. 5,696,109.

FIELD OF THE INVENTION

The invention provides antioxidant compositions, including pharmaceutical compositions, of synthetic catalytic small molecule antioxidants and free radical scavengers for therapy and prophylaxis of disease and prevention of oxyradical-mediated oxidation, methods for using the small molecule antioxidants in prevention and treatment of pathological conditions, methods for using the small molecule antioxidants as preservatives and oxyradical quenching agents in hydrocarbons, methods for using the small molecule antioxidants for targeted protection of tissues and/or cell types during cancer chemotherapy, and methods for using the small molecule antioxidants to prevent toxicologic damage to individuals exposed to irritating oxidants or other sources of oxidative damage, particularly oxygen-derived oxidative species such as superoxide radical. The compositions and methods of the invention are also used for preventing oxidative damage in human transplant organs and for inhibiting reoxygenation injury following reperfusion of ischemic tissues. The compositions and methods of the invention are also useful for chemoprevention of chemical carcinogenesis and alteration of drug metabolism involving epoxide or free oxygen radical intermediates.

BACKGROUND OF THE INVENTION

Molecular oxygen is an essential nutrient for nonfacultative aerobic organisms, including, of course, humans. Oxygen is used in many important ways, namely, as the terminal electronic acceptor in oxidative phosphorylation, in many dioxygenase reactions, including the synthesis of prostaglandins and of vitamin A from carotenoids, in a host of hydroxylase reactions, including the formation and modification of steroid hormones, and in both the activation and the inactivation of xenobiotics, including carcinogens. The extensive P-450 system uses molecular oxygen in a host of important cellular reactions. In a similar vein, nature employs free radicals in a large variety of enzymic reactions.

Excessive concentrations of various forms of oxygen and of free radicals can have serious adverse effects on living systems, including the peroxidation of membrane lipids, the hydroxylation of nucleic acid bases, and the oxidation of sulfhydryl groups and of other sensitive moieties in proteins. If uncontrolled, mutations and cellular death result.

Biological antioxidants include well-defined enzymes, such as superoxide dismutase, catalase, selenium glutathione peroxidase, and phospholipid hydroperoxide glutathione peroxidase. Nonenzymatic biological antioxidants include tocopherols and tocotrienols, carotenoids, quinones, bilirubin, ascorbic acid, uric acid, and metal-binding proteins. various antioxidants, being both lipid and water soluble, are found in all parts of cells and tissues, although each specific antioxidant often shows a characteristic distribution pattern. The so-called ovothiols, which are mercaptohistidine derivatives, also decompose peroxides nonenzymatically.

Free radicals, particularly free radicals derived from molecular oxygen, are believed to play a fundamental role in a wide variety of biological phenomena. In fact, it has been suggested that much of what is considered critical illness may involve oxygen radical ("oxyradical") pathophysiology (Zimmermen J J (1991) Chest 100: 189S). Oxyradical injury has been implicated in the pathogenesis of pulmonary oxygen toxicity, adult respiratory distress syndrome (ARDS), bronchopulmonary dysplasia, sepsis syndrome, and a variety of ischemia-reperfusion syndromes, including myocardial infarction, stroke, cardiopulmonary bypass, organ transplantation, necrotizing enterocolitis, acute renal tubular necrosis, and other disease. Oxyradical can react with proteins, nucleic acids, lipids, and other biological macromolecules producing damage to cells and tissues, particularly in the critically ill patient.

Free radicals are atoms, ions, or molecules that contain an unpaired electron (Pryor, W A (1976) Free Radicals in Biol. 1: 1). Free radicals are usually unstable and exhibit short half-lives. Elemental oxygen is highly electronegative and readily accepts single electron transfers from cytochromes and other reduced cellular components; a portion of the $O_2$ consumed by cells engaged in aerobic respiration is univalently reduced to superoxide radical ($.O_2^-$) (Cadenas E (1989) Ann. Rev. Biochem. 58: 79). Sequential univalent reduction of $.O_2^-$ produces hydrogen peroxide ($H_2O_2$), hydroxyl radical (.OH), and water.

Free radicals can originate from many sources, including aerobic respiration, cytochrome P-450-catalyzed monooxygenation reactions of drugs and xenobiotics (e.g., trichloromethyl radicals, $CCl_3.$, formed from oxidation of carbon tetrachloride), and ionizing radiation. For example, when tissues are exposed to gamma radiation, most of the energy deposited in the cells is absorbed by water and results in scission of the oxygen-hydrogen covalent bonds in water, leaving a single electron on hydrogen and one on oxygen creating two radicals H. and .OH. The hydroxyl radical, .OH, is the most reactive radical known in chemistry. It reacts with biomolecules and sets off chain reactions and can interact with the purine or pyrimidine bases of nucleic acids. Indeed, radiation-induced carcinogenesis may be initiated by free radical damage (Breimer L H (1988) Brit. J. Cancer 57: 6). Also for example, the "oxidative burst" of activated neutrophils produces abundant superoxide radical, which is believed to be an essential factor in producing the cytotoxic effect of activated neutrophils. Reperfusion of ischemic tissues also produces large concentrations of Oxyradical, typically superoxide (Gutteridge J M C and Halliwell B (1990) Arch. Biochem. Biophys. 283: 223). Moreover, superoxide may be produced physiologically by endothelial cells for reaction with nitric oxide, a physiological regulator, forming peroxynitrite, $ONOO^-$ which may decay and give rise to hydroxyl radical, .OH (Marletta M A (1989) Trends Biochem. Sci. 14: 488; Moncada et al. (1989) Biochem. Pharmacol. 38: 1709; Saran et al. (1990) Free Rad. Res. Commun. 10: 221; Beckman et al. (1990) Proc. Natl. Acad. Sci. (U.S.A.) 87: 1620). Additional sources of oxyradical are "leakage" of electrons from disrupted mitochondrial or endoplasmic reticular electron transport chains, prostaglandin synthesis, oxidation of catecholamines, and platelet activation.

Oxygen, though essential for aerobic metabolism, can be converted to poisonous metabolites, such as the superoxide anion and hydrogen peroxide, collectively known as reactive oxygen species (ROS). Increased ROS formation under pathological conditions is believed to cause cellular damage through the action of these highly reactive molecules on proteins, lipids, and DNA. During inflammation, ROS are generated by activated phagocytic leukocytes; for example, during the neutrophil "respiratory burst", superoxide anion is generated by the membrane-bound NADPH oxidase. ROS are also believed to accumulate when tissues are subjected to ischemia followed by reperfusion.

Many free radical reactions are highly damaging to cellular components; they crosslink proteins, mutagenize DNA, and peroxidize lipids. Once formed, free radicals can Interact to produce other free radicals and non-radical oxidants such as singlet oxygen ($^1O_2$) and peroxides. Degradation of some of the products of free radical reactions can also generate potentially damaging chemical species. For example, malondialdehyde is a reaction product of peroxidized lipids that reacts with virtually any amine-containing molecule. Oxygen free radicals also cause oxidative modification of proteins (Stadtman E R (1992) *Science* 257: 1220).

Aerobic cells generally contain a number of defenses against the deleterious effects of oxyradicals and their reaction products. Superoxide dismutases (SODs) catalyze the reaction:

$$2.O_2^- + 2H^+ \rightarrow O_2 + H_2O_2$$

which removes superoxide and forms hydrogen peroxide. $H_2O_2$ is not a radical, but it is toxic to cells; it is removed by the enzymatic activities of catalase and glutathione peroxidase (GSH-Px). Catalase catalyzes the reaction:

$$2H_2O_2 \rightarrow 2H_2O + O_2$$

and GSH-Px removes hydrogen peroxide by using it to oxidize reduced glutathione (GSH) into oxidized glutathione (GSSG) according to the following reaction:

$$2GSH + H_2O_2 \rightarrow GSSG + 2H_2O$$

Other enzymes, such as phospholipid hydroperoxide glutathione peroxidase (PLOOH-GSH-Px), converts reactive phospholipid hydroperoxides, free fatty acid hydroperoxides, and cholesterol hydroperoxides to corresponding harmless fatty acid alcohols. Glutathione S-transferases also participate in detoxifying organic peroxides. In the absence of these enzymes and in presence of transition metals, such as iron or copper, superoxide and hydrogen peroxide can participate in the following reactions which generate the extremely reactive hydroxyl radical •OH⁻:

$$\cdot O_2^- + Fe^{3+} \rightarrow O_2 + Fe^{2+}$$

$$H_2O_2 + Fe^{2+} \rightarrow .OH + OH^- + Fe^{3+}$$

In addition to enzymatic detoxification of free radicals and oxidant species, a variety of low molecular weight antioxidants such as glutathione, ascorbate, tocopherol, ubiquinone, bilirubin, and uric acid serve as naturally-occurring physiological antioxidants (Krinsky N I (1992) *Proc. Soc. Exp. Biol. Med.* 200:248–54). Carotenoids are another class of small molecule antioxidants and have been implicated as protective agents against oxidative stress and chronic diseases. Canfield et al. (1992) *Proc. Soc. Exp. Biol. Med.* 200: 260 summarize reported relationships between carotenoids and various chronic diseases, including coronary heart disease, cataract, and cancer. Carotenoids dramatically reduce the incidence of certain premalignant conditions, such as leukoplakia, in some patients.

In an effort to prevent the damaging effects of oxyradical formation during reoxygenation of ischemic tissues, a variety of antioxidants have been used.

One strategy for preventing oxyradical-induced damage is to inhibit the formation of oxyradicals such as superoxide.

Iron ion chelators, such as desferrioxamine (also called deferoxamine or Desferol) and others, inhibit iron ion-dependent .OH generation and thus act as inhibitors of free radical formation (Gutteridge et al. (1979) *Biochem. J.* 184: 469; Halliwell B. (1989) *Free Radical Biol. Med.* 7: 645; Van der Kraaij et al. (1989) *Circulation* 80: 158). Amino-steroid-based antioxidants such as the 21-aminosteroids termed "lazaroids" (e.g., U74006F) have also been proposed as inhibitors of oxyradical formation. Desferrioxamine, allopurinol, and other pyrazolopyrimidines such as oxypurinol, have also been tested for preventing oxyradical formation in a myocardial stunning model system (Bolli et al. (1989) *Circ. Res.* 65: 607) and following hemorrhagic and endotoxic shock (DeGaravilla et al. (1992) *Drug Devel. Res.* 25: 139). However, each of these compounds has notable drawbacks for therapeutic usage. For example, deferoxamine is not an ideal iron chelator and its cellular penetration is quite limited.

Another strategy for preventing oxyradical-induced damage is to catalytically remove oxyradicals such as superoxide once they have been formed. Superoxide dismutase and catalase have been extensively explored, with some success, as protective agents when added to reperfusates in many types of experiments or when added pre-ischemia (reviewed in Gutteridge J M C and Halliwell B (1990) op. cit.). The availability of recombinant superoxide dismutase has allowed more extensive evaluation of the effect of administering SOD in the treatment or prevention of various medical conditions including reperfusion injury of the brain and spinal cord (Uyama et al. (1990) *Free Radic. Biol. Med.* 8: 265; Lim et al. (1986) *Ann. Thorac. Surg.* 42: 282), endotoxemia (Schneider et al. (1990) *Circ. Shock* 30: 97; Schneider et al. (1989) *Prog. Clin. Biol. Res.* 308: 913, and myocardial infarction (Patel et al. (1990) *Am. J. Physiol.* 258: H369; Mehta et al. (1989) *Am. J. Physiol.* 257: H1240; Nejima et al. (1989) *Circulation* 79: 143; Fincke et al. (1988) *Arzneimittelforschung* 38: 138; Ambrosio et al. (1987) *Circulation* 75: 282), and for osteoarthritis and intestinal ischemia (Vohra et al. (1989) *J. Pediatr. Surg.* 24: 893; Flohe L (1988) *Mol. Cell. Biochem.* 84: 123). Superoxide dismutase also has been reported to have positive effects in treating systemic lupus erythematosus, Crohn's disease, gastric ulcers, oxygen toxicity, burned patients, renal failure attendant to transplantation, and herpes simplex infection.

An alternative strategy for preventing oxyradical-induced damage is to scavenge oxyradicals such as superoxide once these have been formed, typically by employing small molecule scavengers which act stoichiometrically rather than catalytically. Congeners of glutathione have been used in various animal models to attenuate oxyradical injury. For example, N-2-mercaptopropionylglycine has been found to confer protective effects in a canine model of myocardial ischemia and reperfusion (Mitsos et al. (1986) *Circulation* 73: 1077) and N-acetylcysteine ("Mucomyst") has been used to treat endotoxin toxicity in sheep (Bernard et al. (1984) *J. Clin. Invest.* 73: 1772). Dimethyl thiourea (DMTU) and butyl-α-phenylnitrone (BPN) are believed to scavenge the hydroxyl radical, .OH, and has been shown to reduce ischemia-reperfusion injury in rat myocardium and in rabbits (Vander Heide et al. (1987) *J. Mol. Cell. Cardiol.* 19: 615; Kennedy et al. (1987) *J. Appl. Physiol.* 63: 2426). Mannitol has also been used as a free radical scavenger to reduce organ injury during reoxygenation (Fox RB (1984) *J. Clin. Invest.* 74: 1456; Ouriel et al. (1985) *Circulation* 72: 254). In one report, a small molecule chelate was reported to have activity as a glutathione peroxidase mimic (Spector et al. (1993) *Proc. Natl. Acad. Sci. (U.S.A.)* 90: 7485).

Thus, application of inhibitors of oxyradical formation and/or enzymes that remove superoxide and hydrogen peroxide and/or small molecule oxyradical scavengers have all shown promise for preventing reoxygenation damage present in a variety of ischemic pathological states and for treating or preventing various disease states associated with free radicals. However, each of these categories contains several drawbacks. For example, inhibitors of oxyradical formation typically chelate transition metals which are used in essential enzymatic processes in normal physiology and respiration; moreover, even at very high doses, these inhibitors do not completely prevent oxyradical formation. Superoxide dismutases and catalase are large polypeptides which are expensive to manufacture, do not penetrate cells or the blood-brain barrier, and generally require parenteral routes of administration. Free radical scavengers act stoichiometrically and are thus easily depleted and must be administered in high dosages to be effective.

The complex formed between the chelator desferroxamine and manganese has SOD activity and has shown some activity in biological models but the instability of the metal ligand complex apparently precludes its pharmaceutical use. Porphyrin-manganese complexes have been shown to protect bacteria from paraquat toxicity and to promote the aerobic survival of SOD-deficient *E. coli* mutants. A class of manganese macrocyclic ligand complexes with SOD activity has also been recently described with one prototype reportedly showing protection in a model for myocardial ischemia-reperfusion injury (Black et al. (1994) *J. Pharmacol. Exp. Ther.* 270: 1208).

Based on the foregoing, it is clear that a need exists for antioxidant agents which are efficient at removing dangerous oxyradicals, particularly superoxide and hydrogen peroxide, and which are inexpensive to manufacture, stable, and possess advantageous pharmacokinetic properties, such as the ability to cross the blood-brain barrier and penetrate tissues. Such versatile antioxidants would find use as pharmaceuticals, chemoprotectants, and possibly as dietary supplements. It is one object of the invention to provide a class of novel antioxidants which possess advantageous pharmacologic properties and which catalytically and/or stoichiometrically remove superoxide and/or hydrogen peroxide.

It is another object of the invention to provide antioxidant compositions and methods for inhibiting undesirable polymerization, oxidation, and/or gum formation in hydrocarbons, including plastics, nitrile rubbers, chloroprene rubbers, silicone rubber, isoprene rubbers, other rubber analogs, oils and waxes, cosmetic bases, animal fats, petroleum and petrochemicals and distillates, polymerizable resins, dyes, photosensitive agents, flavor agents, adhesives, sealants, polymer precursors, and the like. Also encompassed in the invention are salen-metal antioxidants and methods for inhibiting oxyradical-mediated polymerization and/or oxyradical-mediated decomposition. The polymers are usually formed by reactions of unsaturated hydrocarbons, although any hydrocarbon can polymerize. Generally, olefins tend to polymerize more readily than aromatics, which in turn polymerize more readily than paraffins. Trace organic materials containing hetero atoms such as nitrogen, oxygen and sulfur also contribute to polymerization, as does molecular oxygen, oxyradicals (e.g., superoxide, peroxides, hydroxyl radical), and other free radicals. Polymers are generally formed by free radical chain reactions. These reactions, typically consist of two phases, an initiation phase and a propagation phase. Free radicals, which have an odd (unpaired) electron, can act as chain carriers and/or initiators. During chain propagation, additional free radicals are formed and the hydrocarbon molecules grow larger and larger, sometimes forming unwanted polymers which accumulate. Research indicates that even very small amounts of oxygen can cause or accelerate polymerization. Accordingly, antioxidant antifoulants have been developed to prevent oxygen from initiating polymerization, such as in petroleum refining apparatus. Antioxidants act as chain-stoppers by forming inert molecules with the oxidized free radical hydrocarbons. U.S. Pat. No. 4,466,905, Butler et al., teaches a polymer inhibiting composition and process for inhibiting the polymerization of vinyl aromatic compounds. U.S. Pat. No. 3,907,745, Bsharah et al., teaches a synergistic antioxidant system for use in polymer system susceptible to oxidation. This system comprises a combination of an antioxidant such as a phenylenediamine and a chelating agent or metal deactivator such as a polyamine. U.S. Pat. No. 4,720,566 Martin, teaches compositions and methods for inhibiting acrylonitrile polymerization in quench columns of acrylonitrile producing systems. U.S. Pat. No. 4,929,778, Roling, teaches compositions and methods for inhibiting the polymerization of vinyl aromatic monomers during the preparation of monomers and the storage and shipment of products containing such monomers. New antioxidants and antioxidant methods are needed in the art, particularly for use in aqueous or mixed aqueous/organic systems. The present invention fulfills these and other needs.

The references discussed herein are provided solely for their disclosure prior to the filing date of the present application. Nothing herein is to be construed as an admission that the inventors are not entitled to antedate such disclosure by virtue of prior invention. All publications cited are incorporated herein by reference.

SUMMARY OF THE INVENTION

In accordance with the foregoing objects, in one aspect of the invention pharmaceutical compositions are provided which have potent antioxidant and/or free radical scavenging properties and function as in vivo antioxidants. The pharmaceutical compositions of the invention comprise an efficacious dosage of at least one species of salen-transition metal complex, typically a salen-manganese complex such as a salen-Mn(III) complex. In one embodiment, the pharmaceutical composition comprises a salen-Mn complex which is a chelate of Mn(III) with a diamine derivative, such as ethylenediamine linked to two substituted salicylaldehydes. These pharmaceutical compositions possess the activity of dismutating superoxide (i.e., superoxide dismutase activity) and, advantageously, also converting hydrogen peroxide to water (i.e., catalase activity). The pharmaceutical compositions are effective at reducing pathological damage related to formation of oxyradicals such as superoxide and peroxides and other free radical species.

The invention also provides methods for treating and preventing pathological conditions by applying or administering compositions of salen-transition metal complexes in a therapeutic or prophylactic dosage. Salen-transition metal complexes used in the methods of the invention are typically salen-manganese complexes, such as Mn(III)-salen complexes. The invention provides methods for preventing or reducing ischemic/reperfusion damage to critical tissues such as the myocardium and central nervous system. The invention also provides methods for preventing or reducing cellular damage resulting from exposure to various chemical compounds which produce potentially damaging free radical species, comprising administering a therapeutically or prophylactically efficacious dosage of at least one species of salen-transition metal complex, preferably a salen-manganese complex having detectable SOD activity and preferably also having detectable catalase activity. The antioxidant salen-transition metal complexes of the invention are administered by a variety of routes, including parenterally, topically, and orally.

In one aspect of the invention, a therapeutic or prophylactic dosage of a salen-transition metal complex of the present invention is administered alone or combined with (1) one or more antioxidant enzymes, such as a Mn-SOD, a Cu,Zn-SOD, or catalase, and/or (2) one or more free radical scavengers, such as tocopherol, ascorbate, glutathione, DMTU, N-acetylcysteine, or N-2-mercaptopropionylglycine and/or (3) one or more oxyradical inhibitors, such as desferrioxamine or allopurinol, and/or one or more biological modifier agents, such as calpain inhibitors. The formulations of these compositions is dependent upon the specific pathological condition sought to be treated or prevented, the route and form of administration, and the age, sex, and condition of the patient. These compositions are administered for various indications, including: (1) for preventing ischemic/reoxygenation injury in a patient, (2) for preserving organs for transplant in an anoxic, hypoxic, or hyperoxic state prior to transplant, (3) for protecting normal tissues from free radical-induced damage consequent to exposure to ionizing radiation and/or chemotherapy, as with bleomycin, (4) for protecting cells and tissues from free radical-induced injury consequent to exposure to xenobiotic compounds which form free radicals, either directly or as a consequence of monooxygenation through the cytochrome P-450 system, (5) for enhancing cryopreservation of cells, tissues, organs, and organisms by increasing viability of recovered specimens, and (6) for prophylactic administration to prevent: carcinogenesis, cellular senescence, cataract formation, formation of malondialdehyde adducts, HIV pathology and macromolecular crosslinking, such as collagen crosslinking.

In one aspect of the invention, salen-transition metal complexes are formulated for administration by the oral route by forming a pharmaceutical dosage form comprising an excipient and not less than 1 μg nor more than about 10 grams of at least one antioxidant salen-transition metal complex of the invention. Dietary formulations are administered for therapy of free radical-induced diseases and/or for the chemoprevention of neoplasia and/or oxidative damage associated with normal aerobic metabolism.

In another aspect of the invention, buffered aqueous solutions comprising at least one antioxidant salen-transition metal complex of the invention at a concentration of at least 1 nM but not more than about 100 mM is formulated for administration, usually at a concentration of about 0.1 to 10 mM, typically by intravenous route, to a patient undergoing or expected to undergo: (1) an ischemic episode, such as a myocardial infarction, cerebral ischemic event, transplantation operation, open heart surgery, elective angioplasty, coronary artery bypass surgery, brain surgery, renal infarction, traumatic hemorrhage, tourniquet application, (2) antineoplastic or antihelminthic chemotherapy employing a chemotherapeutic agent which generates free radicals, (3) endotoxic shock or sepsis, (4) exposure to ionizing radiation, (5) exposure to exogenous chemical compounds which are free radicals or produce free radicals, (6) thermal or chemical burns or ulcerations, (7) hyperbaric oxygen, or (8) apoptosis of a predetermined cell population (e.g., lymphocyte apoptosis). The buffered aqueous solutions of the invention may also be used, typically in conjunction with other established methods, for organ culture, cell culture, transplant organ maintenance, and myocardial irrigation. Nonaqueous formulations, such as lipid-based formulations are also provided, including stabilized emulsions. The antioxidant salen-metal compositions are administered by various routes, including intravenous injection, intramuscular injection, subdermal injection, intrapericardial injection, surgical irrigation, topical application, ophthalmologic application, lavage, gavage, enema, intraperitoneal infusion, mist inhalation, oral rinse, and other routes, depending upon the specific medical or veterinary use intended.

In another aspect of the invention, antioxidant salen-transition metal complexes of the invention are employed to modulate the expression of naturally-occurring genes or other polynucleotide sequences under the transcriptional control of an oxidative stress response element (e.g., an antioxidant responsive element, ARE), such as an antioxidant response element of a glutathione S-transferase gene or a NAD(P)H:quinone reductase gene. The antioxidant salen-metal complexes may be used to modulate the transcription of ARE- regulated polynucleotide sequences in cell cultures (e.g., ES cells) and in intact animals, particularly in transgenic animals wherein a transgene comprises one or more AREs as transcriptional regulatory sequences.

The present invention also encompasses pharmaceutical compositions of antioxidant salen-manganese complexes, therapeutic uses of such antioxidant salen-manganese complexes, methods and compositions for using antioxidant salen-manganese complexes in diagnostic, therapeutic, and research applications in human and veterinary medicine.

The invention also provides methods for preventing food spoilage and oxidation by applying to foodstuffs an effective amount of at least one antioxidant salen-metal complex species. The invention also provides compositions for preventing food spoilage comprising an effective amount of at least one species of antioxidant salen-metal complex, optionally in combination with at least one additional food preservative agent (e.g., butylated hydroxytoluene, butylated hydroxyanisole, sulfates, sodium nitrite, sodium nitrate). For example, an antioxidant salen-metal complex is incorporated into a foodstuff subject to rancidification (e.g., oxidation) to reduce the rate of oxidative decomposition of the foodstuff when exposed to molecular oxygen.

In an aspect, the invention relates to antioxidant compositions and methods of use in inhibiting formation of undesired hydrocarbon polymers generated via free radical-mediated polymerization mechanisms, especially oxyradical-mediated polymerization and/or oxyradical-mediated rancidification or gum formation. The antioxidant salen-metal complexes of the invention can be applied to a variety of hybdrocarbons to reduce undesired oxidation and/or polymerization, or to quench a polymerization reaction at a desired state of polymer formation (e.g., at a desired average chain length). For example and not to limit the invention, examples of such saturated and unsaturated hydrocarbons include: petroleum distillates and petrochemicals, turpentine, paint, synthetic and natural rubber, vegetable oils and waxes, animal fats, polymerizable resins, polyolefin, and the like.

The invention relates to antioxidant compositions and methods of use in hydrocarbon compositions to reduce and/or control the formation of undesired polymers which comtaminate such hydrocarbon compositions, including hydrocarbons present in aqueous systems, two-phase aqueous:organic systems, and organic solvent systems. This invention relates to a method and composition for controlling the formation of polymers in such systems which comprises an antioxidant composition comprising an antioxidant salen-metal compound, optionally in combination with an antioxidant or stabilizer other than a salen-metal compound (e.g., BHT, BHA, catechol, tocopherol, hydroquinone, etc.). More particularly, this invention relates to a method and composition for controlling the formation of polymers which comprises an antioxidant composition comprising an antioxidant salen-metal complex. The amount of the individual ingredients of the antioxidant composition will vary depending upon the severity of the undesirable polymer formation encountered due to free radical polymerization as well as the activity of the salen-metal compound utilized.

In other embodiments the invention provides methods for enhancing the recovery of skin of a warm-blooded animal from wounds, such as surgical incisions, burns, inflammation or minor irritation due to oxidative damage, etc. The methods comprise administering to the skin wound or irritation a therapeutically or, in some cases a prophylactically effective amount of a composition which comprises an antioxidant salen-metal complex.

The present invention also provides compounds having glutathione peroxidase activity and, therefore, capable of serving as effective glutathione peroxidase replacements. These compounds are useful as drugs for the prevention of many pathological conditions, including but not limited to neoplasia, apoptosis of somatic cells, skin aging, cataracts, and the like; and as anti-oxidants for scavenging $H_2O_2$ and other peroxides. The present invention also provides methods and pharmaceutical compositions of these compounds.

The present invention also concerns a method of reducing $H_2O_2$ and/or other peroxides which comprises contacting $H_2O_2$ and/or other peroxides with a suitable amount of any of the compounds of the invention effective to reduce $H_2O_2$ and/or other peroxides. Additionally, the invention provides a method of treating a peroxide-induced condition in a subject which comprises administering to the subject an amount of any of the compounds of the invention effective to reduce peroxide in a subject and thereby treat the peroxide-induced condition. Further, the invention provides a pharmaceutical composition which comprises an amount of any of the compounds of the invention effective to reduce peroxide in a subject with a peroxide-induced condition and a pharmaceutically acceptable carrier. Further, the invention provides a method of treating a peroxide-induced condition in a subject, e.g. a human subject, which comprises administering, e.g. by topical, oral, intravenous, intraperitoneal, intramuscular, intradermal, or subcutaneous administration, to the subject an amount of an antioxidant salen-metal compound effective to reduce peroxide in the subject and thereby treat the peroxide-induced condition. It is worthy to point out at this time that the administration of the compound to the subject may be effected by means other than those listed herein. Further, the peroxide-induced condition may involve cataracts, inflammation of a tissue, ischemia, an allergic reaction, or pathology caused by oxidative stress. Where the peroxide-induced condition involves cataracts, administration is effected by, but is not limited to, topical contact to the surface of an eye.

All publications and patent applications herein are incorporated by reference to the same extent as if each individual publication or patent application was specifically and individually indicated to be incorporated by reference.

BRIEF DESCRIPTION OF THE DRAWINGS

FIG. 13A: NBT reduction in the presence of (solid circle), 0; (open circle), 0.1 $\mu$M; (solid triangle), 0.5 $\mu$M; (open triangle), 1.5 $\mu$M; (solid square), 3 $\mu$M; and (open square), 6 $\mu$M C7. FIG. 13B: xanthine oxidase activity, detected by the formation of urate in the presence of (solid circle), 0; (open circle), 6 $\mu$M; and (solid triangle), 11 $\mu$M C7.

FIG. 15A: pH 8.1, $H_2O_2$ concentration of: (solid circle), 0.1 mM; (open circle), 1 mM; (solid triangle), 10. mM; FIG. 15B: 10 mM $H_2O_2$, pH was: (solid circle), 6.0; (open circle) 7.1; (solid triangle), 8.1.

FIG. 16A: Time-dependent changes in levels of C7 (solid circle), salicylaldehyde (X), and an unidentified substance (open triangles) in incubation mixtures lacking ABTS. FIG. 16B. The percent of initial C7 remaining in incubations conducted in the absence (solid circle) and presence (open circle) of 1 mM ABTS.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, an "antioxidant" is a substance that, when present in a mixture or structure containing an oxidizable substrate biological molecule, significantly delays or prevents oxidation of the substrate biological molecule. Antioxidants can act by scavenging biologically important reactive free radicals or other reactive oxygen species ($.O_2^-$, $H_2O_2$, .OH, HOCl, ferryl, peroxyl, peroxynitrite, and alkoxyl), or by preventing their formation, or by catalytically converting the free radical or other reactive oxygen species to a less reactive species. An antioxidant salen-transition metal complex of the invention generally has detectable SOD activity. A salen-transition metal complex of the invention has antioxidant activity if the complex, when added to a cell culture or assay reaction, produces a detectable decrease in the amount of a free radical, such as superoxide, or a nonradical reactive oxygen species, such as hydrogen peroxide, as compared to a parallel cell culture or assay reaction that is not treated with the complex. Suitable concentrations (i.e., efficacious dose) can be determined by various methods, including generating an empirical dose-response curve, predicting potency and efficacy of a congener by using QSAR methods or molecular modeling, and other methods used in the pharmaceutical sciences. Since oxidative damage is generally cumulative, there is no minimum threshold level (or dose) with respect to efficacy, although minimum doses for producing a detectable therapeutic or prophylactic effect for particular disease states can be established. Antioxidant salen metal complexes of the invention may have glutathione peroxidase activity.

Figure 3:
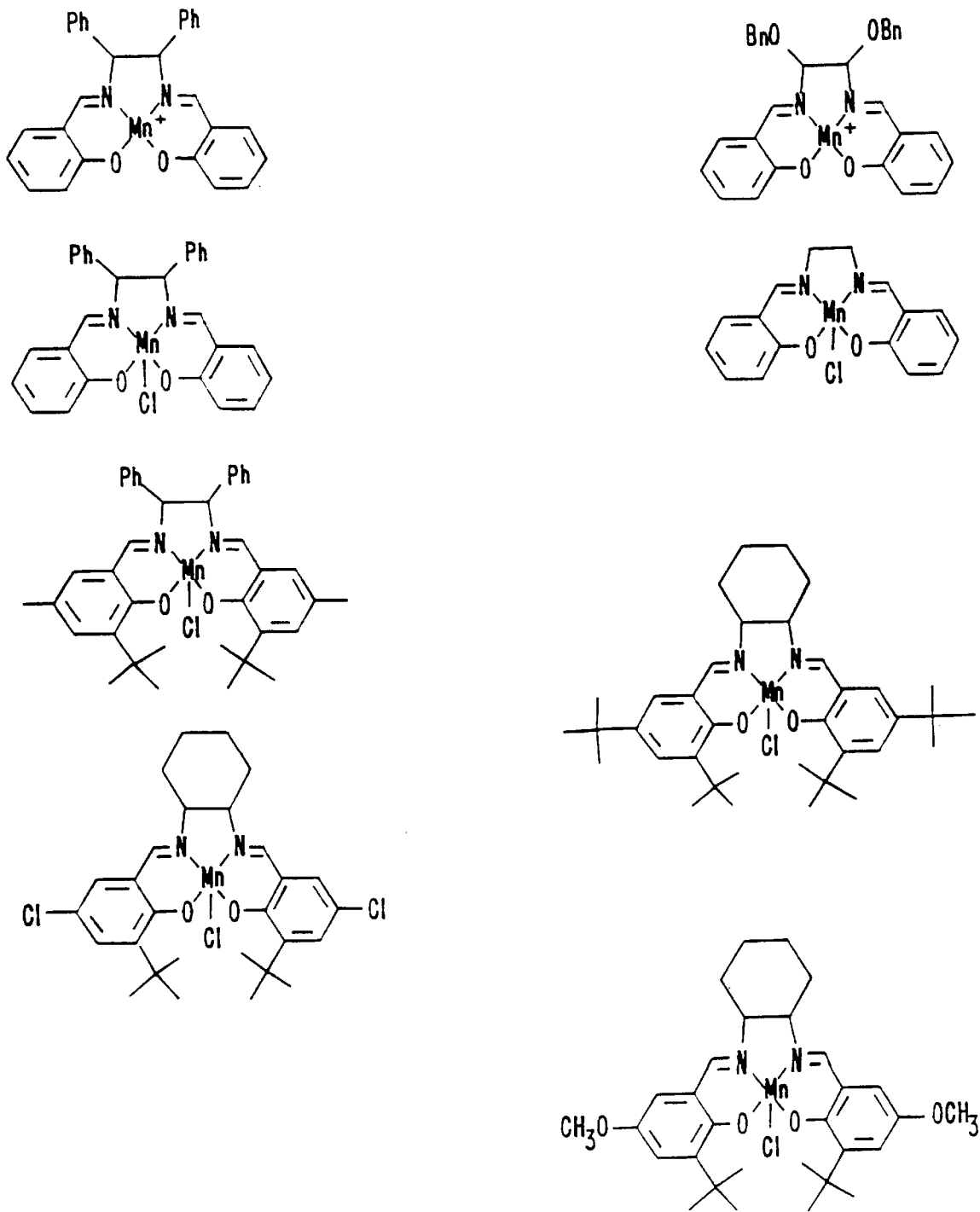
FIG. 3 shows structures of preferred compounds of the invention.
Figure 12:
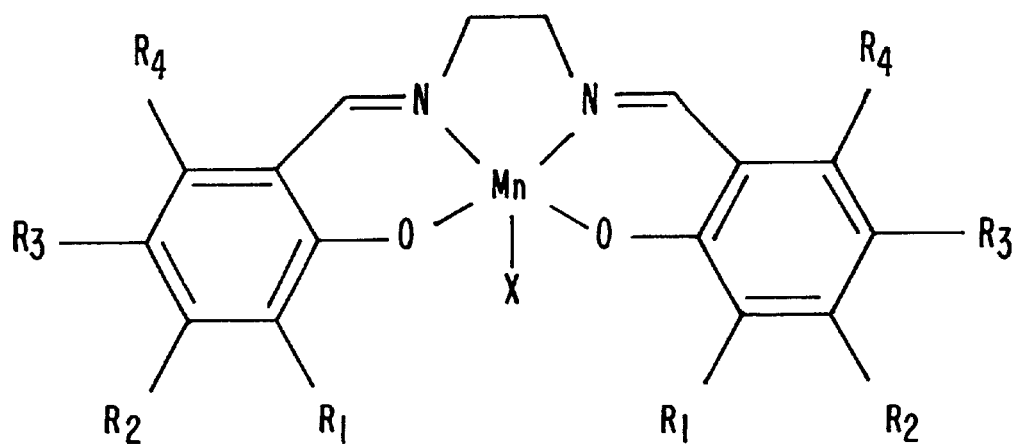
FIG. 12 shows examples of structures of antioxidant salen-metal complexes.

As used herein, a "salen-transition metal complex" refers to a compound having a structure according to Structure I, Structure II, Structure III, or Structure IV, Structure V, Structure VI, Structure VII, Structure VIII, Structure IX (see, infra) or any of the structures C1, C4, C6, C7, C9, C10, C11, C12, C15, C17, C20, C22, C23, C25, C27, C28, C29, and C30 as shown in FIG. 3 or any of C31, C32, C33, C34, C35, C36, C37, C38, C39, C40, C41, C42, C43, C44, C45, C46, C47, C48, C49, C50, C51, and C52 as shown in FIG. 12 and FIG. 19 herein; preferably having a structure corresponding to one of the structures shown in FIG. 3, FIG. 12, or FIG. 19 selected from the group consisting of: C6, C7, C12, C31, C32, C33, C34, C35, C36, C37, C38, C39, C40, C41, C42, C43, C44, C45, C46, C47, C48, C49, C50, C51, and C52. The transition metal is typically selected from the group consisting of: Mn, Mg, Co, Fe, V, Cr, and Ni; and is most conveniently Mn or Mg, generally Mn.

As used herein, "free radical-associated disease" refers to a pathological condition of an individual that results at least in part from the production of or exposure to free radicals, particularly oxyradicals, and other reactive oxygen species in vivo. It is evident to those of skill in the art that most pathological conditions are multifactorial, in that multiple factors contributing to the disease state are present, and that assigning or identifying the predominant causal factor(s) for any individual pathological condition is frequently extremely difficult. For these reasons, the term "free radical associated disease" encompasses pathological states that are recognized in the art as being conditions wherein damage from free radicals or reactive oxygen species is believed to contribute to the pathology of the disease state, or wherein administration of a free radical inhibitor (e.g., desferrioxamine), scavenger (e.g., tocopherol, glutathione), or catalyst (e.g., SOD, catalase) is shown to produce a detectable benefit by decreasing symptoms, increasing survival, or providing other detectable clinical benefits in treating or preventing the pathological state. For example but not limitation, the disease states discussed herein are considered free radical-associated diseases (e.g., ischemic reperfusion injury, inflammatory diseases, systemic lupus erythematosis, myocardial infarction, stroke, traumatic hemorrhage, spinal cord trauma, Crohn's disease, autoimmune diseases (e.g., rheumatoid arthritis, diabetes), cataract formation, uveitis, emphysema, gastric ulcers, oxygen toxicity, neoplasia, undesired cell apoptosis, radiation sickness, and other pathological states discussed in the Background section and infra, such as toxemia and acute lung injury). Such diseases can include "apoptosis-related ROS" which refers to reactive oxygen species (e.g., $O_2^-$, HOOH) which damage critical cellular components (e.g., lipid peroxidation) in cells stimulated to undergo apoptosis, such apoptosis-related ROS may be formed in a cell in response to an apoptotic stimulus and/or produced by non-respiratory electron transport chains (i.e., other than ROS produced by oxidative phosphorylation)

The present invention provides methods for therapy and prophylaxis of free radical-associated disease comprising administering to a patient a therapeutically-effective dose of an antioxidant salen-metal complex pharmaceutical composition. In preferred embodiments, the method is used for preventing, arresting, or treating (1) neurological damage such as Parkinson's disease or anoxia injury, (2) cardiac tissue necrosis resulting from cardiac ischemia, (3) autoimmune neurodegeneration (e.g., encephalitis), (4) acute lung injury such as in sepsis and endotoxemia, and (5) neuronal damage resulting from anoxia (e.g., stroke, drowning, brain surgery) or trauma (e.g., concussion or cord shock).

As used herein the terms "SOD mimetic", "SOD mimic", "superoxide dismutase mimetic", and "superoxide catalyst" refer to compounds which have detectable catalytic activity for the dismutation of superoxide as determined by assay. Generally, an SOD mimetic possesses at least about 0.001 percent of the SOD activity of human Mn-SOD or Zn,Cu-SOD, on a molar basis, as determined by standard assay methods and/or has at least 0.01 unit of SOD activity per mM according to the SOD assay used hereinbelow, preferably at least 1 unit of SOD activity per mM.

The term "pharmaceutical agent or drug" as used herein refers to a chemical compound or composition capable of inducing a desired therapeutic effect when properly administered to a patient.

The term "alkyl" refers to a cyclic, branched, or straight chain alkyl group containing only carbon and hydrogen, and unless otherwise mentioned, contain one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "lower alkyl" refers to a cyclic, branched or straight chain monovalent alkyl radical of one to six carbon atoms. This term is further exemplified by such radicals as methyl, ethyl, n-propyl, i-propyl, n-butyl, t-butyl, i-butyl (or 2-methylpropyl), cyclopropylmethyl, i-amyl, n-amyl, and hexyl.

The term "aryl" or "Ar" refers to a monovalent unsaturated aromatic carbocyclic group having a single ring (e.g., phenyl) or multiple condensed rings (e.g., naphthyl or anthryl), which can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "substituted alkoxy" refers to a group having the structure —O—R, where R is alkyl which is substituted with a non-interfering substituent. The term "arylalkoxy" refers to a group having the structure —O—R—Ar, where R is alkyl and Ar is an aromatic substituent. Arylalkoxys are a subset of substituted alkoxys. Examples of preferred substituted alkoxy groups are: benzyloxy, napthyloxy, and chlorobenzyloxy.

The term "aryloxy" refers to a group having the structure —O—Ar, where Ar is an aromatic group. A preferred aryloxy group is phenoxy.

The term "heterocycle" refers to a monovalent saturated, unsaturated, or aromatic carbocyclic group having a single ring (e.g., morpholino, pyridyl or furyl) or multiple condensed rings (e.g., indolizinyl or benzo[b]thienyl) and having at least one heteroatom, defined as N, O, P, or S, within the ring, which can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality. The term "heteroaryl" or "HetAr" refers to an aromatic heterocycle.

"Arylalkyl" refers to the groups —R—Ar and —R-HetAr, where Ar is an aryl group, HetAr is a heteroaryl group, and R is straight-chain or branched-chain aliphatic group. Examples of arylalkyl groups include benzyl and furfuryl. Arylalkyl groups can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

As used herein, the term "halo" or "halide" refers to fluoro, bromo, chloro and iodo substituents.

As used in the structures that follow, the term "OBn" means benzyloxy.

As used herein, the term "amino" refers to a chemical functionality —NR'R", where R' and R" are independently hydrogen, alkyl, or aryl. The term "quaternary amine" refers to the positively charged group —N$^+$R'R"R"', where R', R", and R"' are independently selected and are alkyl or aryl. A preferred amino group is —NH$_2$.

The term "silyl" as used herein refers to organometallic substituents, wherein at least one silicon atom is linked to at least one carbon atom; an example of a silyl substituent is the trimethylsilyl substituent, (CH$_3$)$_3$Si—.

The term "pharmaceutical agent or drug" as used herein refers to a chemical compound or composition capable of inducing a desired therapeutic effect when properly administered to a patient.

Other chemistry terms herein are used according to conventional usage in the art, as exemplified by *The McGraw-Hill Dictionary of Chemical Terms* (ed. Parker, S., 1985), McGraw-Hill, San Francisco, incorporated herein by reference).

DETAILED DESCRIPTION

Generally, the nomenclature used hereafter and the laboratory procedures in cell culture, analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

A basis of the present invention is the unexpected finding that members of a class of compounds described originally as epoxidation catalysts, the so-called salen-transition metal complexes, also exhibit potent superoxide dismutase activity and/or catalase activity and function as catalysts for free radical removal both in vitro and in vivo. The salen-transition metal complexes have been described as chiral epoxidation catalysts for various synthetic chemistry applications (Fu et al. (1991) *J. Org. Chem.* 56: 6497; Zhang W and Jacobsen E N (1991) *J. Org. Chem.* 56: 2296; Jacobsen et al. (1991) *J. Am. Chem. Soc.* 113: 6703; Zhang et al. (1990) *J. Am. Chem. Soc.* 112: 2801; Lee N H and Jacobsen E N (1991) *Tetrahedron Lett.* 32: 6533; Jacobsen et al. (1991) *J. Am. Chem. Soc.* 113: 7063; Lee et al. (1991) *Tetrahedron Lett.* 32: 5055). However, salen-transition metal complexes are also useful as potent antioxidants for various biological applications, including their use as pharmaceuticals for prevention or treatment of free radical-associated diseases. Pharmaceutical formulations, dietary supplements, improved cell and organ culture media, improved cryopreservation media, topical ointments, and chemoprotective and radioprotective compositions can be prepared with an effective amount or concentration of at least one antioxidant salen-transition metal complex species.

The catalytic activity of salen-metal complexes to interconvert epoxides may also be used to advantage to scavenge or prevent formation in vivo of cytotoxic and/or carcinogenic epoxide species, such as may be formed by the cytochrome P-450 monooxygenation system (e.g., benzo-[a]-pyrene diol epoxide). Catalytic salen-metal complexes may be advantageously included into foodstuffs or dietary supplements (or administered in other forms) to individuals who are at risk of exposure to polycyclic hydrocarbon chemical carcinogens, such as workers in the petrochemical industry and dyestuff manufacture. Moreover, catalytically active salen-metal complexes may be formulated for administration to smokers (including passive smokers) to enhance detoxification of reactive epoxides formed from cigarette smoke.

The antioxidant salen metal complexes of the invention can find use to partially or totally arrest the progression of neurodegenerative diseases. For example, mutations in Cu/Zn superoxide dismutase have been reported to be strongly associated with amyotrophic lateral sclerosis (ALS) (Rosen et al. (1993) *Nature* 362: 59; Deng et al. (1993) *Science* 261: 1047). Similar defects in endogenous antioxudant protection may be reponsible for multiple sclerosis, peripheral neuropathies, and the like. Antioxidant salen metal complexes of the present invention can be used for treatment and prophylaxis of such neurodegenerative diseases (e.g., ALS, MS).

Salen-Transition Metal Complexes

In accordance with a first aspect of the invention, the salen-transition metal complex has the following structure:

Structure I

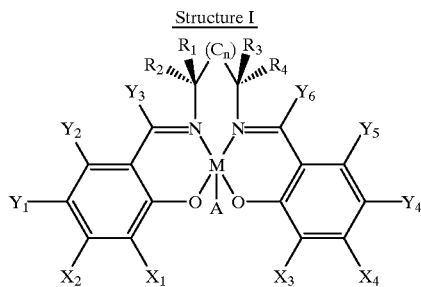

wherein M is a transition metal ion, preferably Mn; A is an anion, typically Cl; and n is either 0, 1, or 2. $X_1$, $X_2$, $X_3$ and $X_4$ are independently selected from the group consisting of hydrogen, silyls, aryls, arylalkyls, primary alkyls, secondary alkyls, tertiary alkyls, alkoxys, aryloxys, aminos, quaternary amines, heteroatoms, and hydrogen; typically $X_1$ and $X_3$ are from the same functional group, usually hydrogen, quaternary amine, or tertiary butyl, and $X_2$ and $X_4$ are typically hydrogen. $Y_1$, $Y_2$, $Y_3$, $Y_4$, $Y_5$, and $Y_6$ are independently selected from the group consisting of hydrogen, halides, alkyls, aryls, arylalkyls, silyl groups, aminos, alkyls or aryls bearing heteroatoms; aryloxys, alkoxys, and halide; preferably, $Y_1$ and $Y_4$ are alkoxy, halide, or amino groups. Typically, $Y_1$ and $Y_4$ are the same. $R_1$, $R_2$, $R_3$ and $R_4$ are independently selected from the group consisting of H, $CH_3$, $C_2H_5$, $C_6H_5$, O-benzyl, primary alkyls, fatty acid esters, substituted alkoxyaryls, heteroatom-bearing aromatic groups, arylalkyls, secondary alkyls, and tertiary alkyls.

According to one class of embodiments of the first aspect of the invention, at least one of the $X_1$ and $X_3$ sites, and preferably both $X_1$ and $X_3$ include a substituent selected from the group of blocking substituents consisting of secondary or tertiary alkyl groups, aryl groups, silyl groups, heterocycles, and alkyl groups bearing heteroatom substituents such as alkoxy or halide. Preferably, the $X_1$ and $X_3$ sites bear the same substituent, which substituent is most preferably a tertiary alkyl group, such as tertiary butyl. Preferably, when $X_1$ and $X_3$ bear a blocking substituent, then $X_2$ and $X_4$ are selected from a group of non-blocking substituents such as H, $CH_3$, $C_2H_5$, and primary alkyls, most preferably, H. Alternatively, either three or four of $X_1$, $X_2$, $X_3$, and $X_4$ can be selected from the group of blocking substituents.

According to this first aspect of the invention, typically at least one and generally no more than two of $R_1$, $R_2$, $R_3$ and $R_4$ are selected from a group consisting of H, $CH_3$, $C_2H_5$, and primary alkyls. For convenience, this group will be referred to as the non-blocking group. If $R_1$ is selected from the non-blocking group, then $R_2$ and $R_3$ are preferably selected from the blocking group, and typically $R_2$ and $R_3$ are identical and are phenyl or benzyloxy. If $R_2$ is selected from the non-blocking group, then $R_1$ and $R_4$ are preferably selected from the blocking group. Likewise, if $R_3$ is selected from the non-blocking group, then $R_1$ and $R_4$ are preferably selected from the blocking group. Finally, if $R_4$ is selected from the non-blocking group, then $R_2$ and $R_3$ are preferably selected from the blocking group. Phenyl and benzyloxy are particularly preferred blocking groups for substitution at any of $R_1$, $R_2$, $R_3$ and $R_4$. Typically, the blocking groups selected are identical. A preferred class of embodiments have $R_1$ and $R_4$ as benzyloxy or phenyl and $R_2$ and $R_3$ as hydrogen.

Stated in other terms, one class of embodiments of the first aspect of the invention requires that, of the four sites available for substitution on the two carbon atoms adjacent to nitrogen, at least one or two of these preferably will include a substituent from the non-blocking group.

Preferably, the non-blocking substituent is either hydrogen or methyl, but most preferably, hydrogen. Preferably, the blocking substituent is either a phenyl group, a benzyloxy, or a tertiary butyl group, more preferably a phenyl group or a benzyloxy group, most usually a phenyl group.

Preferably, $Y_3$ and $Y_6$ are hydrogen, methyl, alkyl, or aryl. More preferably, they are hydrogen or methyl. Most preferably, they are hydrogen.

The $Y_1$, $Y_2$, $Y_4$, and $Y_5$ sites are selected independently and are preferably occupied by hydrogen, although these sites may also be occupied by substituents independently selected from the group consisting of hydrogen, halides, alkyls, aryls, alkoxy groups, substituted alkoxy groups, nitro groups, and amino groups. $Y_1$ and $Y_4$ are preferably occupied by methoxy, ethoxy, chloro, bromo, iodo, primary alkyl, tertiary butyl, primary amine, secondary amine, or tertiary amine substituents, most preferably methoxy, chloro, tertiary butyl, or methyl.

In accordance with a second aspect of the invention, the salen-transition metal complex has the structure:

Structure II

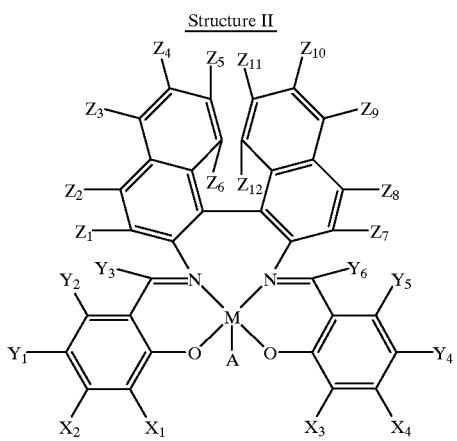

wherein M is a transition metal ion, preferably Mn, and A is an anion, typically Cl; where at least one of $X_1$ or $X_2$ is selected from the group consisting of aryls, primary alkyls, secondary alkyls, tertiary alkyls, and heteroatoms; where at least one of $X_1$ or $X_3$ is selected from the group consisting of aryls, primary alkyls, secondary alkyls, tertiary alkyls, arylalkyls, heteroatoms, and hydrogen, preferably tertiary butyl or hydrogen; and where $Y_1$, $Y_2$, $Y_3$, $Y_4$, $Y_5$, $Y_6$, $Z_1$, $Z_2$, $Z_3$, $Z_4$, $Z_5$, $Z_6$, $Z_7$, $Z_8$, $Z_9$, $Z_{10}$, $Z_{11}$, and $Z_{12}$ are independently selected from the group consisting of hydrogen, halides, alkyls, aryls, amines, alkoxy, substituted alkoxy, arylalkyls, aryloxys, and alkyl groups bearing heteroatoms. Preferably $Y_1$ and $Y_4$ are selected from the group consisting of lower alkyls, alkoxy, halide, and amino groups, more preferably from the group consisting of methoxy, chloro, and primary amine. One preferred embodiment according to this second aspect is the species where: $Y_1$ and $Y_4$ are methoxy: $X_1$ and $X_3$ are independently selected and are hydrogen or tertiary butyl, and the remaining substituents are hydrogen.

In accordance with a third aspect of the invention, the salen-transition metal has the following structure:

Structure III

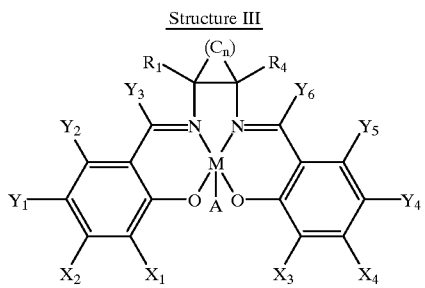

where M is a transition metal ion, typically Mn, and A is an anion, typically Cl; where n is either 4, 5, or 6; where $X_1$, $X_2$, $X_3$, and $X_4$ are independently selected from the group consisting of aryls, arylalkyls, aryloxys, primary alkyls, secondary alkyls, tertiary alkyls, alkoxy, substituted alkoxy, heteroatoms, aminos, quaternary amines, and hydrogen; preferably, at least one of $X_1$ or $X_3$ are selected from the group consisting of aryls, primary alkyls, secondary alkyls, tertiary alkyls, quaternary amines, arylalkyls, heteroatoms, and hydrogen; preferably $X_1$ and $X_3$ are identical and are hydrogen or tertiary butyl; where $Y_1$, $Y_2$, $Y_3$, $Y_4$, $Y_5$, and $Y_6$ are selected from the group consisting of aryls, arylalkyls, primary alkyls, secondary alkyls, tertiary alkyls, alkoxys, substituted alkoxys, aryloxys, halides, heteroatoms, aminos, quaternary amines, and hydrogen; preferably at least one of $Y_1$ or $Y_4$ are selected from the group consisting of aryls, primary alkyls, secondary alkyls, tertiary alkyls, substituted alkoxy, heteroatoms, amines, and halides; more preferably $Y_1$ and $Y_4$ are identical and are either methoxy, chloro, bromo, iodo, tertiary butyl, or amine. $R_1$ and $R_4$ are independently selected from the group consisting of hydrogen, halides, primary alkyls, secondary alkyls, tertiary alkyls, fatty acid esters, alkoxys, or aryls. Preferably $R_1$ and $R_4$ are identical; more preferably $R_1$ and $R_4$ are hydrogen.

Preferred Antioxidant Salen-Metal Species

The following genera of antioxidant salen-metal complexes are preferred for use in the compositions and methods of the present invention, where substituents are not shown they are hydrogen:

Structure IV

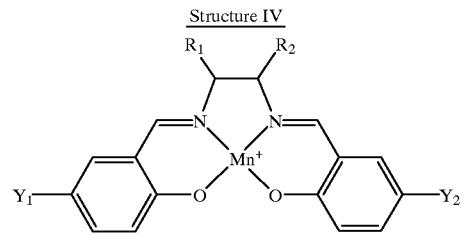

where $Y_1$ and $Y_2$ are independently selected from the group consisting of methoxy, ethoxy, methyl, ethyl, t-butyl, chloro, bromo, iodo, amino, quaternary amine, alkylamino, dialkylamino, and hydrogen; $R_1$ and $R_2$ are independently selected from the group consisting of: phenyl, benzyloxy, chlorobenzyloxy, hydrogen, amino, quaternary amine, or fatty acid ester. Preferably, $Y_1$ and $Y_2$ are identical.

Structure V

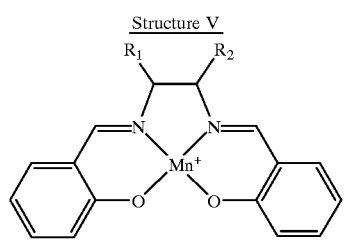

where $R_1$ and $R_2$ are selected independently from the group consisting of: phenyl, benzyloxy, chlorobenzyloxy, hydrogen, amino, quaternary amine, or fatty acid ester. Preferably, $R_1$ and $R_2$ are identical.

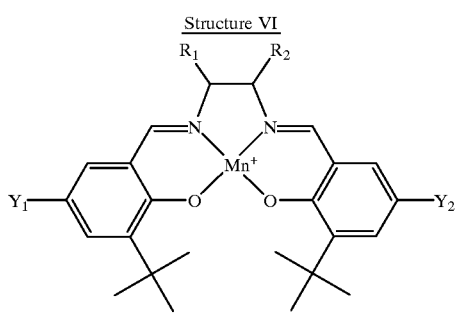

Structure VI where $Y_1$ and $Y_2$ are independently selected from the group consisting of methoxy, ethoxy, methyl, ethyl, t-butyl, chloro, bromo, iodo, amino, quaternary amine, alkylamino, dialkylamino, and hydrogen; $R_1$ and $R_2$ are selected independently from the group consisting of: phenyl, benzyloxy, chlorobenzyloxy, hydrogen, amino, quaternary amine, or fatty acid ester. Preferably, $Y_1$ and $Y_2$ are identical, and $R_1$ and $R_2$ are identical.

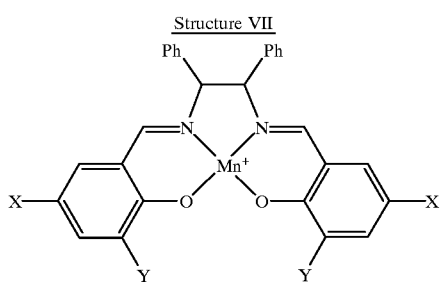

Structure VII where X is selected from the group consisting of methoxy, ethoxy, methyl, ethyl, t-butyl, chloro, bromo, iodo, amino, quaternary amine, alkylamino, dialkylamino, and hydrogen; Y is selected from the group consisting of t-butyl, quaternary amine, amino, and hydrogen.

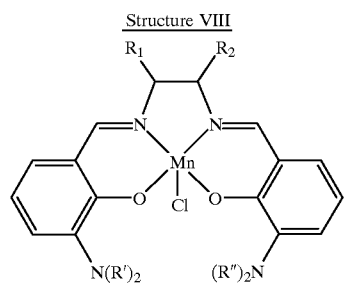

Structure VIII where $R_1$ and $R_2$ are independently selected from the group consisting of aryloxys, alkoxys, aryls, and hydrogen; R' and R" are independently selected from the group consisting of alkyls, aryls, and hydrogen. Preferably, at least one of the amino groups is protonated at physiological pH (i.e., pH 7.3–7.8). Preferred R' or R" alkyls include but are not limited to: methyl, ethyl, and propyl. Preferred $R_1$ and $R_2$ aryloxys include but are not limited to benzyloxy and chlorobenzyloxy. Preferred $R_1$ and $R_2$ alkoxys include but are not limited to ethoxy and methoxy.

A preferred subgenus of Structure VIII includes, but is not limited to:

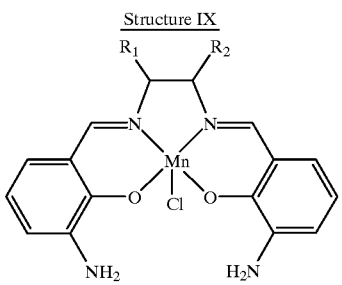

Structure IX where R is selected from the group consisting of alkyls and hydrogen. Preferably, at least one of the amino groups are protonated at physiological pH (i.e., pH 7.3–7.8).

The following species are preferred antioxidant salen-transition metal complexes for formulation in pharmaceutical compositions, dietary supplements, foodstuff preservatives, cosmetics, sunburn preventatives, and other compositions of the invention, and are referenced by structure number (e.g., C1 through C30) for clarity throughout.

C1:

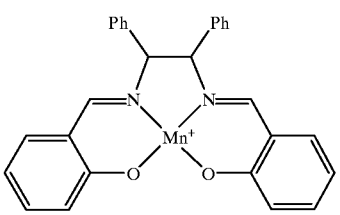

C4:

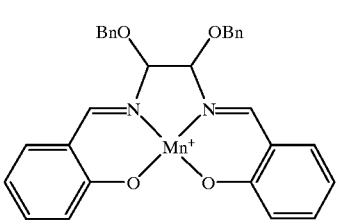

C6:

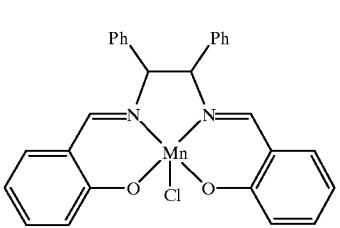

C7:

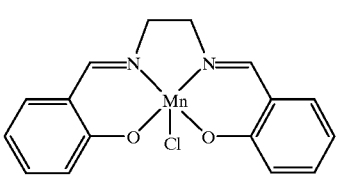

C9:
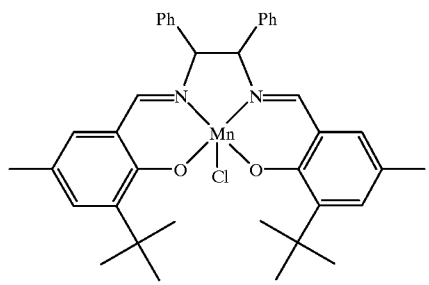
C10:
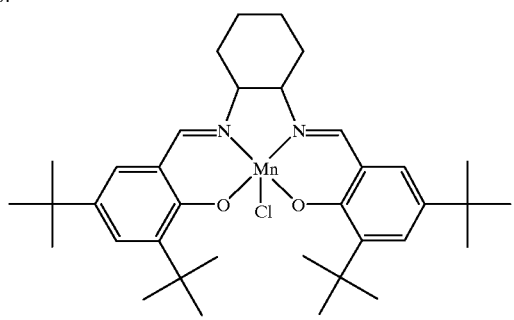
C11:
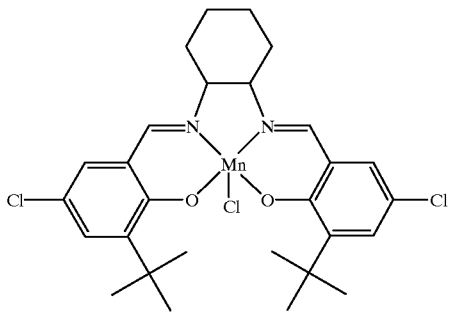
C12:
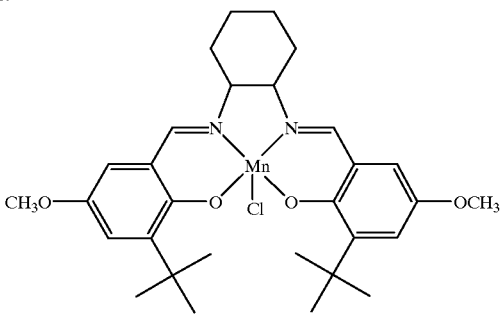
C15:
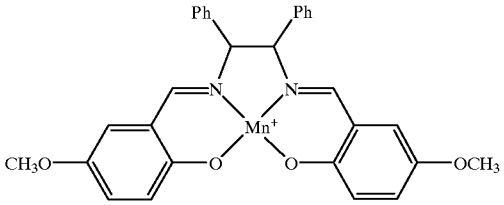
C17:
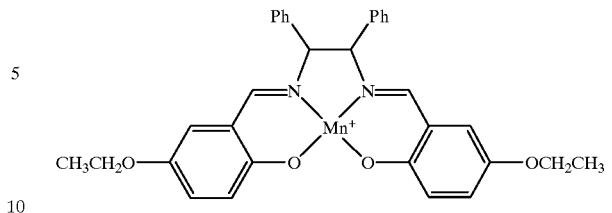
C20:
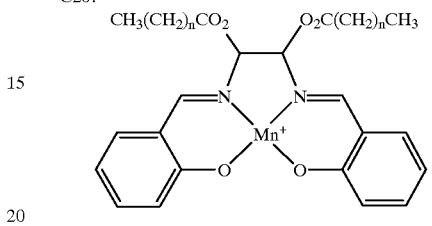
C22:
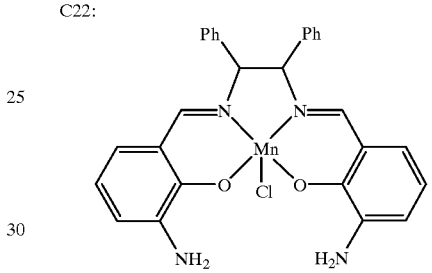
C23:
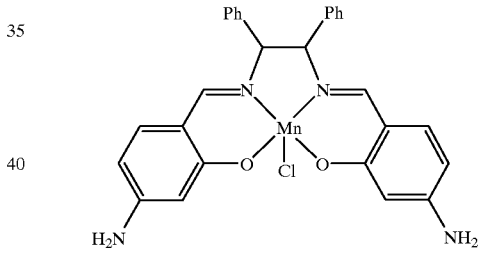
C25:
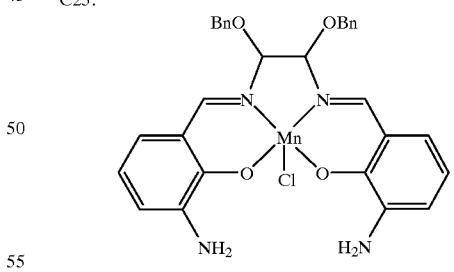
C27:
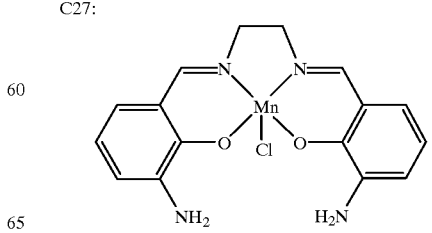

C28:

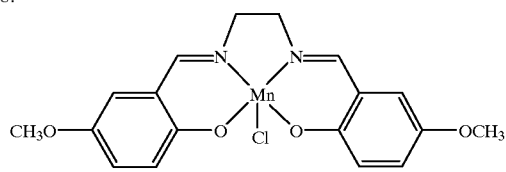

Pharmaceutical Compositions

Figure 1:
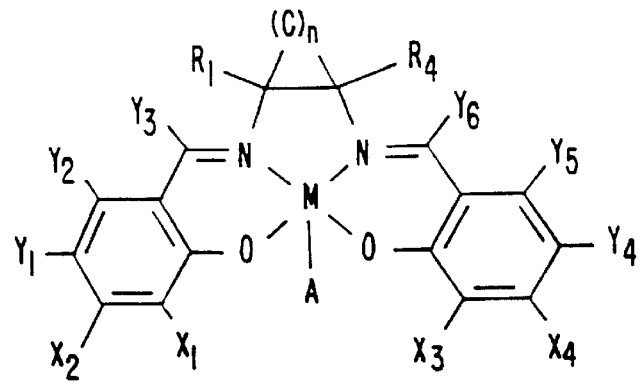
FIG. 1 shows the general structure of salen deriviatives of the invention.
Figure 2:
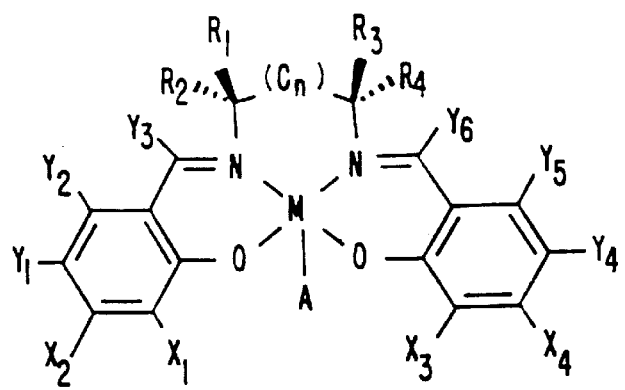
FIG. 2 shows a salen derivative according to the structure shown in FIG. 1, wherein n is 0.

The preferred pharmaceutical compositions of the present invention comprise a therapeutically or prophylactically effective dose of at least one salen derivative-based complex of a transition metal ion. The term "salen" is used herein to refer to those ligands typically formed through a condensation reaction of two molecules of a salicylaldehyde derivative with one molecule of a diamine derivative. While salen ligands are formed from ethylenediamine derivatives, propyl and butyl diamines may also be used to give analogous salen and salen derivatives. Salen derivatives are preferred and their general structure is shown in FIG. 1. A salen derivative where n is 0 is shown in FIG. 2.

As seen in FIG. 1, the two nitrogens and the two oxygens are oriented toward the center of the salen ligand and thus provide a complexing site for the transition metal ion M. Preferably, this metal ion is selected from the group consisting of Mn, Cr, Fe, Ni, Co, Ti, V, Ru, and Os. More preferably, the transition metal ion is selected from the group consisting of Mn, Mg, Cr, Fe, Ni, and Co. Most preferably, the metal ion is Mn.

Preferably, the anion is selected from the group consisting of $PF_6$, $(aryl)_4$, $BF_4$, $B(aryl)_4$, halide, acetate, triflate, tosylate, with halide or $PF_6$ being more preferred, and chloride being most preferred.

FIG. 1 also shows the many sites available for substitution on the salen ligand. Of these sites, it is believed that $R_1$, $R_2$, $R_3$, $R_4$, and $X_1$, $X_2$, $X_3$, $X_4$, $Y_3$ and $Y_6$ are the most important in this first salen-transition metal complex.

Structures I, III, IV, VI, VII, and VIII may have independently selected fatty acid ester substituents at the $R_1$, $R_2$, $R_3$, and $R_4$ positions. When present, the fatty acid esters typically occupy no more than two substituent positions and are usually identical.

Examples of fatty acids suitable to produce the compounds of the instant invention are given in Tables I, II and III below:

TABLE I $CH_3$—$(CH_2)_f$—$(CH=CH)_g$—$(CH_2)_h$—$CO_2H$

| Carbons | f | g | h | Acid Name |
|---|---|---|---|---|
| 16 | 5 | 1 | 7 | Palmitoleic |
| 18 | 7 | 1 | 7 | Oleic |
| 18 | 10 | 1 | 4 | Petroselenic |
| 18 | 5 | 1 | 9 | Vaccenic |
| 18 | 3 | 3 | 7 | Punicic |
| 18 | 1 | 4 | 7 | Parinaric |
| 20 | 9 | 1 | 7 | Gadoleic |
| 22 | 9 | 1 | 9 | Cetoleic |

TABLE II $CH_3$—$(CH_2)_n$—$(CH=CH$—$CH_2)_m$—$(CH_2)_p$—$CO_2H$

| Carbons | f | g | h | Acid Name |
|---|---|---|---|---|
| 18 | 4 | 2 | 6 | Linoleic |
| 18 | 1 | 3 | 6 | Linolenic |
| 20 | 4 | 4 | 2 | Arachidonic |

TABLE III $CH_3$—$(CH_2)_w$—$CO_2H$

| Carbons | w | Acid Name |
|---|---|---|
| 12 | 10 | Lauric |
| 14 | 12 | Myristic |
| 16 | 14 | Palmitic |
| 18 | 16 | Stearic |
| 20 | 18 | Eicosanoic |
| 22 | 20 | Docosanoic |

It will be appreciated that the unsaturated acids occur in isomeric forms due to the presence of the one or more unsaturated positions. The compounds of the present invention are intended to include the individual double bond isomers, as well as mixtures thereof. The fatty acid esters of the present invention can be obtained by known acylation techniques. See, e.g., March, *Advanced Organic Chemistry*, 3rd Ed., John Wiley & Sons, New York (1985), pp. 299, 348–351, and 353–354, incorporated herein by reference.

Preferred Antioxidant Salen-Transition Metal Complexes

FIG. 3 shows structures of preferred antioxidant salen-transition metal complexes of the invention. Example antioxidant salen-transition metal complexes are shown in FIG. 3. Compounds C1, C4, C6, C7, C9, C10, C11, and C12 are particularly preferred for formulation in pharmaceuticals and other antioxidant compositions of the invention. It is believed that C7 is particularly preferred because of its facile preparation and relatively hydrophilic nature which is well-suited to pharmaceutical usage.

A preferred salen-transition metal complex having high superoxide dismutase activity is the C12 compound having the structure:

C12:

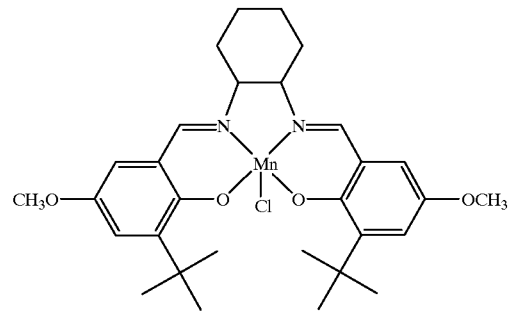

additional preferred congeners of C12 are:

C29:

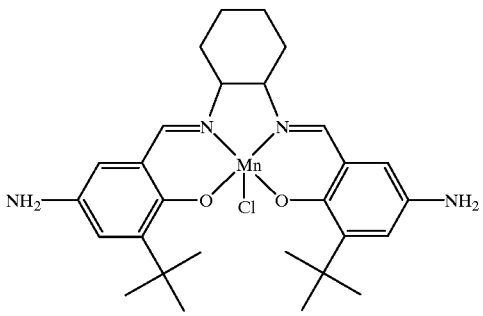

and

C30:

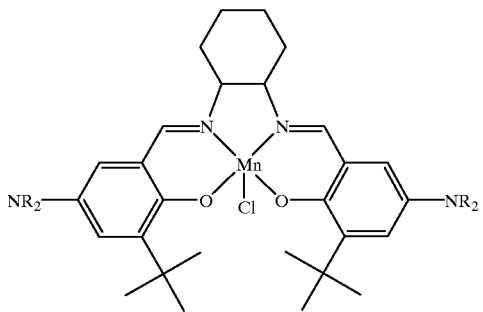

A particularly preferred antioxidant salen-metal complex of the invention is C7:

C7:

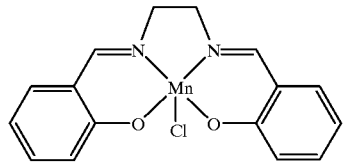

Antioxidant salen-transition metal complexes generally have detectable superoxide dismutase activity and preferably also have catalase activity. Advantageously, C7 is both simple to prepare and relatively hydrophilic, properties which make it particularly well-suited for pharmaceutical use and formulation in aqueous solution. The relatively hydrophilic nature of C7 can be used to advantage in providing antioxidant salen-metal complexes that are readily absorbed and transported in the human body. One advantageous pharmacokinetic property of C7 is believed to be the capacity to cross the blood-brain barrier efficiently.

Preparation of Antioxidant Salen-Transition Metal Complexes

Preparation of salen-transition metal complexes are performed essentially as described in US91/01915 filed Mar. 21, 1991, Fu et al. (1991) *J. Org. Chem.* 56: 6497; Zhang W. and Jacobsen E. N. (1991) *J. Org. Chem.* 56: 2296; Jacobsen et al. (1991) *J. Am. Chem. Soc.* 113: 6703; Zhang et al. (1990) *J. Am. Chem. Soc.* 112: 2801; Lee N. H. and Jacobsen E. N. (1991) *Tetrahedron Lett.* 32: 6533; Jacobsen et al. (1991) *J. Am. Chem. Soc.* 113: 7063; Lee et al. (1991) *Tetrahedron Lett.* 32: 5055, each of which is incorporated herein by reference.

Generally, the preferred route to prepare the antioxidant salen-transition metal complexes of the present invention is a condensation reaction with the substituted salicylaldehyde and the substituted diamine. In general, quantities of these compounds are reacted in a 2 to 1 molar ration in absolute ethanol. The solutions are refluxed typically for 1 hour, and the salen ligand is either precipitated in analytically pure form by addition of water, or the metal complex is generated directly by addition of the metal as its acetate, halide, or triflate salt.

The following procedure is general for the preparation of antioxidant salen-Mn complexes of the formula:

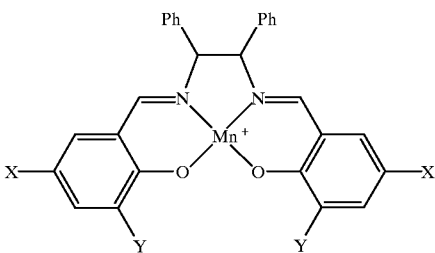

The salen ligand is redissolved in hot absolute ethanol to give a 0.1 M solution. Solid Mn(OAC)$_2$·4H$_2$O (2.0 equivalents) is added in one portion and the solution is refluxed for 1 h. Approximately 3 equivalents of solid LiCl are then added and the mixture is heated to reflux for an additional 0.5 h. Cooling the mixture to 0° C. affords the Mn(III) complex as dark brown crystals which are washed thoroughly with H$_2$O and isolated by filtration in approximately 75% yield. An additional crop of material can be obtained by dropwise addition of H$_2$O to the mother liquor. Combined yields of catalyst are typically about 80–95% for this step, and about at least 80–90% overall from the optically pure 1,2-diphenylethylene diamine.

Another example of the method of preparing the antioxidant salen-Mn complexes are described as follows: Most preferably, the starting diamine is R,R- or S,S-1,2-diamino-1,2-diphenylethane and the starting salicylaldehyde is 3-tert-butylsalicylaldehyde. A solution of 2.0 mmol of 3-tert-butylsalicylaldehyde in 3 ml of absolute ethanol is added dropwise to a solution of 1.0 mmol of (R,R)-1,2-diamino-1,2-diphenylethane in 5 ml of ethanol. The reaction mixture is heated to reflux for 1 h and then 1.0 mmol of Mn(Oac)$_2$·4H$_2$O is added in one portion to the hot (60° C.) solution. The color of the solution immediately turns from yellow to brown upon addition. It is refluxed for an additional 30 min and then cooled to room temperature. A solution of 10% NaCl (5 ml) is then added dropwise and the mixture stirred for 0.5 h. The solvents are then removed in vacuo and the residue is triturated with 50 ml of CH$_2$—Cl$_2$ and 50 ml of H$_2$O. The organic layer is separated and the brown solution is washed with saturated NaCl. Separation of the organic phase and removal of solvent resulted in a crude material which can be recrystallized from C$_6$H$_6$/C$_6$H$_{14}$ to give a (R,R)-salen-Mn complex.

The synthesis of the antioxidant salen-transition metal complexes of the invention may be routinely accomplished by those of ordinary skill in the art according to the cited publications.

The SOD activity of the prepared salen-Mn complexes is determined according to standard assay methods for SOD activity known in the art and exemplified infra. Salen-metal complexes having at least 0.01 unit of SOD activity per millimole/liter in aqueous solution are antioxidant salen-metal complexes; preferably antioxidant salen-metal complexes have at least about 1 unit of SOD activity per millimole/liter; and more preferably have at least about 100 units of SOD activity per millimole/liter; frequently having more that 500 to 1000 units of SOD activity per mM or more. For some medical uses where catalase activity is preferably supplemented, it is advantageous that the SOD mimetic salen-metal complex also possesses detectable catalase activity (e.g., C4, C7, C9, C10, C11, C12); typically at least 10 units of catalase activity per mM, and frequently at least 100 units of catalase activity per mM.

Pharmaceutical Formulations

Pharmaceutical compositions comprising an antioxidant salen-transition metal complex of the present invention are useful for topical and parenteral administration, i.e., subcutaneously, intramuscularly or intravenously. The finding that salen-metal complexes possess SOD activity in vitro as well as functioning in vivo indicates that antioxidant salen-metal complexes are suitable SOD mimetics for pharmaceutical use. The antioxidant salen-metal complexes are suitable for administration to mammals, including human patients and veterinary patients.

The compositions for parenteral administration will commonly comprise a solution of an antioxidant salen-transition metal complex or a cocktail thereof dissolved in an acceptable carrier, preferably an aqueous carrier or organic solvent (e.g., DMSO, solvated PEG, etc.). Since many of the salen-Mn complexes of the invention are lipophilic, it is preferable to include in the carrier a hydrophobic base (e.g., polyethylene glycol, Tween 20). A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the antioxidant salen-transition metal complex(es) in these formulations can vary widely, i.e., from less than about 1 nM, usually at least about 0.1 mM to as much as 100 mM and will be selected primarily based on fluid volumes, viscosities, etc., in accordance with the particular mode of administration selected. Most usually, the antioxidant salen-metal complex is present at a concentration of 0.1 mM to 10 mM. For example, a typical formulation for intravenous injection comprises a sterile solution of an antioxidant salen-metal complex (e.g., C7) at a concentration of 5 mM in Ringer's solution. The generally hydrophobic nature of some of the preferred antioxidant salen-metal complexes indicates that a hydrophobic vehicle may be used, or that an aqueous vehicle comprising a detergent or other lipophilic agent (e.g., Tween, NP-40, PEG); alternatively, the antioxidant salen complexes may be administered as a suspension in an aqueous carrier, or as an emulsion.

Thus, a typical pharmaceutical composition for intramuscular injection could be made up to contain 1 ml sterile buffered water, and about 1–100 mg of antioxidant salen-transition metal complex(es). A typical composition for intravenous infusion can be made up to contain 250 ml of sterile Ringer's solution, and about 100–1000 mg of antioxidant salen-transition metal complex(es). Lipophilic agents may be included in formulations of lipophilic salen-metal complexes. Actual methods for preparing parenterally administrable compositions will be known or apparent to those skilled in the art and are described in more detail in, for example, *Remington's Pharmaceutical Science,* 15th Ed., Mack Publishing Company, Easton, Pa. (1980), which is incorporated herein by reference. A typical pharmaceutical composition for topical application can be made with suitable dermal ointments, creams, lotions, ophthalmic ointments and solutions, respiratory aerosols, and other excipients. Excipients should be chemically compatible with the antioxidant salen-transition metal complex(es) that are the active ingredient(s) of the preparation, and generally should not increase decomposition, denaturation, or aggregation of active ingredient(s). Frequently, excipients will have lipophilic components such as oils and lipid emulsions.

The antioxidant salen-transition metal complex(es) of this invention can be lyophilized for storage and reconstituted in a suitable carrier prior to use. It will be appreciated by those skilled in the art that lyophilization and reconstitution can lead to varying degrees of antioxidant activity loss, and that use levels may have to be adjusted to compensate.

The compositions containing the present antioxidant salen-transition metal complex(es) or cocktails thereof can be administered for prophylactic and/or therapeutic treatments. In therapeutic application, compositions are administered to a patient already affected by the particular free radical-associated disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration, but generally range from about 1 mg to about log of antioxidant salen-transition metal complex (es) per dose, with dosages of from 10 mg to 2000 mg per patient being more commonly used. For example, for treating acute myocardial ischemia/reoxygenation episodes, about 100 to 1000 mg of a antioxidant salen metal complex (e.g., C7) may be administered systemically by intravenous infusion; at least about 10 mg to 500 mg of antioxidant salen-metal complex(es) may be administered by intrapericardial injection to provide elevated local concentrations of SOD activity in the myocardium.

In prophylactic applications, compositions containing the antioxidant salen-transition metal complex(es) or cocktails thereof are administered to a patient not already in a disease state to enhance the patient's resistance or to retard the progression of disease. Such an amount is defined to be a "prophylactically effective dose." In this use, the precise amounts again depend upon the patient's state of health and general level of immunity, but generally range from 1 mg to 10 g per dose, especially 10 to 1000 mg per patient. A typical formulation of an antioxidant salen-metal complex such as C7 will contain between about 25 and 250 mg of the salen-metal complex in a unit dosage form.

Single or multiple administrations of the compositions can be carried out with dose levels and dosing pattern being selected by the treating physician. In any event, the pharmaceutical formulations should provide a quantity of the antioxidant salen-transition metal complex(es) of this invention sufficient to effectively treat the patient.

Kits can also be supplied for use with the subject antioxidant salen-transition metal complex(es) for use in the protection against or therapy for a free radical-associated disease. Thus, the subject composition of the present invention may be provided, usually in a lyophilized form or aqueous solution in a container, either alone or in conjunction with additional antioxidant salen-transition metal complex(es) of the desired type. The antioxidant salen-transition metal complex(es) are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of antioxidant salen-transition metal complex(es), and usually present in total amount of at least about 0.001% based again on the concentration. Frequently, it will be desirable to include an inert extender or excipient to dilute the active ingredients, where the excipient may be present in from about 1 to 99.999% wt. of the total composition.

Salen-Mn complexes, preferably compound C12 or C7, can be incorporated into a hypothermic cardioplegia solution at a concentration of at least about 1 mM into a solution formulation according to Amano et al. (1982) *Jpn. J. Surg.* 12: 87, incorporated herein by reference. Most preferably, C7 is included in the cardioplegia solution.

The dosage of SOD-mimetic salen-metal complex(es) will vary with each particular application. Typically, the composition is administered either systemically or topically. Systemic administration includes per os and parenteral routes; topical administration includes in situ applications. The in situ means includes, for example, administering an SOD-mimetic salen-metal complex by endoscopic bolus wash and/or paravenous injection, or in the case of lower GI treatments, by enema. Parenteral routes may include, for example, subcutaneous, intradermal, intramuscular, and intravenous routes. The amount of SOD-mimetic salen-metal complex(es) will range from about 2 to 5,000 mg or more, typically 10 to 1000 mg, depending on the administration interval and route, which can range from a single oral dose, parenteral dose and/or topical dose to multiple oral doses, parenteral doses, and/or topical doses over a few days or greater than 5 weeks. The dosage may also vary with the severity of the disease.

In Vitro and Research Administration

In another aspect of the invention, antioxidant salen-transition metal complexes of the invention are employed to modulate the expression of naturally-occurring genes or other polynucleotide sequences-under the transcriptional control of an oxidative stress response element (e.g., an antioxidant responsive element, ARE), such as an antioxidant response element of a glutathione S-transferase gene or a NAD(P)H:quinone reductase gene (Rozen et al. (1992) *Arch. Biochem. Biophys.* 292: 589; Favreau and Pickett (1991) *J. Biol. Chem.* 266: 4556; Rushmore and Pickett (1991) *Methods Enzymol.* 206: 409; Rushmore and Pickett (1990) *J. Biol. Chem.* 265: 14648; Keyse et al. (1992) *Nature* 359: 644, incorporated herein by reference). Transgenes, homologous recombination constructs, and episomal expression systems (e.g., viral-based expression vectors) comprising a polynucleotide sequence under the transcriptional control of one or more ARE linked to a promoter will be made by those of skill in the art according to methods and guidance available in the art, as will transformed cells and transgenic nonhuman animals harboring such polynucleotide constructs. The antioxidant salen-metal complexes may be used to modulate the transcription of ARE-regulated polynucleotide sequences in cell cultures (e.g., ES cells) and in intact animals, particularly in transgenic animals wherein a transgene comprises one or more AREs as transcriptional regulatory sequences. For transformed or transgenic cell cultures, a dose-response curve is generated by titrating transcription rate of the ARE-controlled polynucleotide sequence against increasing concentrations of antioxidant salen-metal complex(es), which will reduce the transcription rate induced by oxidant agents (e.g., benzoyl peroxide, glutathione-depleting agent) or oxidative stress. Conversely, high levels of SOD-mimetic salen-metal complexes may produce oxidative stress and free radical generation. Similar dose-response titration can be performed in transgenic animals, such as transgenic mice, harboring an ARE-controlled transgene sequence.

In Vivo Administration

According to this invention, a therapeutically or pharmaceutically effective amount of an antioxidant salen-transition metal complex is administered to a patient to treat or prevent a free radical-associated disease. The required dosage will depend upon the nature of the free radical-associated disease, the severity and course of the disease, previous therapy, the patient's health status and response to the antioxidant salen-transition metal complex, and the judgment of the treating physician. Typically, at least one species of antioxidant salen-Mn complex is administered as the sole active ingredient, or in combination with one or more other active ingredients, typically selected from the group consisting of: N-2-mercaptopropionylglycine, N-acetylcysteine, glutathione, dimethyl thiourea, desferrioxamine, mannitol, $\alpha$-tocopherol, ascorbate, allopurinol, 21-aminosteroids, calpain inhibitors, glutamate receptor antagonists, tissue plasminogen activator, streptokinase, urokinase, nonsteroidal anti-inflammatory agent, cortisone, and carotenoids. Antioxidant salen-Mn complexes may also be administered in conjunction with polypeptides having SOD and/or catalase activity, particularly in view of the capacity of the salen-Mn complexes, unlike SOD polypeptides, to cross the blood-brain barrier and thereby complement systemic SOD administration.

The present invention includes a method of treating patients, such as humans, who have a free radical-associated disease with a prophylactically effective or therapeutically effective amount of a antioxidant salen-transition metal complex, typically a salen-Mn complex, preferably C7. This method can be used to treat patients at various stages of their diseases or to prevent development of free radical-associated diseases in patients. In addition, the treatment can be administered to prevent or reduce, as a prophylactic, the age-adjusted probability of developing a neoplasm and/or the age-adjusted mortality rate and/or the rate of senescence.

The antioxidant salen-metal complexes of the invention can also be administered to patients who are infected with a human immunodeficiency virus (e.g., HIV-1) or who are at risk of becoming infected with a human immunodeficiency virus. The antioxidant salen-metal complexes, typified by C7, can prevent or inhibit the induction of HIV-1 replication in CD4$^+$ lymphocytes by tumor necrosis factor (TNF) and/or prevent damage to or death of CD4$^+$ cells as a consequence of HIV-1 infection. Without wishing to be bound by any particular theory of HIV-1 replication or HIV-1 pathogenesis, it is believed that administration of an antioxidant salen-metal complex, such as C7, can inhibit and/or slow the development of HIV-1 related pathology and/or can reduce the rate of decline of the CD4$^+$ lymphocyte population in HIV-infected individuals. The antioxidant salen-metal complexes, such as C7, can also inhibit pathology resulting from excessive or inappropriate levels of TNF, both in AIDS and in other conditions (e.g., septic shock).

Frequently, a dosage of about 50 to 5000 mg will be administered to a patient with HIV and/or with excessive or inappropriate levels of TNF, either in single or multiple doses, to reduce or retard the development of pathology and clinical symptoms. Antioxidant salen-metal complexes may be administered therapeutically to treat viral diseases other than HIV.

Since oxidative damage occurs proportionately to the abundance of free radicals and reactive oxygen species, it is expected that administration of antioxidant salen-transition metal complexes at even low levels will confer a protective effect against oxidative damage; thus it is expected that there is no threshold level below which antioxidant salen-Mn complexes are ineffective.

In general for treatment of free radical-associated diseases, a suitable effective dose of the antioxidant salen-Mn complex will be in the range of 0.01 to 1000 milligram (mg) per kilogram (kg) of body weight of recipient per day, preferably in the range of 1 to 100 mg per kg of body weight per day. The desired dosage is preferably presented in one, two, three, four or more subdoses administered at appropriate intervals throughout the day. These subdoses can be administered as unit dosage forms, for example, containing 5 to 10,000 mg, preferably 10 to 1000 mg of active ingredient per unit dosage form.

The composition used in these therapies can be in a variety of forms. These include, for example, solid, semi-solid and liquid dosage forms, such as tablets, pills, powders, liquid solutions or suspensions, liposome preparations, injectable and infusible solutions. The preferred form depends on the intended mode of administration and therapeutic application. Typically, a sterile solution of a salen-metal complex in an aqueous solvent (e.g., saline) will be administered intravenously. The compositions also preferably include conventional pharmaceutically acceptable carriers and adjuvants which are known to those of skill in the art. See, e.g., *Remington's Pharmaceutical Sciences*, Mack Publishing Co.: Easton, Pa., 17th Ed. (1985). Generally, administration will be by oral or parenteral (including subcutaneous, intramuscular, intravenous, and intradermal) routes, or by topical application or infusion into a body cavity, or as a bathing solution for tissues during surgery.

It should, of course, be understood that the methods of this invention can be used in combination with other antioxidant agents that have SOD activity, catalase activity, GSH-Px activity, or are free radical scavengers or inhibitors of free radical formation. While it is possible to administer the active ingredient of this invention alone, it is believed preferable to present it as part of a pharmaceutical formulation. The pharmaceutically acceptable formulations of the present invention comprise at least one compound of this invention in a therapeutically or pharmaceutically effective dose together with one or more pharmaceutically or therapeutically acceptable carriers and optionally other therapeutic ingredients. Preferred carriers include inert, non-toxic solids (e.g., mannitol, talc) and buffered saline. Various considerations are described, e.g., in Gilman et al. (eds) (1990) Goodman and Gilman's: *The Pharmacological Bases of Therapeutics,* 8th Ed., Pergamon Press; and *Remington's* supra, each of which is hereby incorporated herein by reference. Methods for administration are discussed therein, e.g., for oral, intravenous, intraperitoneal, or intramuscular administration, and others. Pharmaceutically acceptable carriers will include water, saline, buffers, and other compounds described, e.g., in the Merck Index, Merck & Co., Rahway, N.J., incorporated herein by reference. As used herein, the term "pharmaceutically acceptable carrier" encompasses any of the standard pharmaceutical carriers such as sterile solutions, tablets, coated tablets, and capsules. Typically such carriers contain excipients such as starch, milk, sugar, certain types of clay, gelatin, stearic acids or salts thereof, magensium or calcium sterate, talc, vegetable fats or oils, gums, glycols, or other known excipients. Such carriers may also include flavor and color additives or other ingredients. Compositions comprising such carriers are formulated by well known conventional methods. Depending on the intended mode of administration and the intended use, the compositions may be in the form of solid, semi-solid, or liquid dosage forms, such, for example, as powders, granules, crystals, liquids, suspensions, liposomes, pastes, cremes, salves, etc., and may be in unit-dosage forms suitable for administration of relatively precise dosages. For semi-solid compositions, as would be appropriate for pastes and creams intended for topical administration, the salen-metal complexes can be provided separately or may be compounded with conventional nontoxic carriers such as, for example, aloe vera gel, squalane, glycerol sterate, polyethylene glycol, cetyl alcohol, stearic acid, and propylene glycol, among others. Such compositions may contain about 0.005–100% active ingredient, more preferably about 0.5–25%. The concentration of the salen-metal complexes in these formulations can vary widely, and will be selected primarily by intended use, viscosities, etc., in accordance with the particular mode of administration selected. The composition or formulation to be administered will, in any event, contain a quantity of the salen-metal complexes sufficient to achieve the desired therapeutic or prophylactic effect in the subject being treated. Typical compositions include lotions containing water and/or alcohols and emollients such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers.

The pharmaceutical compositions will be administered by parenteral or oral administration for prophylactic and/or therapeutic treatment. The pharmaceutical compositions can be administered in a variety of unit dosage forms depending upon the method of administration. For example, unit dosage forms suitable for oral administration include powder, tablets, pills, capsules, and dragees.

The pharmaceutical compositions will often be administered intravenously. Thus, this invention provides compositions for intravenous administration which comprise a solution of the compound dissolved or suspended in an acceptable carrier, preferably an aqueous carrier. A variety of aqueous carriers can be used, e.g., water, buffered water, 0.4% saline, and the like. Often, the antioxidant salen-metal complex(es), such as C7 or C12, may be dissolved in an organic solvent (e.g., dimethylsulfoxide) and either applied directly or diluted into an aqueous solvent. Typically, antioxidant salen-metal complexes that are relatively lipophilic (e.g., C9, C12) are dissolved in an organic solvent such as DMSO and, if desired, subsequently diluted into a more polar solvent, such as water. These compositions will sometimes be sterilized by conventional, well known sterilization techniques, or can preferably be sterile filtered. The resulting aqueous solutions can be packaged for use as is, or lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.001–95% of active ingredient, preferably about 20%.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective amount or dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective amount or dose." In this use, the precise amounts again depend on the patient's state of health and weight.

For solid compositions, conventional non-toxic solid excipients include, for example, pharmaceutical grades of mannitol, lactose, starch, magnesium stearate, talcum, celluloses, glucose, sucrose, magnesium carbonate, and the like may be used. The active compound as defined above may be formulated as suppositories using, for example, triglycerides, for example, the Witepsols, as the carrier. Liquid pharmaceutically administerable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pennsylvania, 17th Edition, 1985. The composition or formulation to be administered will, in any event, contain an effective amount of the active compound (s).

For oral administration, a pharmaceutically acceptable non-toxic composition is formed by the incorporation of any of the normally employed excipients, such as, for example pharmaceutical grades of mannitol, lactose, starch, magnesium stearate, talcum, celluloses, glucose, sucrose, magnesium, carbonate, and the like. Such compositions take the form of solutions, suspensions, tablets, capsules, powders, sustained release formulations and the like. Such compositions may contain 0.01–95% active ingredient, preferably 1–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is incorporated herein by reference. Antioxidant salen-metal complexes may be administered by transdermal patch (e.g., iontophoretic transfer) for local or systemic application.

Once detectable improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms or as a prophylactic measure to prevent disease symptom recurrence.

Antioxidant salen-metal complex(es) can also be added to extravasated blood for transfusion to inhibit oxyradical damage to the blood cells and components during storage; similarly, antioxidant salen-metal complexes can also reduce oxyradical damage to blood cells in vivo.

Antioxidant salen-metal complex(es) can also be added to rinse or storage solutions for organs and tissues, such as for organ transplantation or for surgical rinses. For example, excised organs are often placed in a preservation solution prior to transplant into a recipient. Inclusion of at least one species of antioxidant salen-metal complex in a preservation solution, usually at a concentration of about 0.01 mM to 10 mM, is desirable for reducing damage due to ischemia during storage and reperfusion injury following reimplantation in the recipient. Various solutions described in the art are suitable for the inclusion of a salen-metal complex, including but not limited to those described in U.S. Pat. No. 5,145,771; Beyersdorf (1990) Chem Abst. 113: 84849w; U.S. Pat. Nos. 4,879,283; 4,873,230; and 4,798,824, incorporated herein by reference.

Typically the antioxidant salen-metal complex is present in the rinse or storage solution at a concentration of about 10 $\mu$M to about 10 mM, and most usually is present at 1 mM. For example, but not to limit the invention, a suitable rinse solution comprises Ringer's solution (102 mM NaCl, 4 mM KCl, 3 mM $CaCl_2$, 28 mM sodium lactate, pH 7.0) or Ringer's solution with 0.1 mM adenosine, and the antioxidant salen-Mn complex C7 at a final concentration of 1 mM. The rinse solution can further comprise additional antioxidants (e.g., glutathione, allopurinol). Preservation or rinse solutions containing an antioxidant salen-metal complex can be used to provide enhanced storage or irrigation of organs (e.g., kidney, liver, pancreas, lung, fetal neural tissue, heart, vascular grafts, bone, ligament, tendon, skin) which is believed to enhance the viability of the tissue and increase resistance to oxidative damage (e.g., as a consequence of ischemia/reperfusion).

Without wishing to be bound by any particular theory of antioxidant or catalytic oxyradical scavenger action, it is believed that excessive dosages or concentrations of the catalytic salen-metal complex(es) of the invention might actually produce free radicals, such as superoxide, possibly in a manner analogous to the presence of large amounts of circulating free iron. On this basis, it is believed that prolonged administration of excessive doses of salen-metal complexes are preferably avoided for antioxidant therapy. However, it is also believed that administration of excessive doses of a catalytically active salen-metal complex may be used to advantage in generating free radicals, such as superoxide, in local areas (e.g., for acne treatment, skin cancer treatment, papillomas) or in cell cultures or transgenic animals harboring a transgene under the transcriptional control of a ARE. For enhancing free radical (e.g., superoxide) generation, it may be preferable to expose the local site, cell culture, or transgenic animal to a hyberbaric environment and/or an oxygen-enriched atmosphere (e.g., greater than about 21 percent molecular oxygen).

Alternatively, the capacity of the antioxidant salen-metal complexes to catalyze the decomposition of reactive oxygen species can be used to advantage to inhibit or slow damage to biological tissues and cells. For example, benzoyl peroxide is a widely used treatment for acne lesions; excessive or inappropriate application of benzoyl peroxide (e.g., accidental application to the eyes) may be treated by local (or if desired, systemic) administration of an antioxidant salen-metal complex (e.g., C7). Similarly, oxyradical-induced damage to connective tissues (e.g., collagen) attendant to exposure to UV light, cigarette smoking, and senescence may be reduced by administration of an antioxidant salen-metal complex approximately concomitant with the exposure to UV light, cigarette smoking, or other oxyradical-generating process (e.g., cellular senescence).

Chemoprotection and Radioprotection

Antioxidant salen-transition metal complexes, typically antioxidant salen-Mn complexes, such as compound C7, are used to protect cells and tissues from free radical-producing agents, such as ionizing radiation and chemotherapeutic agents (e.g., bleomycin). Preferably, a protective dosage comprising at least about 1 $\mu$g of salen-Mn complex/kg bodyweight is administered by one or more of several routes (e.g., oral, intraveneous, intraperitoneal, intragastric lavage, enema, portal vein infusion, topical, or inhalation of mist), preferably by injection of liposomes or immunoliposomes for targeted delivery of the antioxidant salen-Mn complexes to protect normal cells, for example, against free radical toxicity associated with chemotherapy or radiotherapy of a neoplasm. The antioxidant salen-transition metal complexes are preferably preadministered to the patient prior to the commencement of the chemotherapy and/or radiotherapy, usually within about 24 hours of commencement, and preferably within about 3–6 hours of commencement of the chemotherapy and/ or radiotherapy. Antioxidant salen-Mn may be continually administered to the patient during the course of therapy.

For example, a solution of an antioxidant salen-metal complex can be encapsulated in micelles to form immunoliposomes (U.S. Pat. Nos. 5,043,164, 4,957,735, 4,925,661; Connor and Huang (1985) *J. Cell Biol.* 101: 582; Lasic D D (1992) *Nature* 355: 279; *Novel Drug Delivery* (eds. Prescott L F and Nimmo W S: Wiley, New York, 1989); Reddy et al. (1992) *J. Immunol.* 148: 1585; incorporated herein by reference). The immunoliposomes containing the antioxidant salen-metal species will comprise a targeting moiety (e.g., monoclonal antibody) that targets the immunoliposomes to non-neoplastic cells that are otherwise sensitive to radiotherapy or chemotherapy. For example, immunoliposomes having a monoclonal antibody that binds specifically to a hematopoietic stem cell antigen not present on the cancer cells of the individual may be used to target antioxidant salen-metal complexes to hematopoietic stem cells and thereby protect said stem cells against radiotherapy or chemotherapy used to treat the cancer. Such a strategy is preferably employed when the chemotherapeutic agent forms free radicals in vivo (e.g., bleomycin).

Antioxidant salen-Mn complexes are also administered to individuals to prevent radiation injury or chemical injury by free radical generating agents. Military personnel and persons working in the nuclear, nuclear medicine, and/or chemical industries may be administered salen-Mn complexes prophylactically. Antioxidant salen-metal complexes may also be used as chemoprotective agents to prevent chemical carcinogenesis; particularly by carcinogens which form reactive epoxide intermediates (e.g., benzo-[a]-pyrene, benzanthracene) and by carcinogens or promoting agents which form free radicals directly or indirectly (e.g., phenobarbital, TPA, benzoyl peroxide, peroxisome proliferators: ciprofibrate, clofibrate). Persons exposed to such chemical carcinogens are pretreated with an antioxidant salen-metal complex to reduce the incidence or risk of developing neoplasia.

Antioxidant salen-metal complexes can also be formulated into a lipophilic base (or, if desired, an aqueous carrier) for topical application in cosmetics or sunburn-prevention creams and lotions. A typical cosmetic or sunburn-prevention cream or lotion will comprise about between 1 mg to 50 mg of antioxidant salen-metal complex per gram of cosmetic or sunburn-prevention cream or lotion.

Antioxidant salen-metal complexes may also be administered to deep-divers or individuals exposed to hyberbaric environments were oxygen toxicity presents a health risk. Administration of an efficacious dose of an antioxidant salen-metal complex to an individual may permit the breathing or hyberbaric and/or oxygen-enriched gases with a reduced risk of oxygen toxicity. It is also believed that administration of an efficacious dosage of an antioxidant salen-metal complex can reduced toxicity and biological damage associated with exposure to ozone. Prophylactic administration of an antioxidant salen-metal complex to humans who are or will be exposed to ozone is expected to confer an enhanced resistance to ozone toxicity, such as the ozone-induced lung damage noted in geographical areas with high ozone levels (e.g., Los Angeles).

Cosmetic Formulations

As described above, antioxidant salen-metal complexes of the invention can be formulated into a cosmetic base for topical application and/or for reducing oxidation of the cosmetic by molecular oxygen and oxyradicals.

Anti-Inflammatory Compositions

In an aspect, antioxidant salen-metal agents of the invention can be formulated with an anti-inflammatory agent in a cosmetic base or dental linament (periodontal disease) for topical application for local prevention of inflammation and/or tissue damage consequent to inflammation. A variety of steroidal and non-steroidal anti-inflammatory agents can be combined with an antioxidant salen-metal compound.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprecinisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use in the present invention is hydrocortisone.

Specific non-steroidal anti-inflammatory agents useful in the composition of the present invention include, but are not limited to: piroxicam, isoxicam, tenoxicam, sudoxicam, CP-14,304, aspirin, disalcid, benorylate, trilisate, safapryn, solprin, diflunisal, fendosal, diclofenac, fenclofenac, indomethacin, sulindac, tolmetin, isoxepac, furofenac, tiopinac, zidometacin, acemetacin, fentiazac, zomepirac, clidanac, oxepinac, felbinac, mefenamic, meclofenamic, flufenamic, niflumic, tolfenamic acids, ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, tiaprofenic, phenylbutazone, oxyphenbutazone, feprazone, azapropazone, and trimethazone, among others. Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred and ibuprofen, naproxen, and flufenamic acid are most preferred.

Finally, so-called "natural" anti-inflammatory agents are useful in the present invention. For example, candelilla wax, alpha bisabolol, aloe vera, Manjistha (extracted from plants in the genus Rubia, particularly *Rubia Cordifolia*), and Guggul (extracted from plants in the genus Commiphora, particularly *Commiphora Mukul*), may be used.

The pharmaceutical/cosmetic compositions of the present invention formulated as solutions typically include a pharmaceutically- or cosmetically-acceptable organic solvent. The terms "pharmaceutically-acceptable organic solvent" and "cosmetically-acceptable organic solvent" refer to an organic solvent which, in addition to being capable of having dispersed or dissolved therein the salen-metal compound, and optionally also an anti-inflammatory agent, also possesses acceptable safety (e.g. irritation and sensitization characteristics), as well as good aesthetic properties (e.g., does not feel greasy or tacky). The most typical example of such a solvent is isopropanol. Examples of other suitable organic solvents include: propylene glycol, polyethylene glycol (200–600), polypropylene glycol (425–2025), glycerol, 1,2,4-butanetriol, sorbitol esters, 1,2, 6-hexanetriol, ethanol, butanediol, water and mixtures thereof. These solutions contain from about 0.001% to about 20%, preferably from about 0.1% to about 10%, antioxidant salen-metal complex, from about 0.01% to about 5%, preferably from about 0.5% to about 2% of an anti-inflammatory agent, and from about 80% to about 99%, preferably from about 90% to about 98%, of an acceptable organic solvent.

As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32–43 (1972), incorporated herein by reference, contains numerous examples of suitable materials. Examples of classes of useful emollients include the following:

1. Hydrocarbon oils and waxes. Examples include mineral oil, petrolatum, paraffin, ceresin, ozokerite, microcrystalline wax, polyethylene, and perhydrosqualene.
2. Silicone oils, such as dimethyl polysiloxanes, methylphenyl polysiloxanes, water-soluble and alcohol-soluble silicone glycol copolymers.
3. Triglyceride esters, for example vegetable and animal fats and oils. Examples include castor oil, safflower oil, cottonseed oil, corn oil, olive oil, cod liver oil, almond oil, avocado oil, palm oil, sesame oil, and soybean oil.
4. Acetoglyceride esters, such as acetylated monoglycerides.
5. Ethoxylated glycerides, such as ethoxylated glyceryl monostearate.
6. Alkyl esters of fatty acids having 10 to 20 carbon atoms. Methyl, isopropyl, and butyl esters of fatty acids are particularly useful herein. Examples of other useful alkyl esters include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, auryl lactate, myristyl lactate, and cetyl lactate.
7. Alkenyl esters of fatty acids having 10 to 20 carbon atoms. Examples include oleyl myristate, oleyl stearate, and oleyl oleate.
8. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.
9. Fatty alcohols having 10 to 20 carbon atoms. Lauryl, myristyl, cetyl, hexadecyl, stearyl, isostearyl, hydroxystearyl, oleyl, ricinoleyl, behenyl, and erucyl alcohols, as well as 2-octyl dodecanol, are examples of satisfactory fatty alcohols.
10. Fatty alcohol ethers. Ethoxylated fatty alcohols of 10 to 20 carbon atoms include the lauryl, cetyl, stearyl, isostearyl, oelyl, and cholesterol alcohols having attached thereto from 1 to 50 ethylene oxide groups or 1 to 50 propylene oxide groups.
11. Ether-esters such as fatty acid esters of ethoxylated fatty alcohols.
12. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

13. Polyhydric alcohols and polyether derivatives. Propylene glycol, dipropylene glycol, polypropylene glycols 2000 and 4000, polyoxyethylene polyoxypropylene glycols, polyoxypropylene polyoxyethylene glycols, glycerol, sorbitol, ethoxylated sorbitol, hydroxypropyl sorbitol, polyethylene glycols 200–6000, methoxy polyethylene glycols 350, 550, 750, 2000 and 5000, poly[ethylene oxide] homopolymers (100,000–5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), C15–C18 vicinal glycol, and polyoxypropylene derivatives of trimethylolpropane are examples of this class of materials.

14. Polyhydric alcohol esters. Ethylene glycol mono- and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters for use herein.

15. Wax esters such as beeswax, spermaceti, myristyl myristate, stearyl stearate.

16. Beeswax derivatives, e.g. polyoxyethylene sorbitol beeswax. These are reaction products of beeswax with ethoxylated sorbitol of varying ethylene oxide content, forming a mixture of ether-esters.

17. Vegetable waxes including carnauba and candelilla waxes.

18. Phospholipids, such as lecithin and derivatives.

19. Sterols. Cholesterol and cholesterol fatty acid esters are examples thereof.

20. Amides such as fatty acid amides, ethoxylated fatty acid amides, solid fatty acid alkanolamides.

Particularly useful emollients which provide skin conditioning are glycerol, hexanetriol, butanetriol, lactic acid and its salts, urea, pyrrolidone carboxylic acid and its salts, amino acids, guanidine, diglycerol and triglycerol. Preferred skin conditioning agents are the propoxylated glycerol derivatives.

Utility, Testing and Administration

The compounds of the invention, antioxidant salen-transition metal complexes, preferably salen-Mn complexes, are useful treatments for protection against ischemic damage in cardiac and non-cardiac states including myocardial infarction, congestive heart failure, angina, arrhythmia, circulatory disorders, and stroke. The compounds of the invention inhibit the deleterious effects of ischaemia (coronary infarction and reperfusion in the heart; transient myocardial or CNS ischemia during surgery) without direct depressant effects on myocardial contractility. Thus, the compounds are effective in animal models for cardiovascular and CNS diseases, and will be useful for the treatment of myocardial infarction, stroke, brain injury, and transplant surgery, particularly with reperfusion of infarcted areas, arrhythmias, variant and exercise-induced angina, congestive heart failure, stroke and other circulatory disorders, in mammals, particularly in human beings. The salen-Mn complexes are also included in preservation solutions used to bathe excised organs (e.g., heart, kidney, pancreas, liver, lung) during transport and storage of the excised organ prior to transplantion surgery, including skin grafting and corneal grafting. The preservation solutions will typically comprise at least about 1 $\mu$M of an antioxidant salen-metal complex, preferably at least about 1 mM of an antioxidant salen-metal complex.

Administration of the active compound and salts described herein can be via any of the accepted modes of administration for therapeutic agents. These methods include oral, parenteral, transdermal, subcutaneous and other systemic modes. The preferred method of administration is oral, except in those cases where the subject is unable to ingest, by himself, any medication. In those instances it may be necessary to administer the composition parenterally. If the composition comprises an antioxidant salen-metal species having an amino substituent that can be protonated at physiological pH, it is usually preferred that the antioxidant salen-metal complex is dissolved or suspended in a solution having a pH at which the amino substituent is protonated.

The amount of active compound administered will, of course, be dependent on the subject being treated, the subject's weight, the severity of the affliction, the manner of administration and the judgment of the prescribing physician. However, an effective dosage is in the range of 0.01–50 mg/kg/day, preferably 0.5–25 mg/kg/day. For an average 70 kg human, this would amount to 0.7–3500 mg per day, or preferably about 35–1750 mg/day.

Since all of the effects of the salen-Mn compounds herein are achieved through a similar mechanism, dosages (and forms of administration) are within the same general and preferred ranges for all these utilities.

The following examples are offered by way of illustration, not by way of limitation.

EXPERIMENTAL EXAMPLES

EXAMPLE 1

In Vitro Catalytic Activities

The antioxidant catalytic activities of the $C_1$, C4, C6, C7, C9, C10, C11, and C12 salen-Mn complexes (see FIG. 3) was determined; superoxide dismutase and catalase activities were determined according to the following method.

Assay

The SOD activity of the compounds was determined by evaluating the inhibition of the reduction of cytochrome C produced by the oxygen free radical generating system, xanthine plus xanthine oxidase. Cytochrome C reduction is monitored spectrophotometrically at 550 nm according to the method described in Darr et al. (1987) *Arch. Biochem. Biophys.* 258: 351, incorporated herein by reference. The concentration of xanthine oxidase is adjusted such that it produces a rate of reduction of cytochrome C at 550 nm of 0.025 absorbance unit per minute. Under these conditions, the amount of SOD activity required to inhibit the rate of cytochrome C reduction by 50 percent (i.e., to a rate of 0.0125 absorbance unit per minute) is defined as one unit of activity. Salen-metal complexes are identified as antioxidants if they have at least 0.1 unit of activity at a concentration of 1 mM under these standard assay conditions.

Catalase activity was measured using a spectrophotometric method in which the decomposition of hydrogen peroxide is monitored at 240 nm according to the method of Aebi et al. (1984) *Methods Enzymol.* 105: 121, incorporated herein by reference. One unit of catalase activity is defined as the amount of enzyme (or salen-metal complex) required to decompose 1 μmole of hydrogen peroxide in one minute.

Each of the compounds was formulated in saline and was stable with no loss of activity observed after several weeks of storage at room temperature. Frequently, it is desirable to first dissolve the salen-metal complex in an organic solvent (e.g., DMSO) and then dilute the solution into a more polar solvent such as water. This is particularly preferred for salen-metal species that are relatively hydrophobic (e.g., C12).

Table IV shows the in vitro SOD and catalase activities of the various salen-Mn complexes tested. SOD and catalase activities are expressed as units/mM.

TABLE IV

| Salen-Mn Complex | SOD Activity | Catalase Activity |
|---|---|---|
| C1 | 308 | 262 |
| C4 | 312 | 200 |
| C6 | 812 | 0 |
| C7 | 575 | 200 |
| C9 | 111 | 20 |
| C10 | 69 | 179 |
| C11 | 101 | 46 |
| C12 | 4397 | 144 |

In Vivo Biological Activities

A widely used assay to determine the therapeutic potential of molecules in brain ischemia (stroke) consists of evaluating their ability to prevent irreversible damage induced by an anoxic episode in brain slices maintained under physiological conditions. Rat brain slices were maintained at 35° C. in an interface chamber in an artificial cerebrospinal fluid containing: 124 mM NaCl, 3 mM KCl, 1.25 mM $KH_2PO_4$, 3 mM CaCl, 1 mM $MgCl_2$, 26 mM $NaHCO_3$, 10 mM D-glucose, and 2 mM L-ascorbate, continuously gassed with a mixture of $O_2:CO_2$ (95:5). The atmosphere of the chamber was also continuously gased with the mixture of $O_2:CO_2$ (95:5), except during the anoxic episode when it was replaced by $N_2$. Axons were electrically stimulated and the evoked excitatory post-synaptic potentials (EPSPs) were recorded using microelectrodes.

Figure 4:
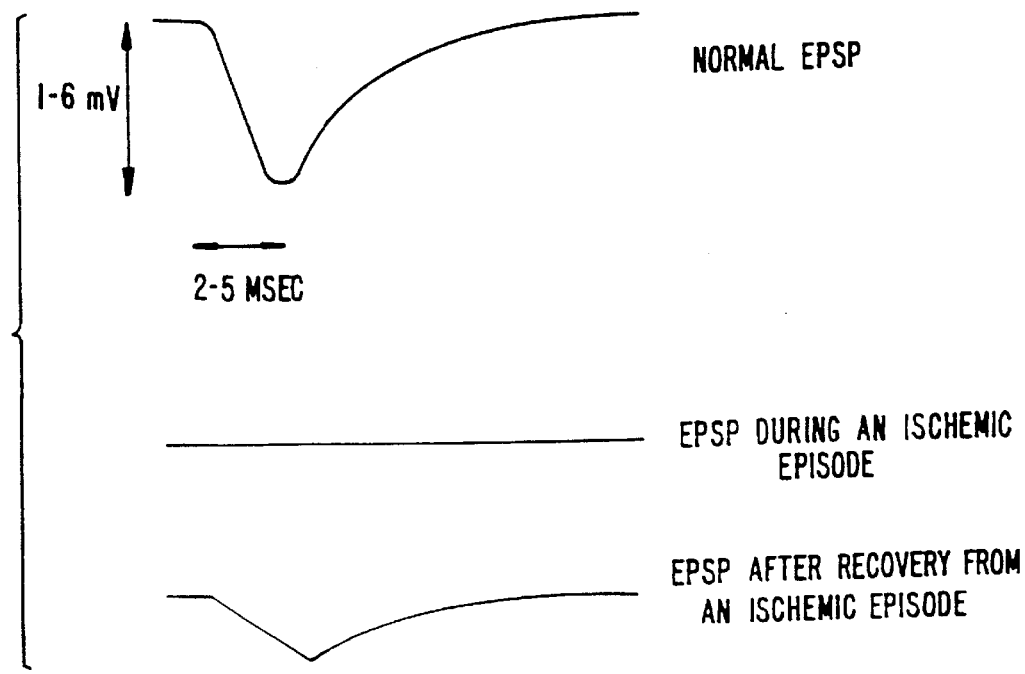
FIG. 4 shows schematically the effect of an ischemic/reoxygenation episode on synaptic transmission in isolated brain slices.

FIG. 4 shows the schematic of an EPSP recorded under normal conditions (A), five minutes following replacement of $O_2$ with $N_2$ (ischemic episode, B), and 30 to 40 minutes following reoxygenation (C). The extent of permanent damage can be quantified by measuring both the amplitude (in mV) and the initial slope (in mV/msec) of the EPSP.

Figure 5:
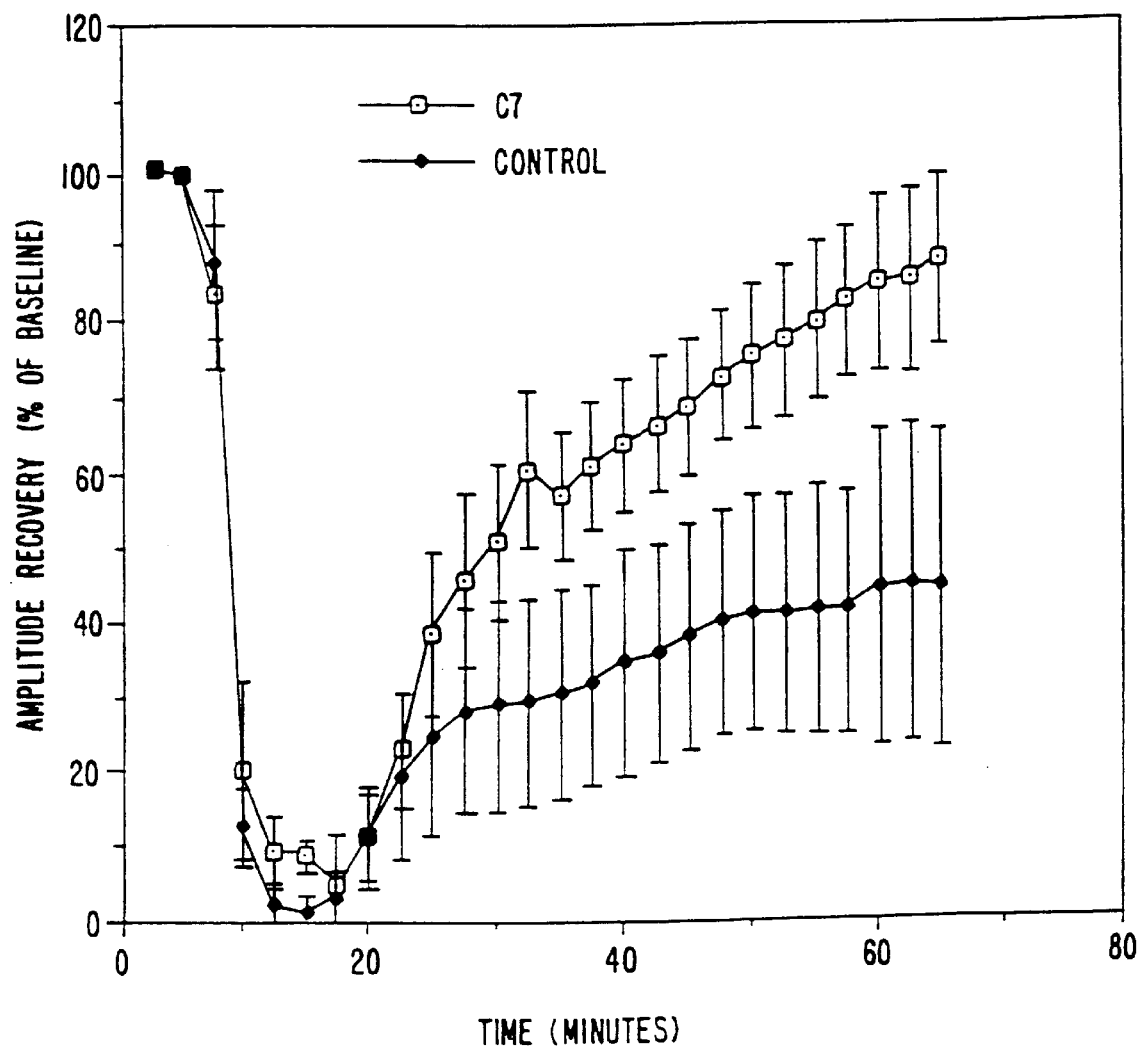
FIG. 5 shows the effect of a salen-Mn complex on EPSP amplitude following an episode of ischemia/reoxygenation.
Figure 6:
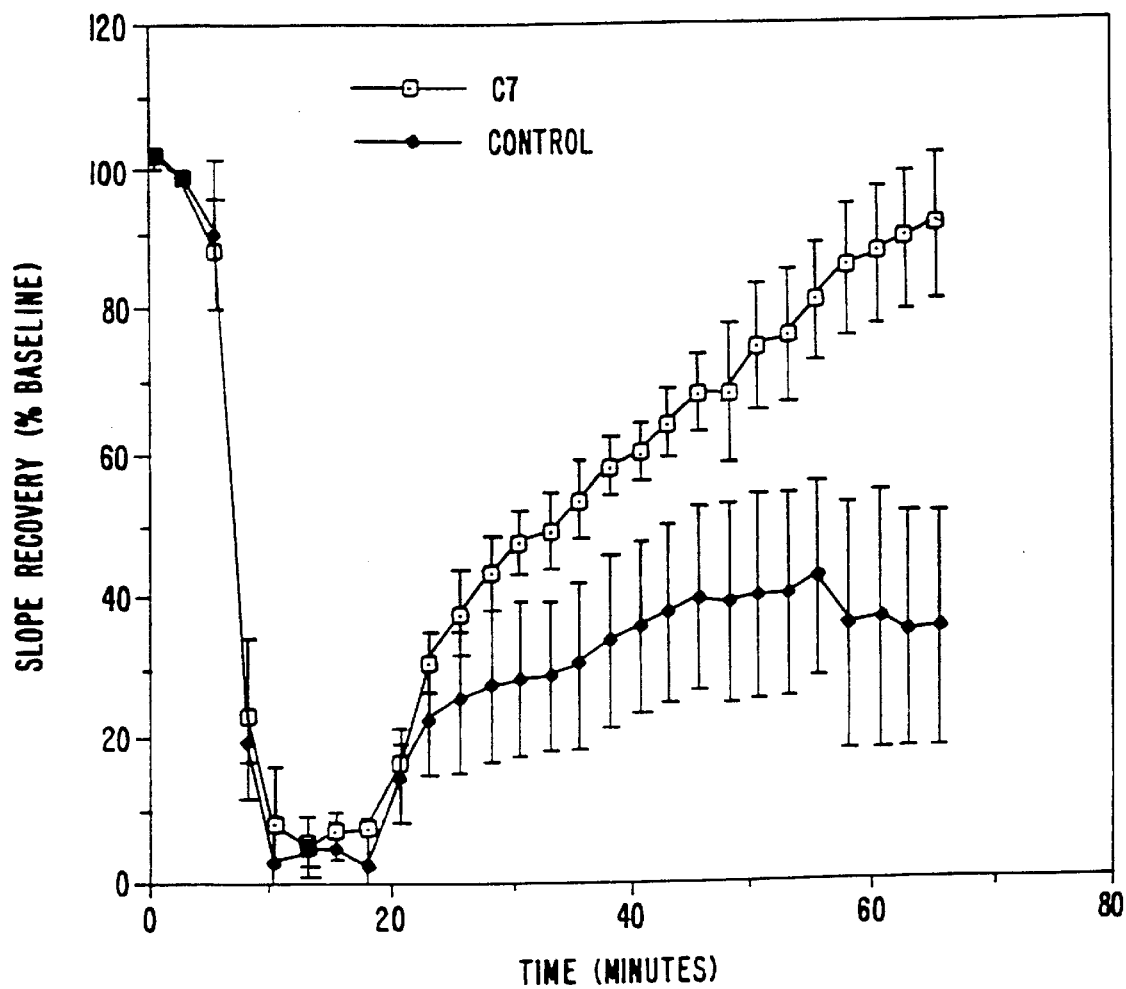
FIG. 6 shows the effect of a salen-Mn complex on EPSP initial slope following an episode of ischemia/reoxygenation.

FIGS. 5 and 6 show the protective effect of the antioxidant salen-Mn complex designated C7 in the rat brain slice ischemia EPSP system. Brain slices were incubated in the absence or presence of 50 μM C7 and subjected to an episode of ischemia/reoxygenation. After 5 minutes of baseline recording, $O_2$ was replaced by $N_2$ for an average of 5 minutes. $O_2$ was then reintroduced and recording was continued for another 50 minutes. Samples with 50 μM C7 showed that both the amplitude and slopes of the EPSPs recovered to pre-ischemia levels. in contrast, recovery in untreated brain slices was only about 40% of pre-ischemia levels.

Figure 7:
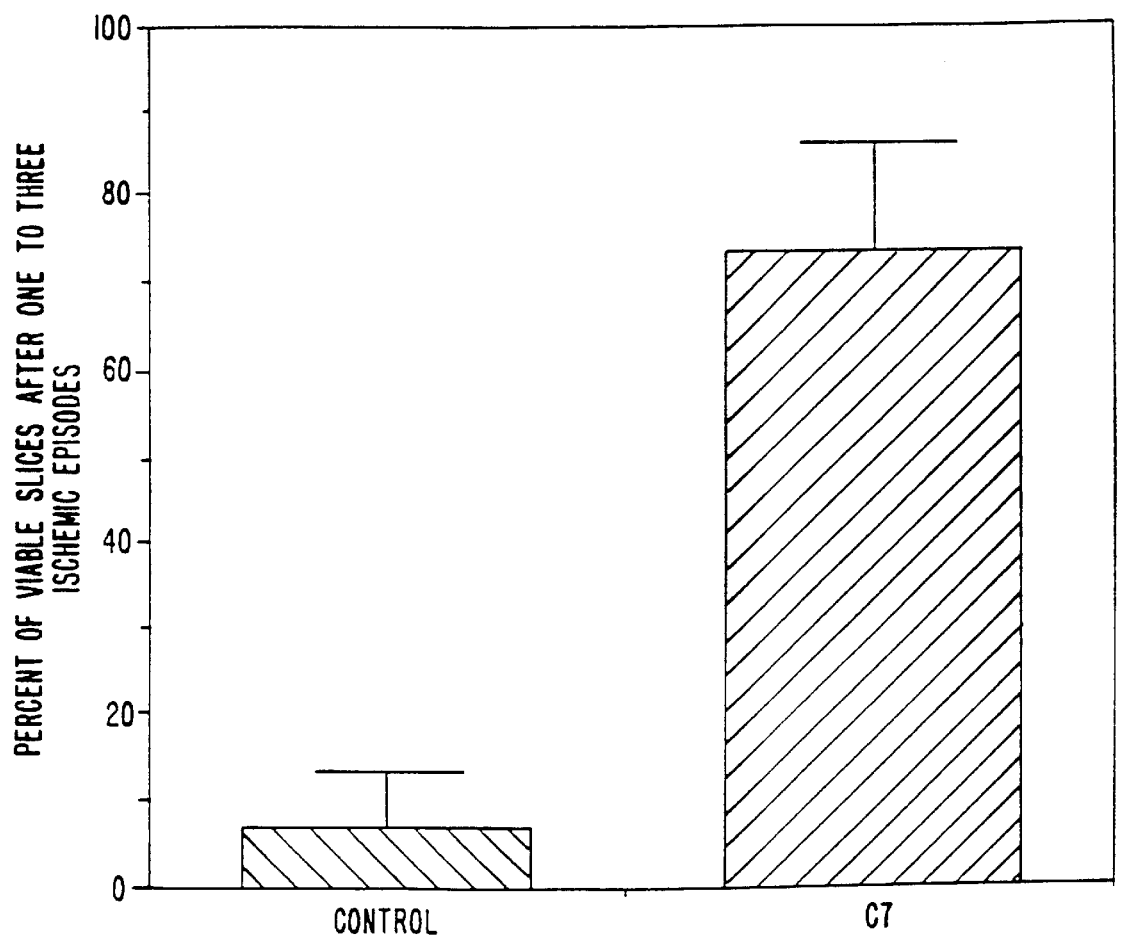
FIG. 7 shows the effect of a salen-Mn complex on brain slice viability following repeated episodes of ischemia/reoxygenation.

As an additional assessment of efficacy, the percentage of viable slices following repeated ischemic episodes was evaluated. FIG. 7 demonstrates that, while without any treatment this percentage is very low (6%), it was as high as 70% in slices treated with 50 μM C7. A slice was considered viable if an EPSP of 3 mV amplitude could be elicited by increasing stimulation intensity.

Animal Model Testing

An animal model of Parkinson's disease involving iatrogenic hydroxyl radical generation by MPTP (Chiueh et al. (1992) *Synapse* 11: 346, incorporated herein by reference) was used to evaluate the protective effect of C7 on free radical-induced damage. The neurotoxin, MPTP, has been shown to lead to the degeneration of dopaminergic neurons in the brain, thus providing a good model of experimentally induced Parkinson's disease (e.g., iatrogenic toxicity). This model is now widely accepted in the art and is used for evaluating potential therapeutic agents for this disease.

Figure 8A:
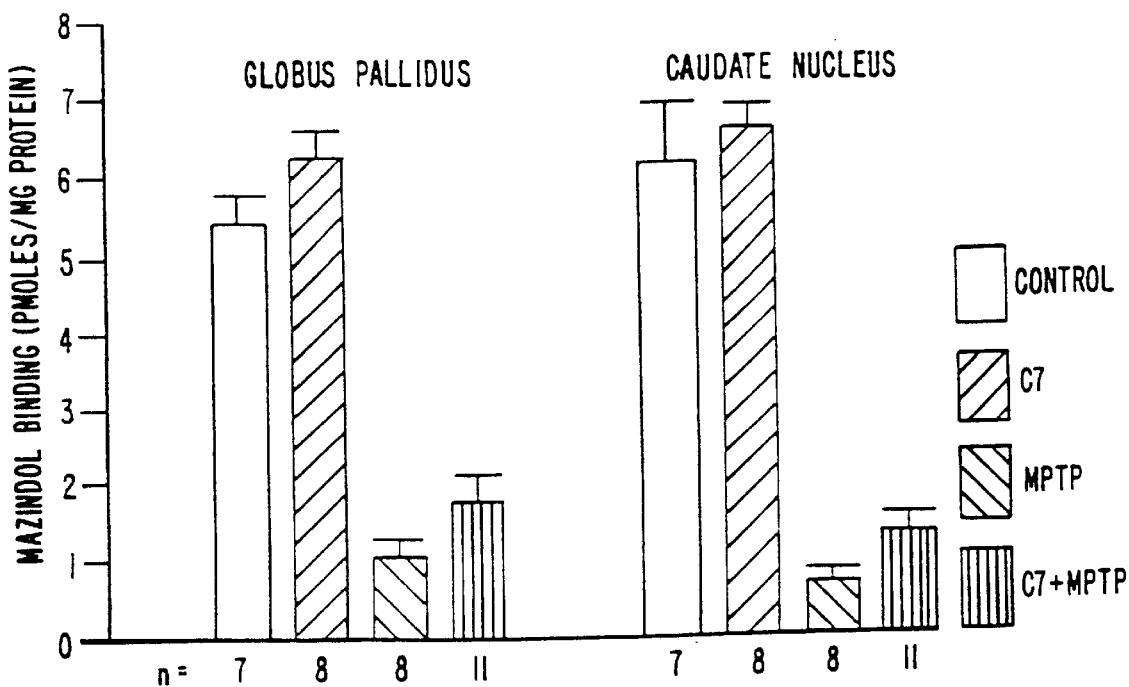
FIGS. 8A and 8B show the protective effect of a salen-Mn complex in an animals model of iatrogenic Parkinson's disease.
Figure 8B:
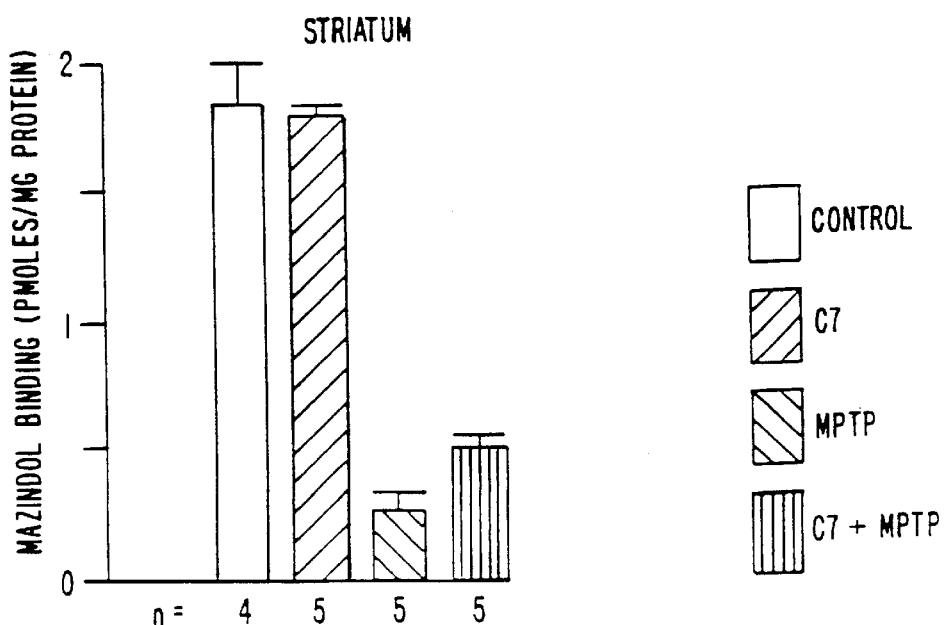

The number of dopaminergic neurons in brains of mice treated with either: (1) MPTP alone, (2) the antioxidant salen-metal complex C7 alone, (3) pretreatment with C7 and then MPTP, or (4) untreated controls, were assayed by measurement of the binding of the dopamine reuptake 1ligand, mazindol. Tritiated mazindol was used for binding studies on samples of the globus pallidus, caudate nucleus, and striatum of mouse brain according to conventional methods; specific binding of tritiated mazindol was determined autoradiographically or by membrane binding (specific binding to the membrane fraction). The experiment was performed over a 7 day period. Mice in the MPTP group were treated intraperitoneally with MPTP alone (40 mg/kg each day on days 1 and 2). Mice in the MPTP+C7 group were pretreated with C7 (33 mg/kg, i.p.) immediately prior to MPTP on days 1 and 2, and were given C7 (33 mg/kg) alone on day 3. The animals were sacrificed after 7 days. The results shown in FIG. 8 show a significant protective effect conferred in vivo by the salen-Mn complex, C7. FIG. 8 shows that the number of dopaminergic neurons present in various regions of the mouse brain were not adversely affected by the antioxidant salen-metal complex C7; but dopaminergic neurons were reduced to about 15 percent of control values in mice treated with MPTP alone; however pretreatment with C7 approximately doubled the number of surviving dopaminergic neurons present in mice subsequently treated with MPTP. Lack of toxicity of C7 was shown by the absence of adverse health effects in the C7-treated animals over the 7 day test period.

These data demonstrate that the salen-Mn complexes display therapeutic efficacy in vivo in rodent models of human disease. and also indicate that the salen-Mn complexes cross the blood-brain barrier efficiently. Taken together, these data indicate a dramatic efficacy of salen-Mn complexes to prevent free radical-induced damage and ischemia/reoxygenation injury in the brain.

Effect of C7 in Isolated Iron-overloaded Rat Hearts Submitted to Ischemia and Reperfusion Rats received an intramuscular injection of 0.25 ml of an iron-dextran solution (100 g iron hydroxide, 99 g dextran, water up to 11) every third day during a 5-week period to achieve a significant iron overload in cardiac tissue. At the end of this treatment, rats were anesthetized with sodium pentobarbital (40 mg/kg) and heparin (1,000 IU/kg) was administered via a femoral vein. Hearts were then removed and rapidly perfused through the aorta according to the technique described by Langendorff [Langendorff, O., *Pflügers Arch.* 61: 291, 1895] at a constant flow rate of 11 ml/minute. The perfusion fluid was a modified Krebs-Henseleit buffer containing (in mmol/l): NaCl 118, KCl 5.9, $NaHCO_3$ 25, $MgCl_2$ 1.2, $NaH_2PO_4$ 0.6, $CaCl_2$ 2.4, Glucose 11. pH was maintained at 7.4±0.05 when the perfusion medium was saturated with $O_2$—$CO_2$ (95%–5%) at 37° C. The perfusion apparatus was fully thermostated such that the temperature of the perfusion medium was 37.0±0.5° C. when it reached the aorta. An ultra-thin balloon was inserted in the left ventricle immediately after the initiation of aortic perfusion and was inflated so as to obtain an end-diastolic pressure of 5 mm Hg. A 15 minute stabilization period was initiated immediately following balloon placement. At the end of this period, systolic and diastolic ventricular pressures and heart beat rate (HR) were recorded through a pressure transducer linked to the ventricular balloon. Left Ventricular Developed Pressure (LVDP) was calculated by the difference between systolic and diastolic pressure and the product HR x LVDP was taken as an index of oxygen consumption. Hearts were then subjected to a 15 minute total global normothermic ischemia, followed by 15 minutes of reperfusion with the perfusion medium used initially. During this 15 minute reperfusion, heart rate, and diastolic and systolic pressures were monitored. Early ventricular fibrillations were analyzed 1 min. after the start of the reperfusion.

Three experimental groups were studied. Group 1 (n=7) in which hearts were perfused with the standard perfusion fluid (control group); group 2 (n=8) were perfused in the presence of dimethylthiourea (DMTU, 10 mM; group 3 (n=8) were perfused in the presence of C7 (50 µM).

After the 15 minute reperfusion, 3 hearts in each group were prepared for electron microscopy by perfusion with 2.5% glutaraldehyde. Ultra-thin slices (500–600 Å thickness) were examined.

Results

The following Table V shows heart rates (HR), systolic pressures (SP), diastolic pressures (DP), and the products HR x LVDP, in the three experimental groups, after 15 minutes of perfusion, before ischemia (Before), 1 minute after reperfusion (1 After) and 15 minutes after reperfusion (15 After). The table also shows the number of hearts exhibiting episodes of ventricular fibrillation 1 minute after reperfusion (VF).

TABLE V

| | HR (beats/min) | SP (mm Hg) | DP (mm Hg) | HR x LVDP (x10.3) | VF |
|---|---|---|---|---|---|
| Controls: | | | | | |
| Before | 276 ± 11 | 78 ± 7 | 6.3 ± 0.3 | 19.6 ± 1.6 | — |
| 1 After | 96 ± 0 | 40 ± 6 | 23.3 ± 6.0 | 4.2 ± 1.7 | 5/7 |
| 15 After | 232 ± 15 | 62 ± 10 | 13.6 ± 4.2 | 12.6 ± 2.3 | — |
| +DMTU | | | | | |
| Before | 280 ± 10 | 97 ± 4 | 4.7 ± 0.3 | 24.1 ± 0.6 | — |
| 1 After | 91 ± 10 | 62 ± 9* | 37.2 ± 10.0 | 3.5 ± 1.2 | 3/8 |
| 15 After | 226 ± 18 | 58 ± 6 | 27.8 ± 9.4 | 9.4 ± 2.0 | — |

TABLE V-continued

| | HR (beats/min) | SP (mm Hg) | DP (mm Hg) | HR x LVDP (x10.3) | VF |
|---|---|---|---|---|---|
| +C7 | | | | | |
| Before | 278 ± 7 | 90 ± 2 | 5.4 ± 0.3 | 23.5 ± 0.9 | — |
| 1 After | 130 ± 13# | 72 ± 8# | 5.8 ± 0.5#± | 9.9 ± 0.8#± | 2/8 |
| 15 After | 241 ± 15 | 92 ± 15 | 8.3 ± 0.6 | 21.7 ± 3.4¤± | — |

*: p < 0.01, DMTU versus control at the same time.
: p < 0.01, C7 versus control at the same time.
¤: p < 0.05, C7 versus control at the same time.
±: p < 0.01, C7 versus DMTU at the same time.

microscopy evaluation of the hearts. Mitochondria were classified into Type A (normal), Type B (swollen, unbroken), and Type C (ruptured membranes). Sarcomeres were classified into Type A (normal) and Type B (contacted and/or necrosis). The results are expressed as percentages. The numbers of mitochondria analyzed were 1293, 1632 and 1595 for controls, DMTU and C7 groups, respectively. The numbers of sarcomeres analyzed were 1046, 1173, and 1143 for controls, DMTU and C7 groups, respectively.

TABLE VI

| | Mitochondria | | | Sarcomeres | |
|---|---|---|---|---|---|
| | Type A | Type B | Type C | Type A | Type B |
| Controls | 10.4 | 21.0 | 68.5 | 21.3 | 78.7 |
| +DMTU | 14.3# | 19.5 | 66.2 | 13.7± | 86.3± |
| +C7 | 31.0#± | 15.2#¤ | 53.8#± | 60.6#± | 39.4#± |

*: p < 0.05, DMTU versus control.
+: p < 0.01, DMTU versus control.
: p < 0.01, C7 versus control.
¤: p < 0.05, C7 versus DMTU.
±: p < 0.01, C7 versus DMTU.

The data show that C7 effectively protected hearts from ischemia/reoxygenation damage, both functionally and structurally. In addition, C7 was significantly more efficacious than DMTU, an antioxidant, even though it was used at a concentration 200 times lower.

Experimental Autoimmune Encephalitis (EAE)

EAE is an animal model of multiple sclerosis. 30 SJL female mice, aged 10 weeks, were divided into 2 groups of 20 mice (control) and 10 mice (C7 treated).

Mice in both groups were immunized with an encephalitogenic PLP peptide in complete Freund's adjuvant subcutaneously, followed by Petrussis Toxin (IV). Petrussis toxin was repeated on day 3 post immunization.

Mice in the C7 group were treated daily (1 mg/mouse, approximately 40 mg/kg) by IP injection, starting from 2 days prior to immunization through day 14 after immunization.

Animals were scored as follows:

Stage I: Limp tail syndrome

Stage II: Hind leg paralysis

Stage III: Hind leg paralysis-Dragging movement

Stage IV: Paralytic immobility, weight loss

Results

During the third week following immunization, 8 of 20 mice in the control group developed symptomatic EAE: 2 Stage I, 4 Stage II/III, 2 Stage IV.

During that same period, only one of 10 mice in the C7 treated group developed symptomatic EAE (Stage II).

During the fifth week, i.e., three weeks after the treatment with C7 was stopped, six mice in the C7 group developed symptomatic EAE, 4 Stage II and 2 Stage IV.

These results indicate that C7 treatment prevented the development of symptomatic EAE, and that the disease could develop following interruption of the treatment.

Acute Lung Injury in Endotoxemic Pigs

Reactive oxygen metabolites (ROM's) are important mediators of acute lung injury (ALI) in sepsis and endotoxemia. When treatment with C7 is begun prior to lipopolysaccharide (LPS;endotoxin) infusion, this agent prevents many of the manifestations of LPS-induced ALI in pigs. Treatment with C7 after LPS administration was determeined to afford protection against endotoxin-induced ALI in pigs.

Materials and Methods

All pigs were pre-treated at T=−18 h with *Escherichia coli* 0111:B4 LPS (20 µg/kg). Pigs in the RL group (n=4) received no further treatment. From T=0 to 60 min, pigs in both the LPS (n=5) and LPS/C7 (n=6) groups were challenged with LPS (250 µg/kg). Immediately following the completion of LPS infusion, beginning at T=60 min, pigs in the LPS/C7 group received a bolus dose of C7 (10 mg/kg in 5% dextrose) followed by a continuous infusion (10 mg/kg-h). Lung wet-to-dry weight ratio was determined postmortem. Lung lipid peroxidation was estimated fluorometrically by measuring thiobarbituric acid reactive products in the lipid fraction of lung parenchymal tissue harvested at T=300 min.

Results

Infusion of endotoxin resulted in pulmonary arterial hypertension, arterial hypoxemia and decreased dynamic pulmonary compliance. LPS also increased lung water and lung lipid peroxidation (Table X). Delayed treatment with C7 attenuated many of the physiologic derangements caused by the infusion of endotoxin in pigs.

TABLE X

|  | RL(n = 4) | LPS(n = 5) | LPS/EUK-8(n = 6) |
|---|---|---|---|
| $P_{pa}$ | 16 ± 1 | 34 ± 3 | 25 ± 3 |
| $PaO_2$ | 171 ± 13 | 83 ± 16 | 148 ± 22 |
| %$C_{dyn}$ | 82 ± 3 | 47 ± 4 | 78 ± 4 |
| W/D | 5.9 ± 0.1 | 7.7 ± 0.4 | 6.4 ± 0.4 |
| MDA | 52 ± 12 | 398 ± 51 | 180 ± 27 |

Table 1. Effects of LPS with and without EUK-8 in anesthetized, ventilated swine. Pigs received Ringer's lactate (15 ml/kg-h from T = 0 – 300 min) and dextran-70 titrated to maintain cardiac output at 90–100% of the baseline value for each animal. Data are reported as means ± SE. All values presented are at T = 300 min. $P_{pa}$ = mean pulmonary arterial pressure (mm Hg); $PaO_2$ = arterial oxygenation (mm Hg); % $C_{dyn}$ = dynamic pulmonary compliance; W/D = lung wet-to-dry weight ratio; and MDA = lung malondialdehyde level (pmols/mg dry weight). Between group contrasts were assessed by ANOVA and Student-Newman-Keuls test. Within-group differences compared to baseline values (T = 0 min) were evaluated using Dunnett's method. $^1P$ < 0.05 vs. baseline value. *P < 0.05 vs. LPS. P < 0.05 vs. RL.

Conclusions

Even when administered 60 min after the onset of endotoxemia, C7 protects against many of the deleterious effects of endotoxin in this stringent model of ALI. These data support the further development of synthetic catalytic ROM scavengers for the treatment of sepsis-induced ALI in humans.

Lipid peroxidation

Hippocampal slices (400 µm thick) were obtained from Sprague-Dawley rats (150–200 g) and collected in preoxygenated (95% $O_2$/5% $CO_2$) Krebs-Ringer phosphate medium (pH 7.4) containing NaCl 120 mM, KCl 5 mM, $CaCl_2$ 1.3 mM, $MgCl_2$ 1.2 mM, NaPhosphate 16 mM (pH 7.4) and glucose 10 mM. After 15 minutes preincubation in a water bath at 35° C. under agitation, the buffer was replaced with the same buffer (control) or a modified buffer (lactate buffer) containing NaCl 90 mM, KCl 5 mM, $CaCl_2$ 1.3 mM, $MgCl_2$ 1.2 mM, NaPhosphate 16 mM and lactic acid 30 mM (pH 5.0). When present, C7 (50 µM) was added during the preincubation and the incubation periods. After 100 minutes, slices were collected and homogenized in 0.9 ml of TCA 5%, whereas 0.35 ml of TCA 5% was added to 0.5 ml of the incubation medium. Lipid peroxidation was measured by adding 0.25 ml of a thiobarbituric acid reagent (TBAR) to 0.85 ml of the TCA extracts and incubating the mixture for 60 minutes at 85–93° C. Lipids were then extracted with 2×0.5 ml 1-butanol by vortexing for 10 seconds, then centrifuging at 2,000 rpm for 10 minutes. The absorbance of peroxidized lipids in the alcohol phase was measured in a spectrophotometer at 532 nm. Data were expressed as nmoles of malondialdehyde (MDA) using authentic MDA to establish a standard curve. Proteins were measured from an aliquot of the TCA extracts using the method of Bradford and the final results were calculated as nmoles MDA formed/mg protein.

Results

Figure 9:
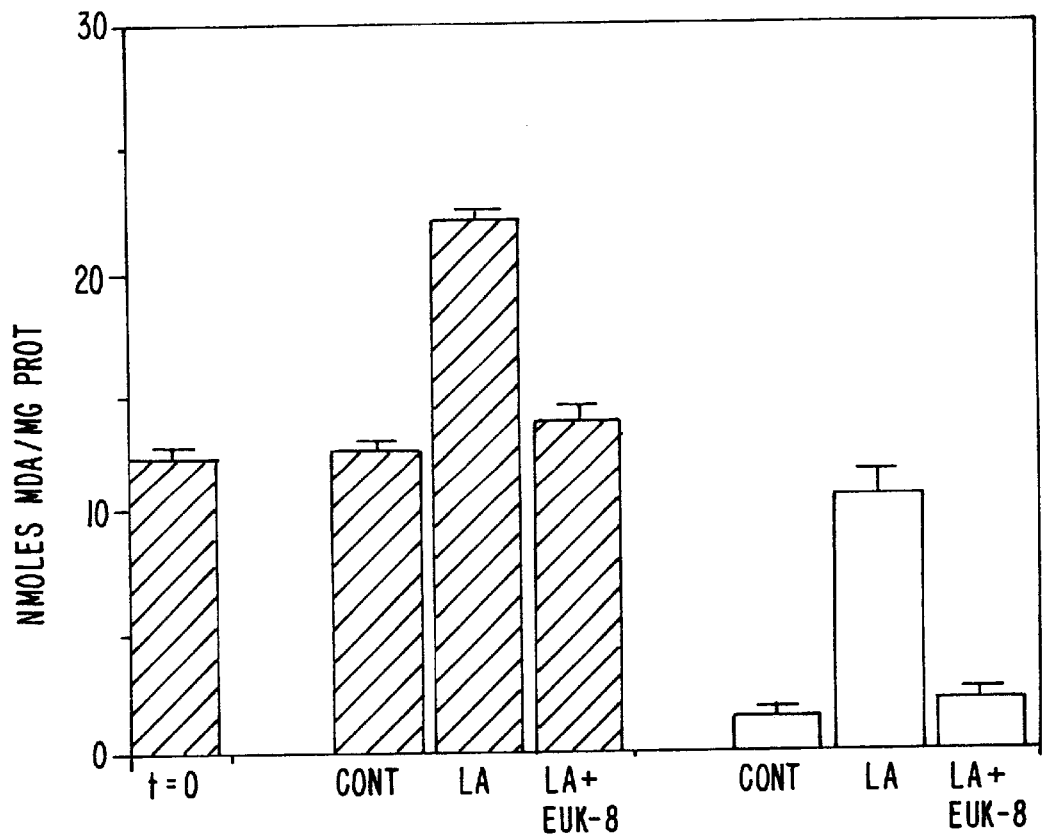
FIG. 9 shows that C7 protects hippocampal slices from lactic acid-induced lipid peroxidation.

The FIG. 9 shows lipid peroxidation at time 0 (immediately after sectioning), and after 100 minutes of incubation at pH 7.4 (control), at pH 5.0 (lactate) in the absence (LA) or presence (LA+C7) of 50 µM C7, in the slice homogenates (hatched bars) and in the incubation medium dotted bars). Data are means±S.D. and the C-7 experimental group were highly statistically significant as compared to control (p<0.01) while the small differences between LA and LA+C7 are not. Incubation of hippocampal slices with 30 mM lactate, at a final pH of 5.0, resulted in a large increase in lipid peroxidation, as measured by the thiobarbituric acid test. Incubation of slices with C7 (50 µM) totally abolished the increase in lipid peroxidation. Lactate-induced increases in malondialdehyde concentration in both the incubation media (dotted bars) and in the slice homogenates (hatched bars) were blocked by C7. Incubation for 100 minutes without lactate, either with or without C7, did not cause any appreciable increase in lipid peroxidation.

These data show that C7 prevents lipid peroxidation induced by acidosis. Acidosis is known to induce extensive oxidative damage. Lipid peroxidation is a consequence of such oxidative damage, and has been found associated with a number of human pathologies.

In vitro models of injury

Anoxia in hippocampal slices. Electrophysiological experiments were performed on hippocampal slices (400 µm) from adult Sprague-Dawley rats maintained at 35° C. in 2 interface chambers with or without 50 mM C7. A glass recording micropipet was positioned in CA1 stratum radiatum to record excitatory postsynaptic potential (EPSPs) generated by electrical stimulation of the Schaffer-commissural pathway by a bipolar stimulation electrode at a frequency of 0.033 Hz. During anoxic episodes, the oxygen supply was replaced with 100% $N_2$ gas. $N_2$ was supplied for 90 seconds following electrical silence after which $O_2$ was reintroduced. Recovery of EPSPs (both slope and amplitude) was recorded for 50 minutes, at which time the final viability of the slices was determined, with viability being defined as the ability of the slice to generate a 3 mV EPSP.

Acidosis in hippocampal slices. Hippocampal slices were collected in preoxygenated Krebs-Ringer phosphate buffer, with or without 50 $\mu$M C7, at 35° C. in a shaking water bath. After a 15 minute preincubation, slices were transferred into the same buffer or in a buffer containing 30 mM lactate, pH 5.0 (with or without C7). Slices from all groups were collected after a 100 minute incubation and tested for lipid peroxidation, as indicated by malondialdehyde reaction with thiobarbituric acid.

In Vivo Model of Neuronal Injury

MPTP in mice. Adult male CFW mice (25–33 g) were administered two injections of MPTP dissolved in normal saline (40 mg/kg, s.c.) 24 hours apart. A group of animals also received C7 in three injections (33 mg/kg, s.c.) administered 24 hours apart, starting 1 day before the onset of MPTP treatment. Animals were sacrificed 7 days after the first MPTP injection, and neuronal pathology was assessed by the binding of $^3$H-mazindol, a ligand for the dopamine transporter, to 10 mm frozen brain sections or to striatal homogenates.

6-OHDA in mice. Adult male CFW mice were anesthetized with ketamine and rumpun, and immobilized in a stereotaxic device. 6-OHDA, as the hydrobromide salt, was dissolved in normal saline with 1% ascorbate, and 50 $\mu$g was administered in lateral ventricle by means of a 10 $\mu$l Hamilton syringe. C7 (66 mg/kg, i.p.) was administered daily for 4 days. Animals were sacrificed 7 days later, and neuronal pathology was assessed by measuring $^3$H-mazindol binding in striatal homogenates.

Results

C7 Protects Hippocampal Slices from Anoxia-induced Damage

Hippocampal slices were subjected to anoxic conditions with or without C7 (50 $\mu$M). C7 provided a significant degree of protection against anoxia-induced decrease in synaptic response in CA1. The decrease in both EPSP slope (A) and amplitude (B) were prevented by C7. Purified bovine SOD in the same assay provided no protection).

Figure 10:
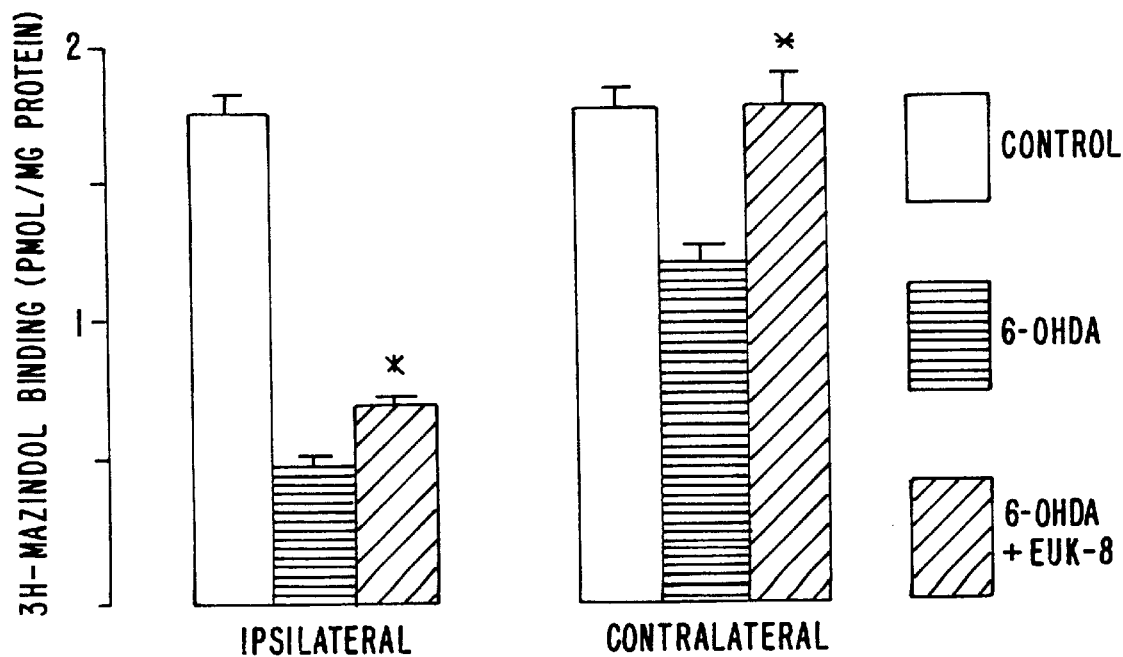
FIG. 10 shows C7 protects dopaminergic neurons in mouse striatum from 6-OHDA-induced degeneration.
Figure 11A:
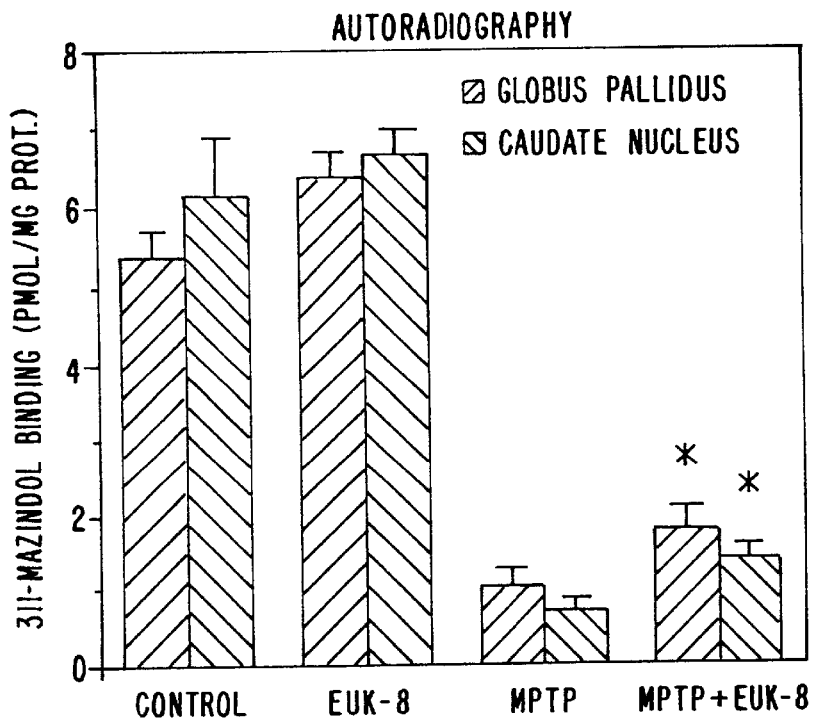
FIGS. 11A and 11B shows C7 protects dopaminergic neurons in mouse striatum from MPTP-induced degeneration.
Figure 11B:
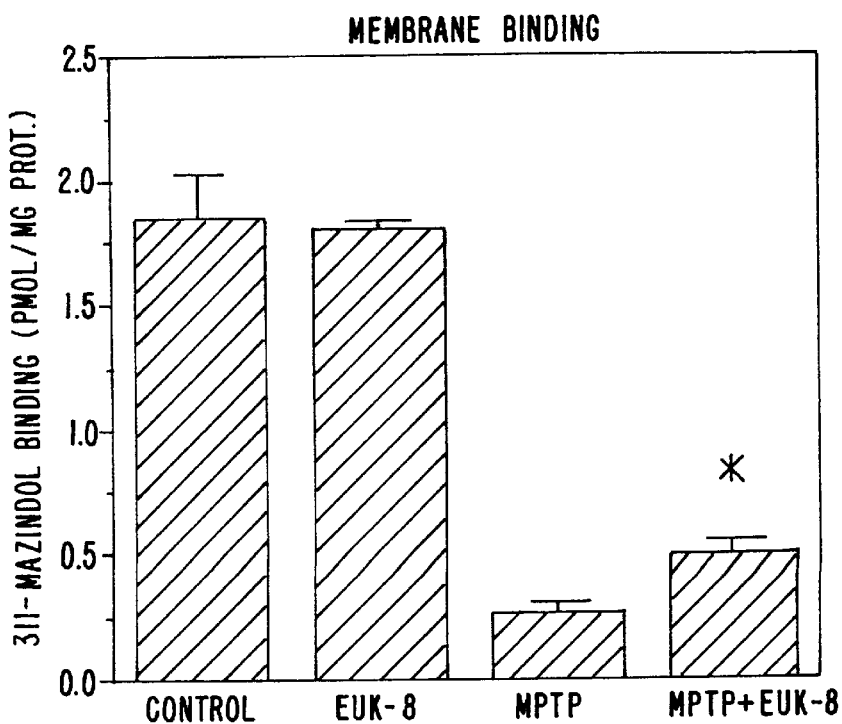

FIG. 10 shows I.c.v. injection of 6-OHDA (50 $\mu$g) resulted in a 60–70% decrease in mazindol binding in homogenates from the striatum ipsilateral from the injection site and a 30% decrease from the contralateral striatum (FIG. 10). Treatment with C7 (4×66 mg/kg) produced a significant reduction in the ipsilateral side and a complete protection in the contralateral side.

MPTP administration (2×40 mg/kg, s.c.) resulted in a 75–80% decrease in mazindol binding. C7 treatment (3×33 mg/kg, i.p.) caused a significant ($p<0.05$) degree of protection against the reduction in $^3$H-mazindol binding in both the globus pallidus, and the caudate nucleus (panel A). C7 treatment alone had no significant effect on $^3$H-mazindol binding. The same treatment also produced a significant protection against the reduction in 3H-mazindol binding measured in striatal homogenates (panel B).

Conclusions

These results illustrate the protective effects of a Synthetic Catalytic Scavenger (SCS), C7, in various models of neuronal damage. C7 was able to protect neurons from acute early manifestations of neuronal damage, such as lipid peroxidation and loss of synaptic viability, as well as long-term manifestations of neuronal injury, such as neuronal loss 7 days after toxin injection.

In view of the positive effects obtained with peripheral injections of C7 in the in vivo models of neuronal injury, we conclude that the complex is stable in vivo and crosses the blood brain barrier as well as neuronal membranes.

The positive effects of C7 in various models of neuronal injury indicate that reactive oxygen species, especially the superoxide radical, play a significant role in the pathology induced by ischemia and acidosis, and in MPTP- and 6-OHDA-induced loss of nigrostriatal dopaminergic neurons.

Finally, in view of the wide range of pathological conditions associated with overproduction of oxygen radicals, these results support the idea that antioxidant salen-metal complexess such as C7 might have a wide range of therapeutic applications.

EXAMPLE 2

Salen-metals as SOD/Catalase/Peroxidase Mimetics

Overview

Synthetic catalytic scavengers of reactive oxygen species (ROS) may have clinical value in alleviating tissue damage associated with numerous acute and chronic diseases. Example 1 demonstrates that synthetic salen manganese complexes have superoxide dismutase (SOD) activity. One of these compounds, C7, has been found to be protective in several models for ROS-associated tissue injury. In this example, the catalytic properties of C7, in particular, are further characterized demonstrating that it also utilizes hydrogen peroxide as a substrate, exhibiting both catalase and peroxidase activities. Furthermore, the synthesis of a new series of salen manganese complexes that are analogs of C7 are described and their multiple catalytic activities summarized. All of these compounds showed SOD activities comparable or identical to that of C7. Many of the compounds, like C7, also function as catalases and peroxidases. In contrast to their similar SOD activities, the salen manganese complexes displayed a wide range of catalase/peroxidase activities, consistent with the two catalytic functions being structurally dissociable. Finally, the series of salen manganese complexes was evaluated in three biological models for ROS-induced damage. All of the compounds inhibited iron-induced lipid peroxidation in isolated brain homogenates and protected cultured human fibroblasts from t-butyl hydroperoxide toxicity. However, only four compounds from the series effectively protected human fibroblasts against toxicity by glucose and glucose oxidase, a hydrogen peroxide-generating system. These four compounds also exhibited more favorable properties than the other salen manganese complexes in the catalase/peroxidase assays. Overall, these findings demonstrate that the antioxidant salen-metal complexes of the invention constitute a new class of catalytic SOD/catalase/peroxidase mimics with clinical utility and applicability, as well as finding use in other applications (e.g., as antioxidative reagents, stabilizers, and the like).

In cultured hippocampal slices, C7 protects against functional synaptic damage induced by anoxia-reperfusion and blocks acidosis-induced lipid peroxidation. in the iron-loaded isolated perfused rat heart, C7 protects against both structural and functional damage caused by ischemia-reperfusion. C7 has also been found to reduce the degeneration of dopaminergic neurons in vivo, in two mouse models for Parkinson's disease (Example 1, supra) and to protect neurons against amyloid peptide toxicity in vitro. In addition, C7 is protective in an in vitro model for acidosis-induced mucosal injury.

A new series of salen-metal compounds have been synthesized, all of which are sufficiently water soluble to facilitate their compatibility with biological systems. Certain of these salen manganese complexes, in addition to having SOD activity, also function as catalases, converting hydrogen peroxide to oxygen. Furthermore, the compounds exhibit peroxidase activity in the presence of an oxidizable substrate. This is consistent with their ability to mimic the proteinaceous catalases.

In this Example, the synthesis and multiple catalytic activities of this new series of salen manganese complexes is described. In addition, the ability of these compounds to inhibit lipid peroxidation and to protect human fibroblasts in two models for oxidative damage was examined.

Materials

0-Vanillin, 2-hydroxy-4-methoxybenzaldehyde, 2-hydroxy-5-methoxybenzaldehyde, 4,6-dimethoxysalicylaldehyde, 3-fluorosalicylaldehyde, ethylenediamine, and manganese (II) acetate dihydrate were purchased from Aldrich Chemical Company (Milwaukee, Wis.). All solvents used in synthesis of the compounds were reagent grade and were used without further purification. Solvents used in analysis of C7 inactivation were HPLC grade and were purchased from EM Sciences (Gibbstown, N.J.). The XTT reagent was obtained from Boehringer Mannheim, Inc. (Indianapolis, Ind.). All components of tissue culture media were purchased from BioWhittaker (Walkersville, Md.) and tissue culture plastic ware was from Corning (Corning, N.Y.). All other chemicals were obtained from Sigma Chemicals (St. Louis, Mo.).

Synthesis and Characterization of Salen-Manganese Complexes

The bis(salicylaldehyde)ethylenediamine (salen-H2) substituted ligands were prepared by the addition of 1 equivalent of ethylenediamine in absolute ethanol to a solution of 2 equivalents of the substituted aldehyde in absolute ethanol (0.05 to 0.2 M solution). The precipitate was filtered, washed with ethanol, and air dried to give the desired product in 79 to 96% yield. C-7 and C31 were prepared using a published procedure (Boucher et al. (1974) *J. Inorg. Nucl. Chem.* 36: 531; Boucher et al. (1974) *Inorg. Chem.* 13: 1105), which was modified to produce the other complexes. One equivalent of solid manganese (II) acetate tetrahydrate was added to a stirred suspension of one equivalent of the ligand in 95% ethanol (0.125 to 0.03M), either at ambient temperature or at reflux, and the reaction then stirred for 1 to 2 hr. The dark brown solutions were then dried under a stream of air. The crude product, a brown solid, was washed with acetone, filtered, and air dried. The products were obtained at hydrates in 62 to 92%.yield. The acetate complexes were converted to the corresponding chlorides by treating an aqueous solution (0.03 to 0.06M) of the acetate, warmed to 50° C., with 5 equivalents of KCI dissolved in distilled water. A brown precipitate immediately formed. The suspension was cooled in an ice/water bath the filtered and the brown solid was washed with water and acetone. The products were obtained as hydrates in 66 to 78% yield. Protein NMR spectra of the ligands were obtained on a Bruker ARX 400 MHz instrument. Elemental analysis of final products were performed by Canadian Microanalytical Services (Delta, B.C., Canada). All analytical data were consistent with the structures indicated in FIG. 12.

Superoxide Dismutase Activity

Superoxide dismutase (SOD) activity was assayed by following the inhibition of the reduction of an electron acceptor molecule in the presence of the free-radical generating system xanthine/xanthine oxidase (McCord et al. (1973) *Superoxide and Superoxide Dismutase* in "Oxidases and Related Redox Systems, vol. I, King et al. eds., University Park press, Baltimore, pp. 51–76). The assay mixture consisted of 50 mM sodium phosphate, pH 7.8, 120 $\mu$M xanthine, 0.2 units/ml xanthine oxidase, with acceptor molecule and salen manganese compound, as indicated. Assays were conducted at 27±0.2° C. using a water-jacketed cell holder in a Beckman DU7400 spectrophotometer. In most cases, oxidized cytochrome c, at 0.13 mg/ml, was employed as acceptor and its reduction was monitored spectrophotometrically at 550 nm. In some experiments, nitroblue tetrazolium (NBT), at 80 $\mu$M, was substituted for cytochrome c as the acceptor. NBT reduction was also monitored at 550 nm. An estimated extinction coefficient for NBT reduction, 20,800 $M^{-1}$ $cm^{-1}$, determined empirically by exhaustive reduction of NBT in the reaction mixture described above, was employed where indicated. This value agreed well with reported extinction coefficients for reduced tetrazolium dyes. Control reactions to ensure that the compounds did not directly inhibit xanthine exidase were performed by monitoring urate production at 290 nm in reaction mixtures lacking cytochrome C of NBT. Conversion of xanthine to urate was calculated using $\epsilon$290's of 12,200 $M^1$ $cm^{-1}$ for urate and 4050 $M^{-1}$ $cm^{-1}$ for xanthine. To compare the SOD activities of the various salen manganese complexes, their $IC_{50}$'s in reaction mixtures containing cytochrome C as the indicator were determined from concentration-independent plots as described by Faulkner and Friedovich (1994) with correlation coefficients ranging from 0.97 to 0.99. For each compound, at least four different concentrations were tested in duplicate.

Catalase Activity

Catalase activity was assayed by monitoring the conversion of $H_2O_2$ to oxygen using a Clark-type polarographic oxygen electrode. The apparatus consisted of a Mini Clark Style electrode, a 600 $\mu$l Oxygen Uptake Chamber, and a Chemical Microsensor system, all obtained from Diamond General Corporation (Ann Arbor, Mich.). The electrode was calibrated by immersion in nitrogen- or air-equilibrated buffers using a Dual Chamber Calibration Cell (Diamond General, Corp.). Catalase reaction mixtures consisted of 50 mM sodium phosphate, pH 8.1,0.9% sodium chloride, and salen manganese complex and $H_2O_2$ at the indicated concentrations. The temperature of the water-jacketed reaction chamber, as well as the calibration buffers, was maintained at 25±0.1° C. Data were collected at 1 sec intervals and stored on a MacIntosh II computer using data acquisition hardware and software by Strawberry Tree, Inc. (Sunnyvale, Calif.). Dissolved oxygen concentrations were calculated as described previously (Del Rio et al. (1977) *Anal. Biochem.* 80: 409) based on a value of 2.5×$10^{-4}$ M oxygen for air-saturated buffer at 25° C. Linearity of the dissolved oxygen measurements within the experimental range was continued by determining the amount of oxygen generated from known quantities of $H_2O_2$ during exhaustive treatment with bovine liver catalase. Stock solutions of $H_2O_2$ were prepared by diluting a commercial 30% $H_2O_2$ solution in water and the $H_2O_2$ concentrations in these stocks were determined by absorbance at 240 nm, using a molar extinction coefficient of 44 (Stadtman, ER. et al. (1990) *Proc. Natl. Acad. Sci. USA* 87: 384). Under these reaction conditions, combinations of salen manganese complex and $H_2O_2$ resulted in the time-dependent generation of oxygen, as described under Results. In the absence of salen manganese complex, $H_2O_2$ alone typically produced an early, relatively slow increase in signal. The slope of this increased signal was not proportional to $H_2O_2$ concentration (for example in one experiment, 1 and 10 Mm $H_2O_2$ yielded apparent rates of 12 and 14 μM oxygen per min, respectively) and may be due to an electrode artifact. No such drift was observed with salen manganese complex alone. Where presented, initial rates were calculated by determining the slope of the linear portion of time dependent plots of oxygen generation, usually comprising the first five seconds of the reaction. Unless otherwise indicated, these were corrected by subtracting the rate obtained with $H_2O_2$ alone. Where presented, endpoint oxygen generated was calculated from time-dependent plots, such as those shown in FIG. 14, as the difference between the baseline oxygen concentration immediately prior to substrate addition and the maximal oxygen concentration achieved during the course of the reaction. All reactions subjected to these calculations were run for a sufficient time to ensure that oxygen generation had ceased.

C7 Inactivation

The decomposition of C7 in $H_2O_2$ was examined by incubating 100 μM C7 with 1 Mm $H_2O_2$ in 5 Mm sodium phosphate, pH 8.1 with 0.9% NaCl at room temperature (22 to 23° C.). Where indicated, 1 mM ABTS was also present. components were mixed and, after various incubations times, a 30 μl aliquot was injected onto the HPLC. The mixtures were chromatographed on an octadecyl-silica column using a mobile phase consisting of 60% methanol:40% 0.1 M NaCl and a flow rate of 1 ml/min. C7 and salicylaldehyde exhibited retention times of 4.0 and 5.6 min, respectively while $H_2O_2$ eluted in the void volume. A third component, with a retention time of 4.8 min, was detectable under some conditions; its appearance and disappearance was monitored but it was not further analyzed. In this system, ABTS and its oxidized product had retention times of 3.4 and 3.1-min, respectively, well resolved from the peaks of interest. Absorbance spectra collected during each run allowed the identity of C7 and salicylaldehyde to be verified. All peaks were integrated based upon their absorbance at 240 nm. The results are expressed as the percentage of maximum peak area. In the case of C7, this is equivalent to the peak area obtained in an incubation mixture prepared in the absence of $H_2O_2$. For the two putative breakdown products, this is equivalent to the largest peak observed during the course of the ~2000 sec incubation period.

Peroxidase Activity

Peroxidase activity was assayed by monitoring the hydrogen peroxide-dependent oxidation of 2,2'-azino-bis(3-ethylbenzthiazoline-6) sulfonic acid (ABTS) spectrophotometrically. Standard assay mixtures consisted of 50 mM sodium phosphate, pH 8.1, 0.9% sodium chloride, 0.5 mM ABTS, and $H_2O_2$ and salen manganese complex as indicated. Where indicated, 50 mM sodium phosphate buffers of pH 6.0 or pH 7.1 were substituted. Assays were conducted at 27±0.2° C. ABTS oxidation was monitored at 740 or 500 nm to eliminate interference by the salen manganese complexes, many of which absorb in the vicinity of the $\lambda_{max}$ of oxidized ABTS, and to avoid absorbance values that exceeded the linear range of the spectrophotometer. The amount of oxidized ABTS was estimated using an $\Delta\epsilon_{740}$ of 20,300 $M^{-1}$ $cm^{-1}$ or an $\Delta\epsilon_{500}$ of 3400 $M^{-1}$ $cm^{-1}$ calculated based upon the published molar extinction coefficient oat 405 nm (36,800).

Lipid Peroxidation

To prepare brain homogenates, rat brains, minus the pons and cerebellum, were each homogenized in 7 volumes of an artificial cerebral spinal fluid (ASCF) containing 124 mM NaCl, 3 mM KCl, 1.25 mM $KH_2PO_4$, 3 mM $CaCl_2$, 1 mM $MgCl_2$, 26 mM $NaHCO_3$, 10 mM D-glucose, and 2 mM L-ascorbate, equilibrated with $O_2:CO_2(95:5)$. Lipid peroxidation was induced by incubating a mixture consisting of 0.25 ml homogenate, 0.25 ml ASCF with test compounds, and 10 μM $FeCl_2$ for 1 hr at 35° C. under an atmosphere equilibrated with $O_2:CO_2(95:5)$. Following the incubation, 0.1 ml of the sample was extracted with trichloroacetic acid and analyzed for thiobarbituric acid reactive material as described previously, using authentic malonyldialdehyde (MDA) as a standard.

Cell Protection Assays

Human dermal fibroblasts (HF cells) were obtained from the American type tissue Culture Collection at passage 1 and cultured and propagated in a medium (HF medium) consisting of Dulbecco's Modified Eagle's Medium with 4.5 g/l D-glucose, 10% calf serum 4 mM glutamine, 50 units/ml penicillin, and 50 g/ml streptomycin in a 37° C. humidified incubator equilibrated with 5% $CO_2$. Cells were used at passages 5 or 6 for experiments. For cell protection assays, HF cells were seeded at a density of about 15,000 cells per cm2 onto 96-well culture plates and allowed to grow to confluence. To assess protection tert-butylhydroperoxide (t-BHP) toxicity, confluent cell layers were first treated with the indicated concentrations of test compounds dissolved in HF medium for 18 hr. The medium was then replaced with fresh medium containing test compounds and 0.5 mM tert-butylhydroperoxide (t-BHP) and cells were incubated for another 18 hr. The medium was then removed and replaced with fresh HF medium (100 μl per well) without test compounds or t-BHP. Fifty μl of XTT reagent (Boeringer Mannheim, Inc.), prepared as described by the manufacturer, was then added to each well and the plates returned to the incubator. After 2 hr., the absorbance at 490 nm was measured in a BioRad (Richmond, Calif.) Model 3550 plate-reader, using a reference wavelength of 655 nm. Control cells that had not been exposed to test compounds or toxic agents were included among the samples treated with XTT reagent. Absorbance measurements for blank wells, containing HF medium and XTT reagent but no cells, were also determined. To analyze protection from glucose/glucose oxidase toxicity, confluent cell layers were incubated with HF medium containing glucose oxidase (0.019 units/ml) along with test compounds, as indicated, for 18 hr in the tissue culture incubator. Fresh HF medium was then added and cell viability assessed using the XTT reagent as described above. For both these models, concentrations of toxic agents were selected that were reproducibly completely lethal. Cytotoxicity assessments were routinely confirmed by visual inspection of the cell layers prior to addition of the XTT reagent.

Results

Structure of Salen Manganese Complexes

FIG. 12 shows the structures of salen manganese complexes evaluated in this Example. The Schiff base ligands used to complex manganese (III) are derivatives of the tetradentate ligand bis(silicylaldehyde)ethylenediamine (salen-H2). Two series of compounds, one set having a chloride axial ligand and the other having an acetate axial ligand, were synthesized. All compounds have a mirror plane or symmetry. In general, those compounds with an axial acetate ligand were found to be more water soluble than the corresponding chlorides. In addition, the acetate axial ligand can be rapidly converted to the chloride in the presence of chloride salts. The reference compound used in this study was C7. This manganese complex contains a chloride axial ligand and unsubstituted salen ligand. It has previously been found to exhibit SOD activity of about 769 units/mM. The other complexes contain salen ligands with substituents, either methoxy or fluorine, on the aromatic rings as shown in Table I. The chloride and acetate pairs are, respectively, C7 and C31, C37 and C36, C41 and C38, C40, C32, C39, and C35, and C34, and C33. The two members of each pair showed similar, if not identical, activity in the various assay systems, as discussed further below.

TABLE VII

Catalytic activities of salen manganese complexes

Compounds were assayed for SOD as described under Experimental procedures, using cytochrome C as acceptor. The concentration of each compound showing half-maximal activity in this assay is presented. Catalase and peroxidase activities were conducted as described under Experimental Procedures, with 10 μM salen manganese complex. The $H_2O_2$ concentration was 10 mM and 0.2 mM in the catalase and peroxidase assays, respectively. Where denoted, "nd" means that the assay was not performed on this compound. C39 exhibited limited solubility (≦1.8 μM).

Multiple Enzymatic Activities of C7, A Prototype Salen Manganese Complex

Figure 13A:
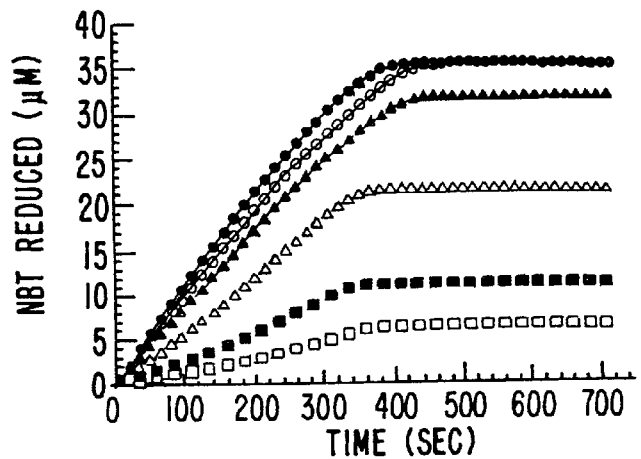
FIGS. 13A and 13B shows that C7 inhibits NBT reduction without affecting xanthine oxidase activity in an SOD assay. C7 was assayed for SOD activity as described under Experimental Procedures using NBT as acceptor.
Figure 13B:
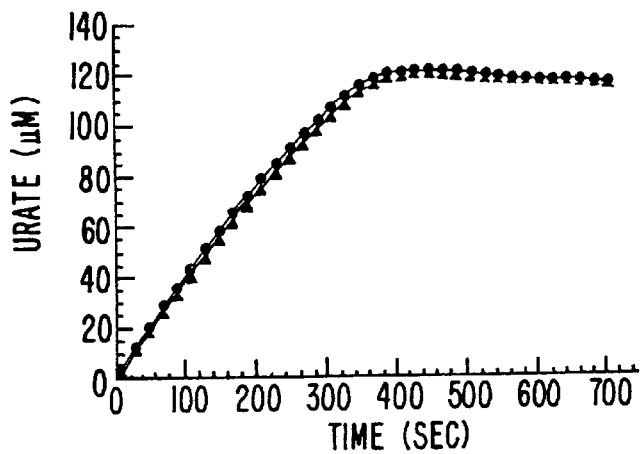

Example 1 demonstrates that certain salen manganese compounds have superoxide dismutase (SOD) activity, based upon their ability to inhibit the reduction of nitroblue tetrazolium (NBT) in the presence of the superoxide generating system xanthine and xanthine oxidase. For example, as shown in FIG. 13A, C7 inhibited the rate of NBT reduction in a concentration-dependent manner, with no effect on xanthine oxidase activity (FIG. 13B). The stoichiometries observed in these experiments support a catalytic mechanism for C7, since large molar excesses of superoxide were apparently scavenged by the salen manganese complex. In FIGS. 13A and 13B, in the absence of C7, about 38 nmoles NBT was reduced before the reaction leveled off due to consumption of xanthine and about 1.7 nmoles C7 inhibited this reduction by about 59%. During the same time, about 125 nmoles of xanthine were converted to urate.

Figure 14:
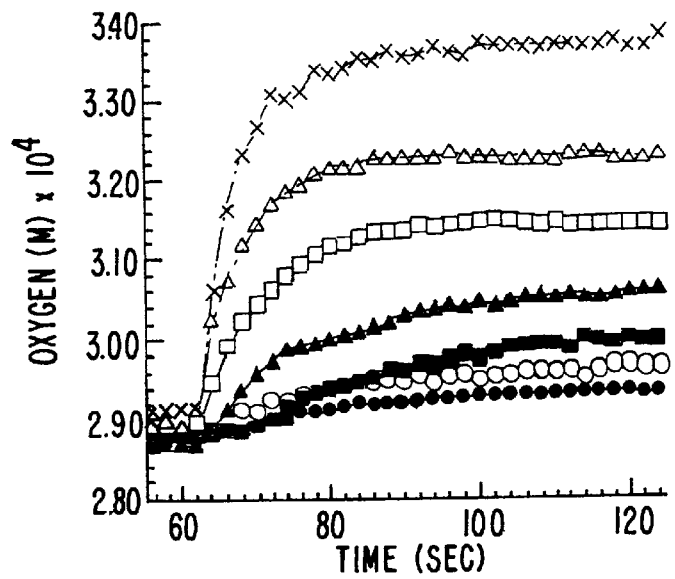
FIG. 14 shows that C7 exhibits catalase activity. C7 was assayed for catalase activity as described under Experimental Procedures. The concentration of C7 was 10 MM and the concentration of $H_2O_2$ was as indicated: (solid circle), 0.6 my.; (open circle), 1.2 mM; (solid triangle), 2.3 mM; (open triangle), 4.6 mM; (solid diamond) 9.2 mM; (open diamond), 18.3 mM; (X) 36.6 mM.

Catalase activity was detected by monitoring the generation of oxygen, as described under *Experimental Procedures*, in the presence of $H_2O_2$. As shown in FIG. 14, the addition of $H_2O_2$ to a solution of C7 resulted in a phase of rapid oxygen production that leveled off well before 100 sec, not having yielded enough oxygen to account for the available amount of $H_2O_2$. Additional $H_2O_2$ did not reinitiate the reaction while additional C7 did. These observations demonstrated that C7 was inactivated during the course of the reaction. An $H_2O_2$-dependent C7 degradation was investigated further using HPLC as described below. As FIG. 14 also indicates, both the initial rate of oxygen generation and the total amount of oxygen produced increased with the concentration of $H_2O_2$. Thus, at higher substrate concentrations, C7 completed more catalytic cycles before ceasing to react. The catalase activity of C7 did not appear saturable within the range of $H_2O_2$ concentrations examined. Similarly, kinetic analyses of mammalian catalases indicate that the enzymes lack a $K_m$ for $H_2O_2$ and therefore exhibit increased activity as the intracellular $H_2O_2$ concentration increases.

The use of $10^{-3}$ to $10^{-4}$ M concentrations of $H_2O_2$ in our experiments was dictated by the sensitivity of our oxygen measurement system. However, far lower concentrations of $H_2O_2$ may be present in vivo, even under conditions of pathological ROS generation.

C7 also exhibited peroxidase activity, which is consistent with its function as a catalase. The catalase reaction involves conversion of two moles $H_2O_2$ to one mole oxygen and two moles of water.

Figure 15A:
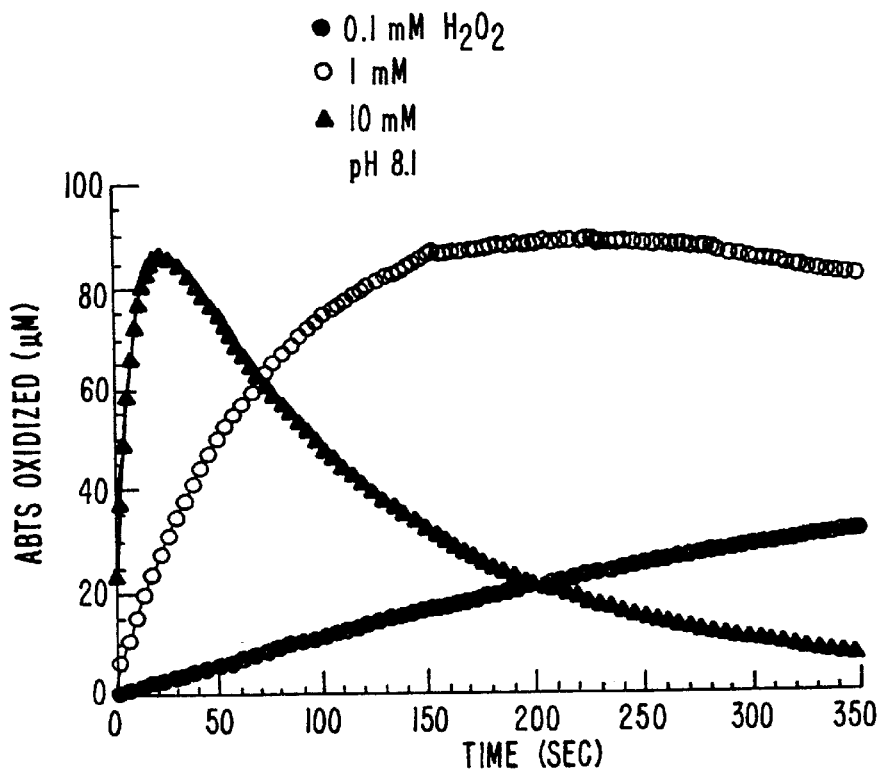
FIGS. 15A and 15B show that C7 exhibits peroxidase activity toward the substrate ABTS. C7 was assayed for peroxidase activity as described under Experimental Procedures. The concentration of C7 was 10 $\mu$M and the concentration of $H_2O_2$ and the pH of the sodium phosphate reaction buffers were as indicated.
Figure 15B:
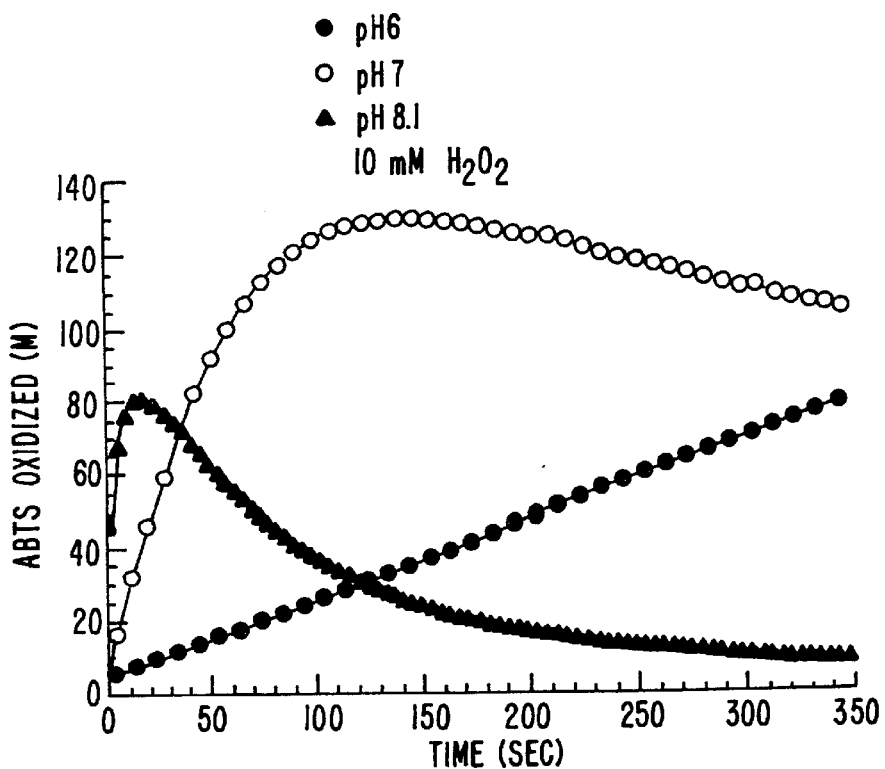

As shown in FIGS. 15A and 15B, C7 catalyzed a peroxidative reaction between $H_2O_2$ and the oxidizable substrate ABTS. As with its catalase activity, the peroxidase activity of C7 was dependent on $H_2O_2$ concentration, with no apparent saturation reached at any concentration tested.

At high $H_2O_2$ concentrations, the kinetics of ABTS oxidation were complicated by the apparent bleaching of the oxidized product. As illustrated in FIG. 15B, the peroxidase activity of C7 decreased with pH from 8.1 to 6.0. The catalase activity of C7 showed a similar pH dependence and both activities were even faster at pH 8.9. Under these assay conditions, bovine liver catalase (19 units/ml) showed no peroxidase activity toward ABTS at pH 6.0, 7.1, 8.1. In comparison, in our catalase assays, the same concentration of bovine liver catalase produced oxygen at the rate of ~0.33 mM/min in the presence of 2.3 mM $H_2O_2$. Under similar conditions (pH 8.1, 1 mM $H_2O_2$), horseradish peroxidase (13.2 units/ml) oxidized ABTS at a rate of 99.3 mM/min.

From the data presented in FIGS. 15A and 15B, it is apparent that C7 underwent many more turnovers in the peroxidase paradigm than it did under catalase assay conditions. For example, in FIG. 15A, up to 88 μM ABTS was oxidized, presenting over 8 turnovers, in a reaction containing 1 MM $H_2O_2$. By comparison, catalase reactions containing the same concentration of C7 and ~1 mM $H_2$ $_2O_2$ completed no more than a single turnover. One reason is that, at the same $H_2O_2$ concentration, the peroxidase rate was faster than the catalase. However, in general, we also found that the peroxidase reactions proceeded for a far longer time period than the equivalent catalase reactions. As FIG. 15B shows, C7 completed more turnovers, albeit more slowly, at pH 7.1 than at pH 8.1. One factor contributing to total amount of turnovers completed in these complex peroxidase reactions was the competing consumption of $H_2O_2$ by the catalase activity of the molecule, which, as discussed above, was accelerated at the higher pH. The addition of 29 units/ml bovine liver catalase inhibited the oxidation of ABTS by C7 (at 10 mM $H_2O_2$), reducing the initial rate by 55% and enabling a total of only 18 AM ABTS to be oxidized. Another factor that would account for an increased number of peroxidase turnovers at pH 7.1 would be a slower rate of C7 inactivation, which was not investigated in this study. Yet another would be the more rapid bleaching of the oxidized ABTS at the higher pH, which is also apparent in the figure.

Figure 16A:
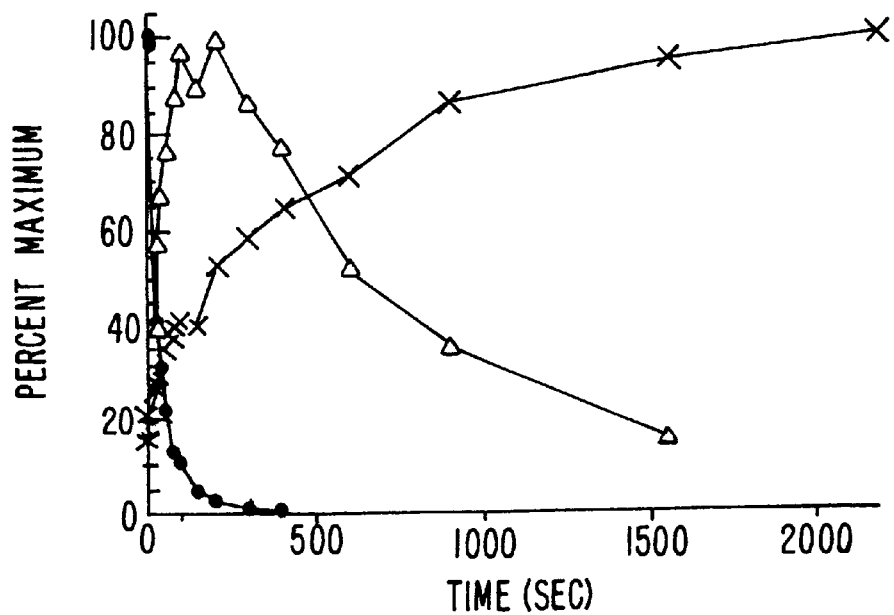
FIGS. 16A and 16B show inactivation of C7 in the presence of $H_2O_2$. C7 was incubated with $H_2O_2$ as described under Experimental procedures with aliquots removed and analyzed by HPLC.
Figure 16B:
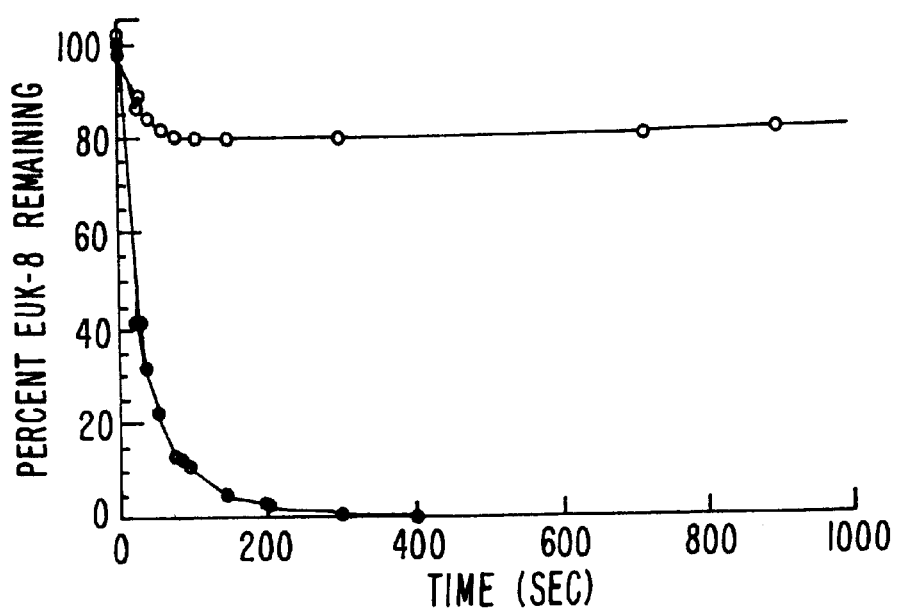

To monitor C7 inactivation under the catalase reaction conditions, the compound was incubated with $H_2O_2$ and analyzed by HPLC as described under *Experimental Procedures*. These reasons were conducted in the presence and absence of a 10-fold molar excess of ABTS. As shown in FIG. 16A, in the absence of ABTS, the peak corresponding to C7 disappeared rapidly, with an estimated half life of ~40 sec. An unidentified substance appeared concomitantly, but later decreased in amount as shown in the figure. This substance had a retention time and absorbance spectrum similar to those of the metal-free ligand, but the amount was insufficient to identify it conclusively. A third peak corresponding to salicylaldehyde appeared more slowly, increasing over the entire ~2000 sec incubation period. As shown in FIG. 16B, the disappearance of C7 was inhibited significantly in the presence of ABTS. In reactions with ABTS, about 20% of the C7 peak disappeared rapidly, but the remaining 80% persisted for the entire salen manganese ~2000 sec incubation period. Based on its retention time and absorbance spectrum, the remaining material was indistinguishable from C7. This rapid, partial C7 disappearance in the ABTS-containing reactions was reproducible and appeared to indicate a burst of C7 inactivation. The two putative breakdown products shown in FIG. 16A were not detected in incubation reactions containing ABTS.

Multiple Enzymatic Activities of a Series of C7 Analogs

The series of salen manganese compounds described in FIG. 12 were each tested for SOD, catalase, and peroxidase activities. The relative SOD activities of the salen manganese compounds were assayed in a similar system as that described above, except that cytochrome C was used as acceptor, primarily because the product of NBT reduction sometimes precipitates during the reaction, making cytochrome C a better choice for quantitative comparisons among analogs. For each compound, the half-maximally active concentration was determined as described in *Experimental Procedures*. As summarized in Table VII, most of the compounds exhibited similar SOD activities, with $IC_{50}$s ranging from 0.9 to 1.7 $\mu$M. The only markedly different SOD activities were exhibited by C7 and C39, the analogs with two methoxy groups on each salen ring, which had $IC_{50}$s of 3.2 and 3.7 $\mu$M, respectively. However, by comparison to other salen manganese complexes tested previously in Example 1, all compounds in the present series might be regarded as having similar SOD activity to one another. Because of the peroxidase activity of these compounds, it is conceivable that a peroxidatic reoxidation of cytochrome c as $H_2O_2$ is generated would reduce the observed rates in these assays. This seems unlikely to affect our reactions, however, because compounds with a variety of peroxidase activities (see below) were nonetheless comparable in their ability to inhibit cytochrome C reduction. Nonetheless, we investigated the possibility by examining the effects of catalase in the SOD assay mixture. Bovine liver catalase (29 units/ml) did not affect the rate of cytochrome C reduction by xanthine oxidase. Furthermore, the added enzyme did not change the amount of inhibition observed with 1 MM C7.

Figure 17:
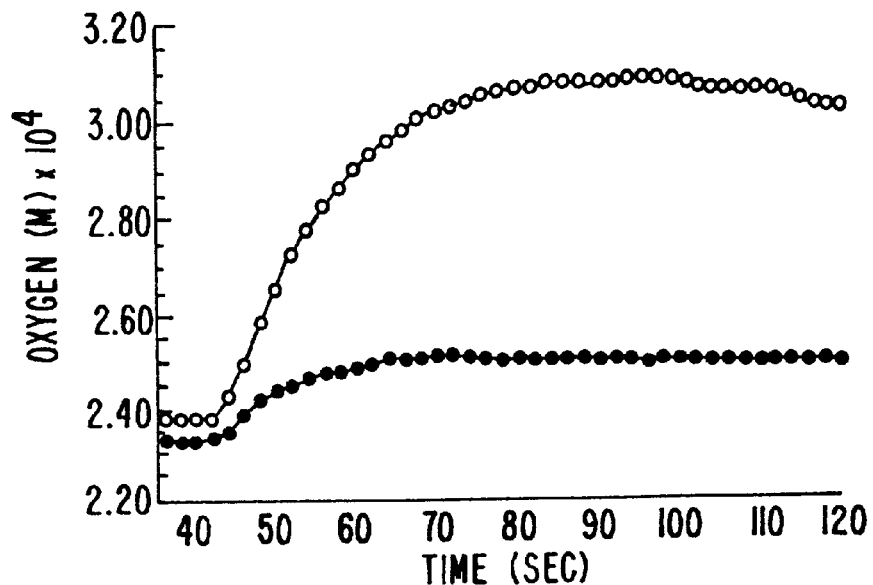
FIG. 17 shows a comparison of the catalase activities of C7 and C40. Catalase assays were performed as described for Table VII, using C7 (solid circle) or C40 (open circle).

Table VII also summarizes the catalase activities of the various salen manganese complexes when assayed under equivalent reaction conditions, that is, 10 $\mu$M salen manganese complex and 10 mM $H_2O_2$. All analogs displayed a time course analogous to that exhibited by C7, with the reaction ceasing prior to consumption of all substrate. Table VII presents initial rates as well as the maximal amount of oxygen produced, calculated from time-dependent plots as described under *Experimental Procedures*. The series of compounds displayed a wide range of catalase activities, in contrast to their very similar levels of SOD activity. In particular, C35 exhibited much lower catalase activity than the other analogs. There was also considerable variation in the total amount of oxygen generated by each compound before the reaction ceased. As with C7, the observed kinetics for these compounds were consistent with a time-dependent inactivation in the presence of $H_2O_2$. Two analogs, C41 and C32, produced almost twice the amount of oxygen as C7, corresponding to about 16 turnovers, before the catalase reaction ceased. C32 was, in addition, a faster catalase than the others, having an initial rate about twice as fast as C7 and comparable analogs. As shown in FIG. 17, C40, the chloride-complexed counterpart of C32, also exhibited a higher rate and completed more reaction turnovers than C7.

The relative peroxidase activities of the analogs showed a good correlation to their relative catalase activities (Table VII), as might be expected based upon the proposed relationship between catalatic and peroxidatic reactions. C32 and its chloride-complexed counterpart C40, were the fastest peroxidases while C35 was the poorest, in this case having undetectable activity.

Effects of Salen Manganese Complexes in Biological Model Systems

In tissues, ROS promote tissue destruction in part through oxidative damage to cellular macromolecules, in particular, by inducing lipid peroxidation. The salen manganese compounds were tested for the ability to protect brain tissue from lipid peroxidation induced by incubating brain homogenates with iron in an oxygen-rich atmosphere. Malonyldialdehyde, a byproduct of lipid peroxidation, was determined in these samples as described under *Experimental procedures*. As shown in Table VIII, all of the salen manganese complexes tested prevented lipid peroxidation at >5 $\mu$M.

TABLE VIII

Effects of salen manganese complexes on lipid peroxidation in brain homogenates

Lipid peroxidation was induced in brain homogenates and assessed based upon malonyldialdehyde (MDA) content as described under Experimental Procedures. The effects of salen manganese complexes, included in the incubation mixtures at the indicated concentrations, are expressed as percent of MDA levels in control (i.e. without salen manganese complex) incubations. Each value represents the mean of 2 to 4 experiments.

C35, while the poorest catalase/peroxidase, was nonetheless very potent in preventing lipid peroxidation.

Salen manganese compounds were also evaluated for the ability to protect human fibroblasts against tert-butylhydroperoxide (t-BHP) toxicity as described under *Experimental Procedures*. T-BHP is believed to cause oxidative damage to cells due to its intracellular decomposition to alkoxyl and methoxyl free radicals. It has been reported that SOD, particularly when encapsulated into liposomes, protects hepatocytes from t-BHP toxicity, implying that intracellular superoxide may play a role in the cytotoxicity of this organic hydroperoxide. The ability of several salen manganese compounds to protect in this model is illustrated in Table IX.

TABLE IX

Effects of Salen-Metal Complexes on t-Butyl Hydroperoxide Toxicity in Human Fibroblasts Cell protection assays were performed as described under Experimental Procedures with salen-manganese complexes administered at the indicated concentrations and t-BHP at 0.5 mM. Cell viability was assessed using the XTT reagent as described and is expressed as the absorbance at 490 nm uncorrected for blank. The value represent mean +/- s.d. of triplicate samples.

Under the conditions employed in this assay, t-BHP was fully toxic against the human fibroblasts. (Based on a lack of spectrophotometric change, t-BHP, unlike $H_2O_2$, has no apparent ability to oxidatively destroy C7). All the salen manganese complexes exhibited full protection, although their minimally effective concentrations differed. For C7 and C31, significant protection was observed at $\geq$5 $\mu$M. All other compounds, except C35, showed some protection at $\geq$10 $\mu$M. C35 was protective only at $\geq$20 $\mu$M. Several of the compounds exhibited a biphasic dose response, as indicated by reduced viability at 80 $\mu$M relative to 40 $\mu$M. Two compounds, C35 and C41, showed equivalent toxicity with or without t-BHP. However, the remaining compounds were not toxic alone at 80 $\mu$M. This is consistent with a possible synergistic toxicity with t-BHP for certain of these compounds, namely C7, C31, C36, and C37.

It has been reported that some peroxidases use organic peroxides as alternative substrates to $H_2O_2$, which indicates that such an interaction might contribute to protection in our cytotoxicity model or even be involved in the synergistic toxicity suggested about. However, in the spectrophotometric peroxidase assay, C7 exhibited weak peroxidase activity with 1 mM t-BHP, oxidizing ABTS at a rate about 0.5% of that observed with the same concentration of $H_2O_2$. (In comparison, horseradish peroxidase utilized t-BHP with an ABTS oxidation rate that was about 5.4% of the rate with $H_2O_2$). C32 was about a 3-fold faster peroxidase with t-BHP than C7. Interestingly, C36 and C37 were both even faster peroxidases with t-BHP, about twice as fast as C32. C35 had less than 2% of the peroxidase activity toward t-BHP as did C7.

The salen manganese complexes were also tested for protection of HF cells against glucose and glucose oxidase, a hydrogen peroxide-generating system. Addition of glucose oxidase (0.019 units/ml) to the HF culture system resulted in complete lethality and bovine liver catalase at 290 units/ml afforded full protection. A ten-fold lower dose of catalase was only partially protective. Most of the salen manganese complexes were essentially ineffective at protecting HF cells in this system. However, C41 and C38 were highly protective at 80 $\mu$M. C32 and C40 were even more potent, displaying significant protection at 40 $\mu$M and complete protection, equivalent to that of the bovine liver catalase, at 80 $\mu$M.

Summary

The series of salen manganese compounds of Example 2 displayed very similar SOD activities to one another, with $IC_{50}$'s ranging from 0.9 to 3.7 $\mu$M. This is in contrast to the more structurally diverse series examined in Example 1, whose $IC_{50}$'s ranged over two orders of magnitude, with C7 being among the most active. In this respect, the present series of compounds compare favorably to a manganese-porphyrin complex, which has an $IC_{50}$ of ~0.7 $\mu$M when assayed under similar conditions. It is apparent that the structural modifications described here have little effect on the SOD activity of the salen manganese complexes. In contrast, the catalase and peroxidase activities differ markedly among the various compounds. Most notably, the presence of methoxy substituents at the R1 position (as shown in FIG. 12), as exemplified by C32 and C40, increases the rate of catalase or peroxidase activity compared to the unsubstituted C7 and C31. The presence of methoxy groups at the R2 position, in C33 and C34, markedly reduces the catalase and peroxidase activities relative to the unsubstituted analogs. The activity is even further weakened in C35, with methoxy groups at both the R2 and R4 positions. The compounds in the series also differed widely in the total amount of oxygen generated prior to cessation of the catalase reactions. This parameter reflects, at least in part, the stability of the compound under the catalase reaction conditions. Thus, C41, which had a catalase rate only slightly higher than C7 and comparable to that of the fluorinated analogs, produced over twice as much oxygen as either compound before ceasing to react. This may indicate that the presence of methoxy substituents at the R3 position confers more resistance to $H_2O_2$-dependent inactivation. The stability of the entire series of compounds to $H_2O_2$ likely affects the apparent catalase and peroxidase activities exhibited in our assay systems.

The present example demonstrates that salen manganese complexes can display SOD as well as catalase/peroxidase activities and that the ratios of these activities can be structurally manipulated. Furthermore, many of these compounds are protective biologically. However, results from the two cytotoxicity models imply that the ability of a given salen manganese complex to protect is highly dependent on the biological context, including which ROS figure most prominently in the pathology. In Example 1, C7 has already been shown to be protective in much more complex biological models for ROS-induced tissue damage than those employed in Example 2.

Additional Salen-metal Complexes having Antioxidant Activity

Figure 19A:
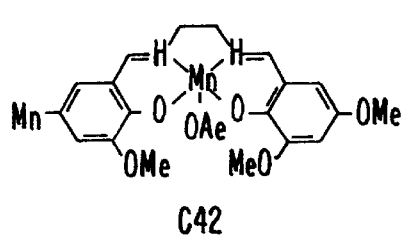
FIG. 19A shows structures of salen-manganese complexes.
Figure 19A:
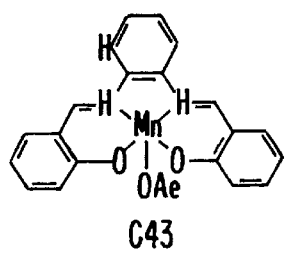
Figure 19A:
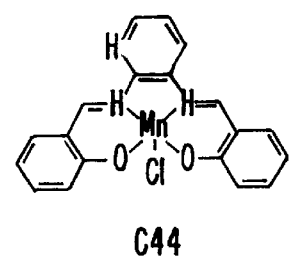
Figure 19A:
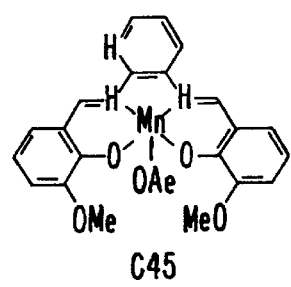
Figure 19A:
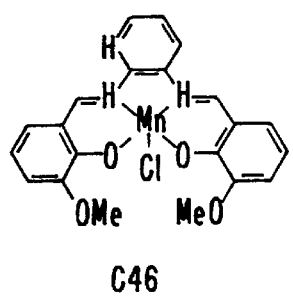
Figure 19A:
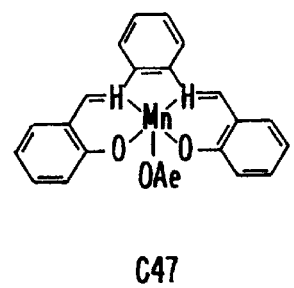
Figure 19A:
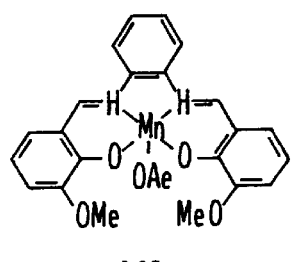
Figure 19A:
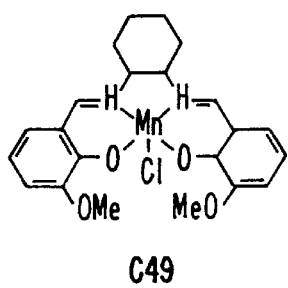
Figure 19A:
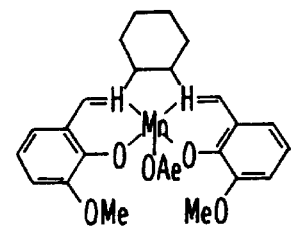
Figure 19A:
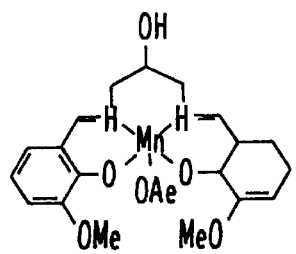
Figure 19A:
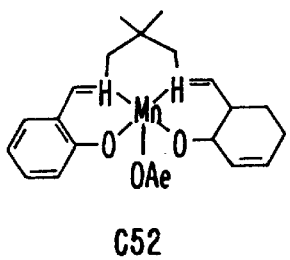
Figures 19B, 20:
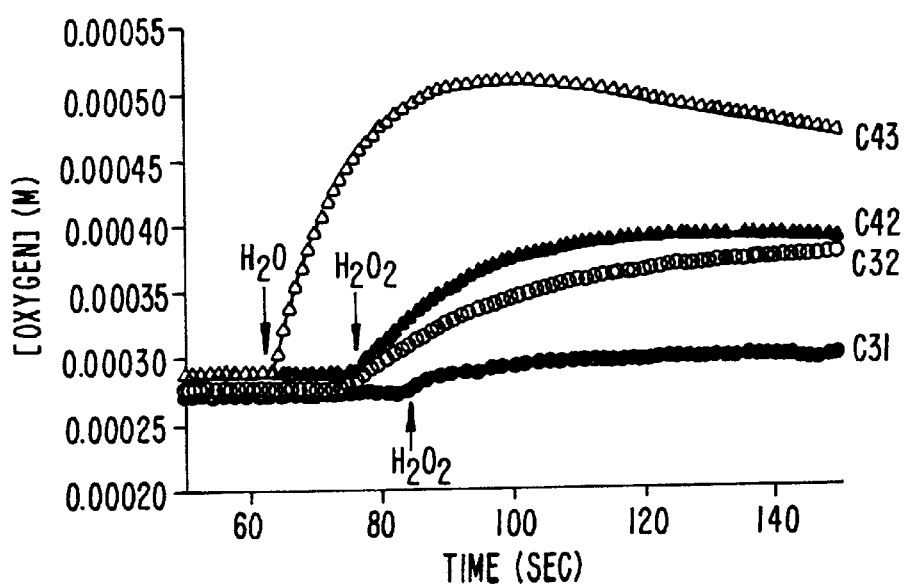
FIG. 19B shows the catalase rate, catalase endpoint, peroxidase rate, and SOD activity of these compounds relative to C7.
FIG. 20 Time-dependent generation of oxygen in the catalase assay. Catalase was assayed with a polarographic oxygen electrode as described in Example 2. Each compound was present at 10 μM. Hydrogen peroxide was added at a final concentration of 10 mM at the indicated times (arrows).

A series of salen-metal complexes were synthesized and their catalytic activities determined. FIG. 19A shows structural formulae of the salen-metal compounds C42–C52, which were synthesized and evaluated. FIG. 19B shows the catalase rate, catalase endpoint, peroxidase rate, and SOD activity of these compounds relative to C7.

Methods and Materials

0-Vanillin, 2-hydroxy-4-methoxybenzaldehyde, 4,6-dimethoxysalicylaldehyde, 2,4-dihydroxybenzaldehyde, 2,5-dihydroxybenzaldehyde, 2,3-dihydroxybenzaldehyde, manganese(II)acetate dihydrate, 2,3-dimethyl-1,3-propanediamine, (±)-trans-1,2-diaminocyclohexane, 2-hydroxy-5-methoxybenzaldehyde, 2,3-diaminopyridine, 1,3-diaminopropane, 1,3-diamino-2-hydroxypropane,3-fluorosalicylaldehyde, 1,2-phenylenediamine and 5-chlorosalicylaldehyde were purchased from the Aldrich Chemical Company (Milwaukee Wis.). All solvents used in synthesis of the compounds were reagent grade and were used without further purification and were obtained from either Caledon Laboratories (Georgetown, Ont., Canada) or Commercial Alcohols (Toronto, Ont., Canada).

Synthesis and Characterization of Salen-Manganese Complexes

The ligands were prepared by the addition of 1 equivalent of the diamine in absolute ethanol to a solution of 2 equivalents of the substituted aldehyde in absolute ethanol (0.05 to 0.2 M solution). After stirring at ambient (2 to 48 hrs), the precipitate was filtered, washed with ethanol, and air dried to give the desired product in 79 to 96% yield.

Effect of Bridge Modifications on Catalytic Activity of Salen-manganese Compounds Modification of the ethylenediamine bridge of salen-manganese compounds can affect the catalase activity (i.e., initial rate) as well as the number of turnovers completed (i.e., the catalase endpoint). The latter parameter is influenced by the stability of the compound in the presence of hydrogen peroxide. In particular, the presence of an aromatic ring at the bridge (e.g., C43, C44, C47) results in compounds that are faster catalases than C7 or C31 and that complete more turnovers. For example, compare C43 to C31 (FIG. 20, FIG. 21, Table X) or C45 to C32 (Table X). Such compounds are not necessarily faster as peroxidases (Table X, FIG. 21), indicating that peroxidase and catalase activities can be manipulated independently by such bridge modifications. Certain other bridge modifications, such as lengthening the bridge backbone by adding one carbon, result in reduced catalase and peroxidase activities. For example, compare C51 to C32 or C52 to C31 (Table X).

Effect of Methoxy Substituents on Catalytic Activity of Salen-manganese Compounds The addition of methoxy groups to the 3 and 3' positions of the salen rings results in compounds that are faster catalases and that complete more turnovers than the corresponding unsubstituted compound. For example, compare C32 to C31 (Table VII, Table X, FIG. 20). The addition of methoxy groups to the 5' and 5' positions of the salen C41 to C7 (Table VII). The presence of 4 methoxy groups, at the 3, 3', 5, and 5' positions further enhances catalase activity above those of the corresponding dimethoxy compounds.

Figure 21:
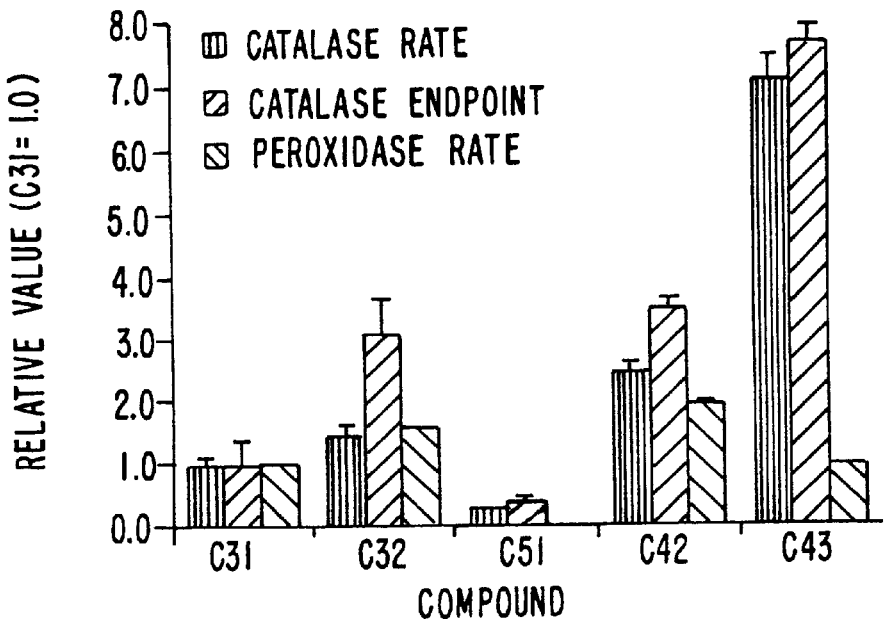
FIG. 21 Catalase and peroxidase activities of a series of compounds. Assay methods were as described for Table VII. Activities are expressed relative to C31. (mean±sd for n=$^3$).

Thus, C42 is a faster catalase than C32 (FIG. 20, FIG. 21). The presence of methoxy groups at the 4 and 4' positions results in compounds that are much slower catalases and complete few turnovers. For example, compare C33 to C31 (Table VII). The presence of four methoxy groups, at the 4, $4^7$, 6, and 6' positions, even further reduces activity. For example, compare C35 to C33 (Table VII). Even with the faster, apparently more stable bridge-modified molecules, the addition of 3, 3' methoxy groups to the salen rings enhances both the catalase rate and the number of turnovers completed. For example, compare C45 to C43 or C48 to C47 (Table X). Thus, methoxy substitution at the salen ring can modulate catalase activity, either positively or negatively.

Figure 18:
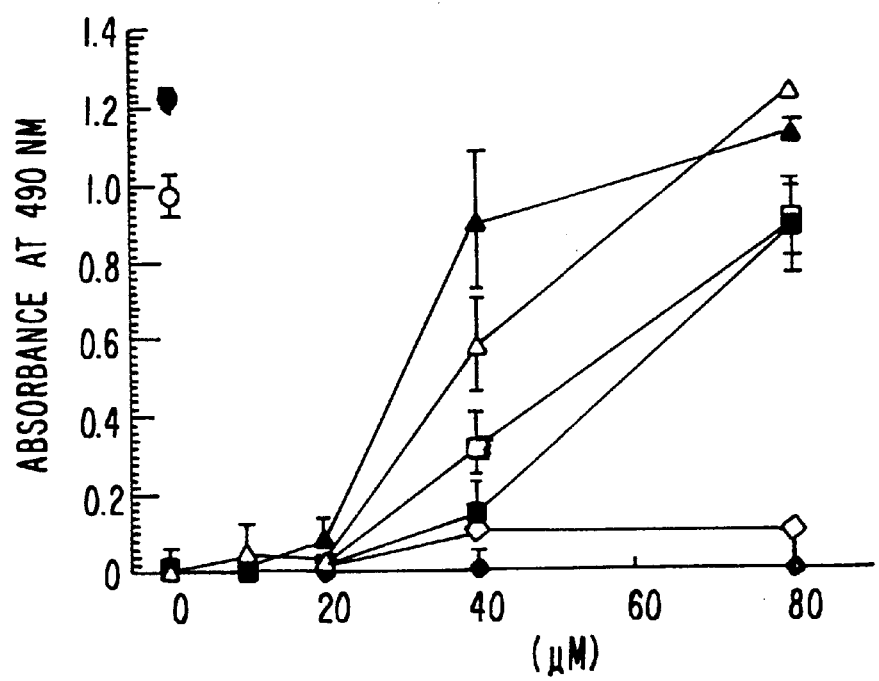
FIG. 18 shows protection against glucose and glucose-oxidase induced cytotoxicity by salen manganese complexes. Cytotoxicity studies were performed as described under Experimental procedures. Absorbance values, corrected by subtracting the blank signal of 0.17 OD units, are the means±sd of triplicate samples. Control cells (open circle) received no glucose oxidase. Catalase-treated (solid circle) cells received glucose oxidase (0.019) units/ml) as well as bovine liver catalase (290 units/ml). Other samples received the same dose of glucose oxidase and the indicated concentrations of salen manganese complex. C40 (open triangle), C32 (solid triangle), C41 (open square), C38 (solid square), C7 (open diamond), and C35 (solid diamond). Several other compounds tested (C31, C33, C34, C36, and C37) were about equally as effective as C7 and have been omitted from the figure for clarity.
Figure 22:
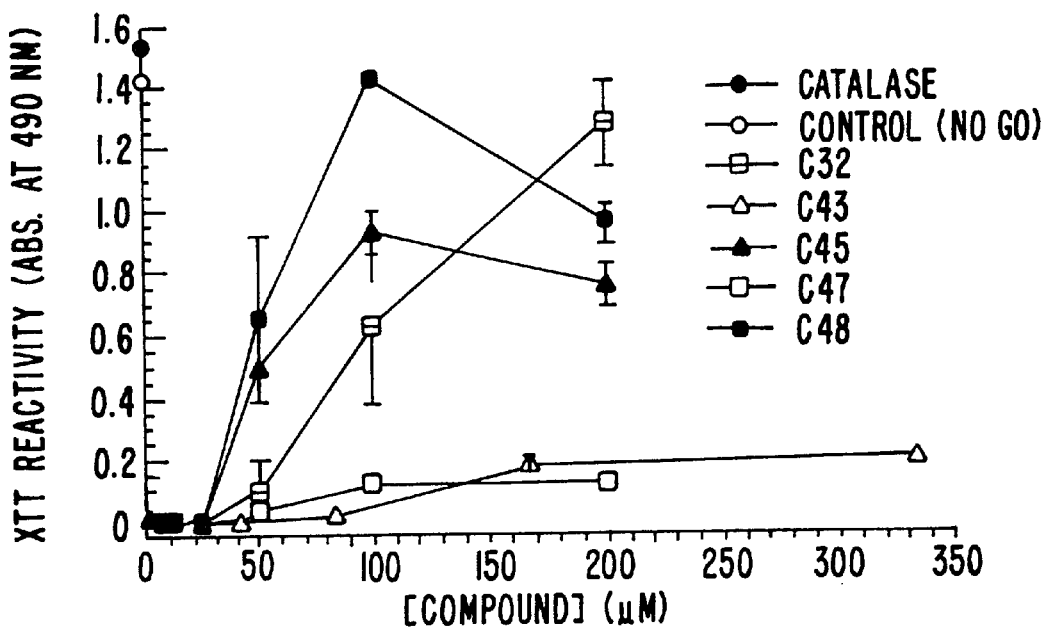
FIG. 22 Protection of human cells against toxicity by glucose and glucose oxidase. Cytotoxicity assays were performed using human dermal fibroblasts as for FIG. 18.

Effect of Methoxy Substituents on Biological Activity of Salen-manganese Compounds The presence of methoxy groups on the 3, 3' or 5, 5' positions of the salen ring enhances the ability of the compound, relative to that of the unsubstituted compound, to protect human fibroblasts against toxicity by glucose/glucose oxidase (a hydrogen peroxide generating system). For example, compare C40 and C41 to C7 (FIG. 18) and C45 to C43 (FIG. 22). Interestingly, C32 is more protective than C43 in this system (FIG. 22), even though C43 is a more active catalase than C32 (Table X). C35, which has four methoxy groups and is a poor catalase (Table VII) is not cytoprotective in this system (FIG. 18). Among a series of methoxy substituted analogs, the faster catalases are also the more cytoprotective. For example, compare C48 and C45 to C32 (FIG. 22) and C40 to C41 (FIG. 18). Thus, both methoxy substitution and catalase activity contribute to the ability of salen-manganese compounds to protect cells in one model for cellular oxidative stress.

Methods

Synthesis of C42–52

Compounds were synthesized by a modification of the method outlined in Example 2. The ligands were prepared by the addition of 1 equivalent of the diamine in absolute ethanol to a solution of 2 equivalents of the substituted aldehyde in absolute ethanol (0.05 to 0.2 M solution). After stirring at ambient (2 to 48 hrs), the precipitate was filtered, washed with ethanol, and air dried to give the desired product in 79 to 96% yield.

Catalase and peroxidase activities were assayed as described in Example 2. Catalase assays contained 10 $\mu$M salen-manganese complex and 10 mM hydrogen peroxide. Peroxidase assays contained 10 $\mu$M salen-manganese complex and 0.2 mM hydrogen peroxide. Glucose-glucose oxidase toxicity assays were performed using human dermal fibroblasts as described in Example 2.

EXAMPLE 3

Topical Formulations

Antioxidant salen-metal complexes are formulated according to the following protocols:

All percentages and ratios herein are by weight, unless otherwise specified. A moisturizing lotion is prepared by combining the following components utilizing conventional mixing techniques.

| Components | Percent by Weight of Composition |
| --- | --- |
| Water (purified) | 70.94 |
| Carbomer viscosity control agents | 0.23 |

-continued

| Components | Percent by Weight of Composition |
| --- | --- |
| (commercially available in the Acritamer series from R.I.T.A. Corp.) | |
| Alkyl Parabens | 0.90 |
| Glycerin | 3.50 |
| Potassium Hydroxide | 0.09–0.15 |
| Cetyl Alcohol | 1.25 |
| Stearic Acid | 0.75 |
| Glyceryl Stearate | 0.63 |
| Polyoxyethylene Stearyl Alcohol (commercially available in the Brij series from ICI Americas, Inc.) | 1.75 |
| Coco-Caprylate/caprate | 2.00 |
| C12–C15 Alcohol Benzoate (Finsolv TN-commercially available from Finetex, Inc.) | 2.00 |
| Salen-metal compound C7 | 2.00 |
| Octyl Methoxycinnamate | 7.50 |
| Benzophenone-3 | 1.00 |
| Octyl Dimethyl PABA | 1.00 |
| Dimethicone | 0.30 |
| Imidazolidinyl Urea | 0.10 |
| Ethylene Acrylate Copolymer | 3.80 |
| Tyrosine | 0.10 |

This lotion may be topically applied to inhibit damage caused by acute or chronic UV exposure. Use of an amount of lotion sufficient to deposit about 0.1 to 100 $\mu$g/cm$^2$ of C7 to the skin immediately prior to UV exposure is appropriate. Substantially similar results are obtained if the lotion is applied to the skin up to 4 hours prior to UV exposure or up to 30 minutes after UV exposure. Substantially similar results are obtained if the octyl methoxycinnamate, benzophenone-3, and octyl dimethyl PABA are replaced, in whole or in part, with 2-ethylhexyl p-methoxycinnamate, butylmethoxydibenzoylmethane, 2-hydroxy-4-methoxybenzophenone, and mixtures thereof.

A skin lotion is prepared by combining the following components utilizing conventional mixing techniques.

| Components | Percent by Weight of Composition |
| --- | --- |
| 4-N,N-(2-Ethylhexyl)methylamino-Benzoic Acid Ester of 4-(2-Hydroxyethoxy)-Dibenzoyl Methane | 10.00 |
| Water (purified) | 47.54 |
| Dimethyl Isosorbide | 8.00 |
| Dioctyl Maleate | 8.00 |
| C12–15 Alcohol Benzoate (Finsolv TN-commercially available from Finetex, Inc.) | 8.00 |
| Glycerin | 3.50 |
| Ethylene Acrylate Copolymer | 3.80 |
| Antioxidant salen-metal compound (e.g., C7) | 2.00 |
| Cetyl Alcohol | 1.75 |
| Polyoxyethylene Stearyl Alcohol (commercially available in the Brij series from ICI Americas, Inc.) | 1.75 |
| Stearic Acid | 1.25 |
| Glyceryl Stearate | 1.13 |
| Alkyl Parabens | 0.90 |
| Titanium Dioxide | 0.40 |
| Dimethicone | 0.30 |
| Carbomer viscosity control agents (commercially available in the Acritamer series from R.I.T.A. Corp.) | 0.23 |
| Imidazolidinyl Urea | 0.10 |
| Potassium Hydroxide | 0.15 |
| Tyrosine | 0.10 |

This lotion is useful for topical application to inhibit damage caused by acute or chronic UV exposure or exposure to an oxyradical environment. Use of an amount of lotion

What is claimed is:

1. A method for treating inflammation in a mammal, said method comprising administering to said mammal a therapeutically effective amount of a salen-metal complex of the formula:

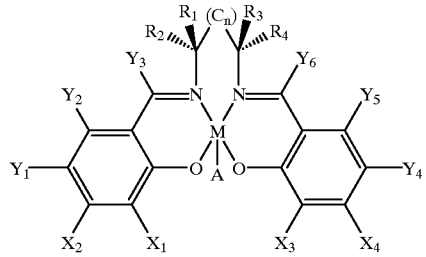

wherein:

M is selected from the group consisting of Mn, Co, Fe, V, Cr, and Ni;

A is an anion;

n is either 0, 1, or 2;

$X_1$, $X_2$, $X_3$ and $X_4$ are independently selected from the group consisting of hydrogen, silyls, aryls, arylalkyls, primary alkyls, secondary alkyls, tertiary alkyls, alkoxys, aryloxys, aminos, quaternary amines, heteroatoms, and hydrogen;

$Y_1$, $Y_2$, $Y_3$, $Y_4$, $Y_5$, and $Y_6$ are independently selected from the group consisting of hydrogen, halides, alkyls, aryls, arylalkyls, silyl groups, aminos, alkyls or aryls bearing heteroatoms, alkoxys, and halide; and $R_1$, $R_2$ $R_3$ and $R_4$ are independently selected from the group consisting of hydrogen, aryl, fatty acid esters, substituted alkoxyaryls, heteroatom-bearing aromatic groups, arylalkyls, primary alkyls, secondary alkyls, and tertiary alkyls.

2. The method in accordance with claim 1, wherein said salen-metal complex is a member selected from the group consisting of

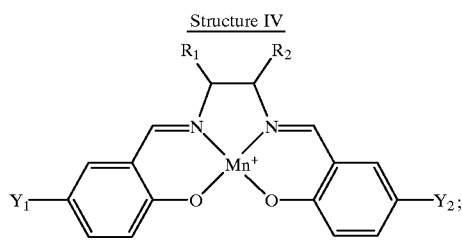

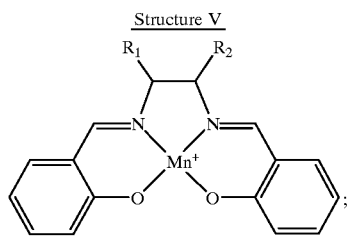

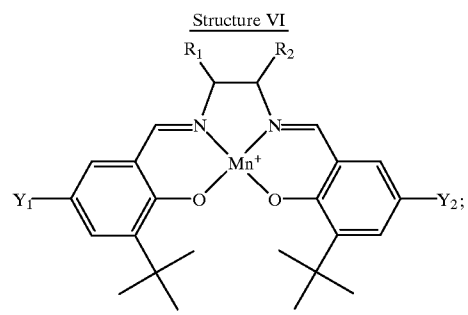

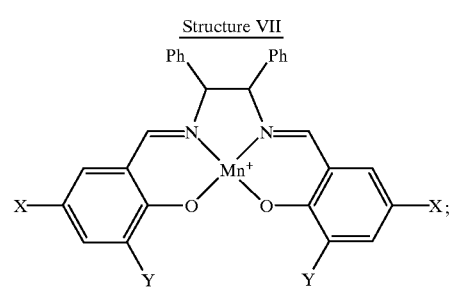

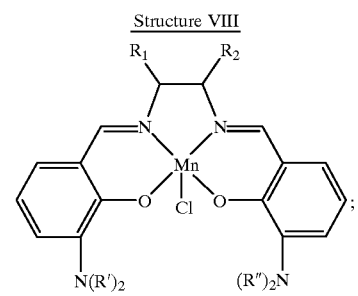

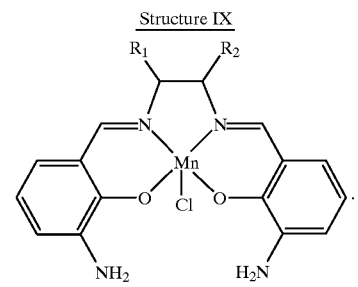

3. The method in accordance with claim 2, wherein said salen-metal complex is selected from the group consisting of:

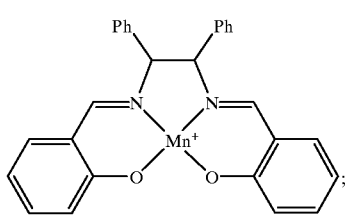

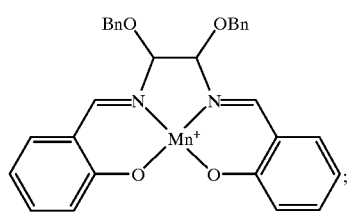
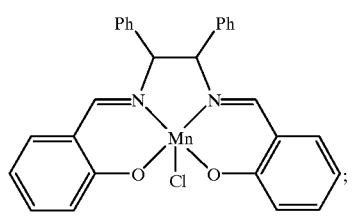
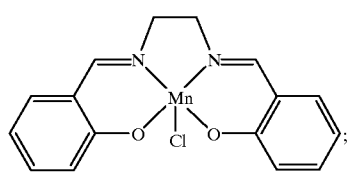
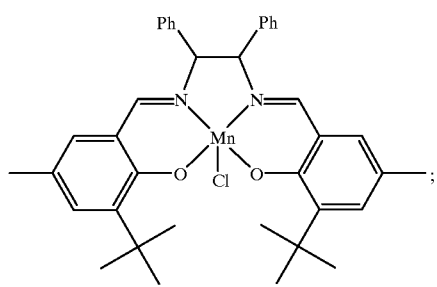
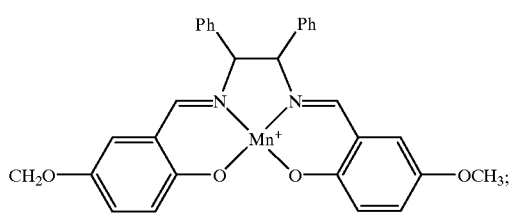
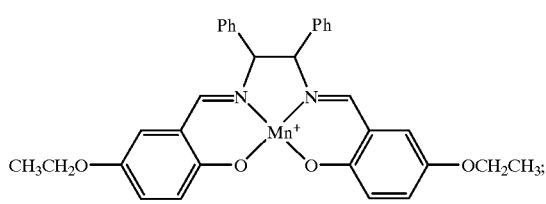
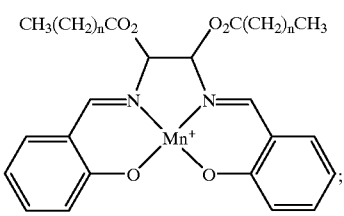
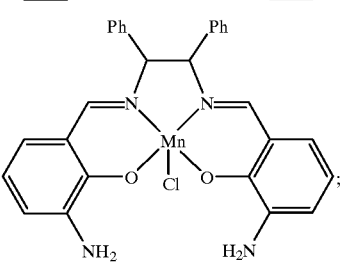
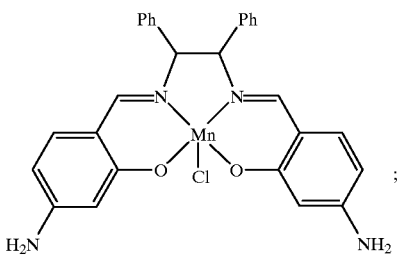
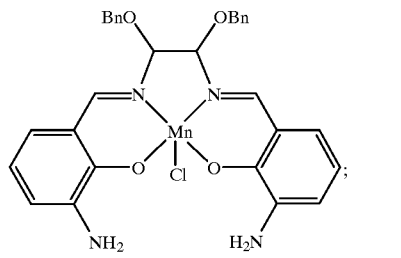
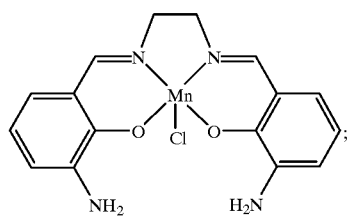
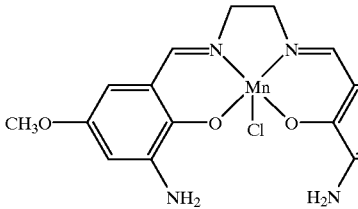

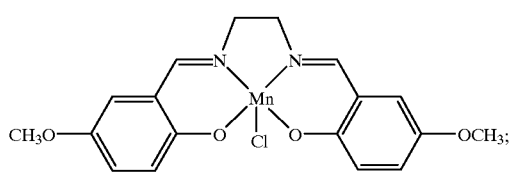
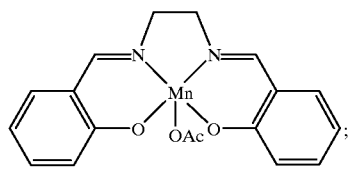
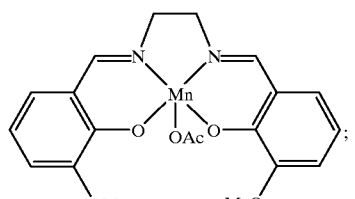
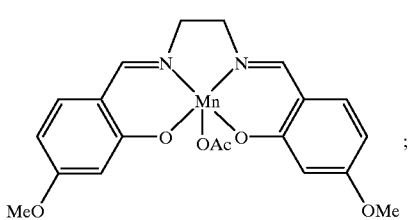
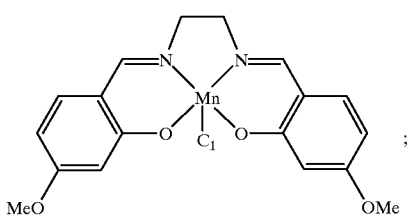
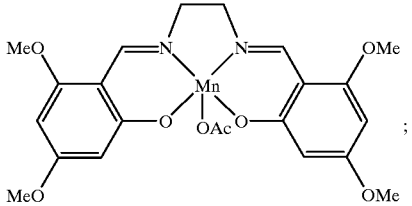
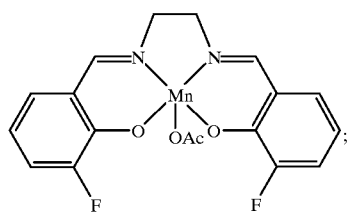
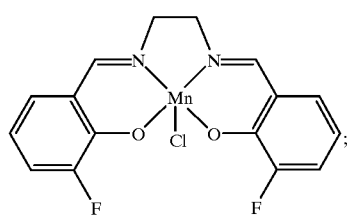
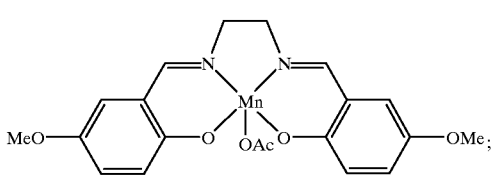
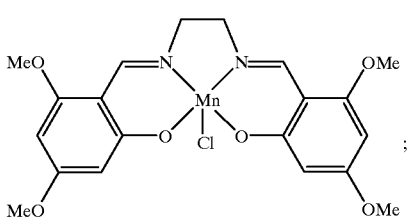
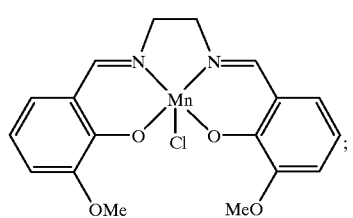
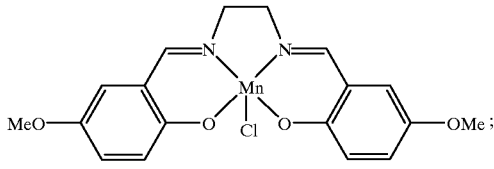
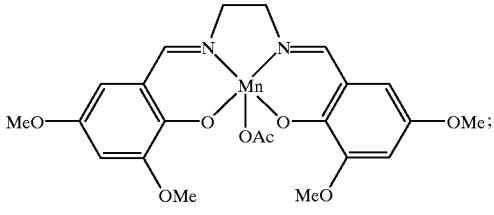
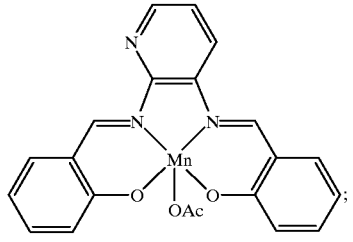

-continued

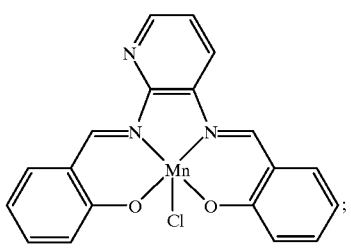

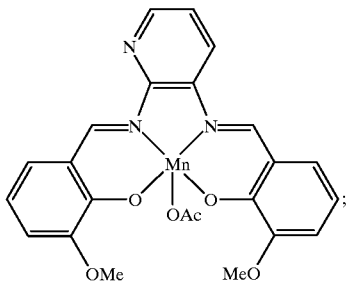

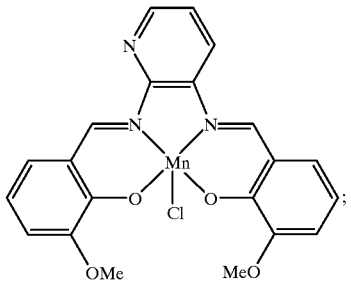

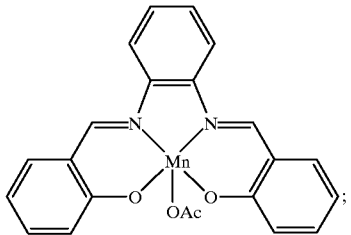

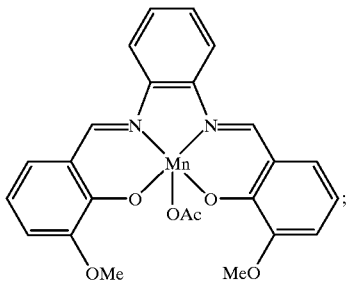

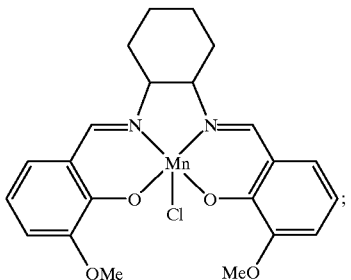

-continued

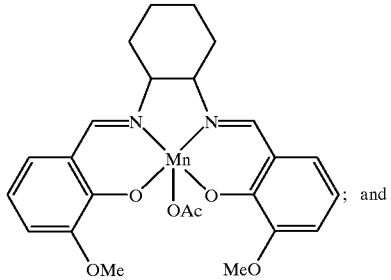

; and

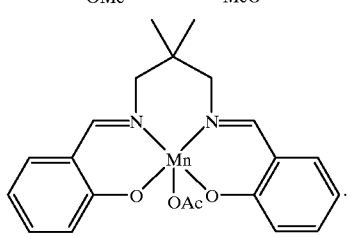

.

4. The method in accordance with claim 1, wherein said salen-metal complex is

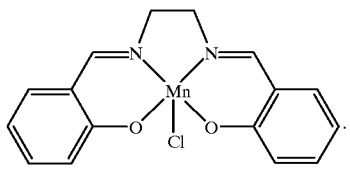

.

5. The method in accordance with claim 1, wherein said salen-metal complex is formulated in a pharmaceutically acceptable form with an excipient or carrier.

6. The method in accordance with claim 5, wherein said salen-metal complex is formulated a pharmaceutically acceptable topical carrier.

7. The method in accordance with claim 6, wherein said salen-metal complex is formulated in a dental linament for treating inflammation associated with a periodontal disease.

8. A method for treating inflammation in a mammal, said method comprising: topically administering to said mammal a therapeutically effective amount of a salen-metal complex of the formula:

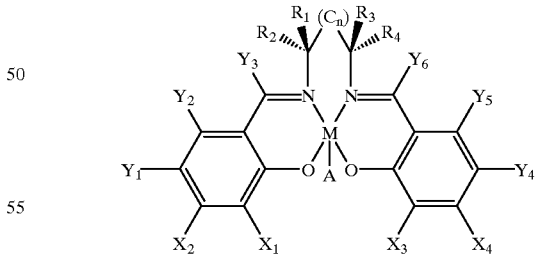

wherein:
M is selected from the group consisting of Mn, Co, Fe, V, Cr, and Ni;
A is an anion;
n is either 0, 1, or 2;
$X_1$, $X_2$, $X_3$ and $X_4$ are independently selected from the group consisting of hydrogen, silyls, aryls, arylalkyls, primary alkyls, secondary alkyls, tertiary alkyls, alkoxys, aryloxys, aminos, quaternary amines, heteroatoms, and hydrogen;

$Y_1$, $Y_2$, $Y_3$, $Y_4$, $Y_5$, and $Y_6$ are independently selected from the group consisting of hydrogen, halides, alkyls, aryls, arylalkyls, silyl groups, aminos, alkyls or aryls bearing heteroatoms, alkoxys, and halide; and $R_1$, $R_2$ $R_3$ and $R_4$ are independently selected from the group consisting of hydrogen, aryl, fatty acid esters, substituted alkoxyaryls, heteroatom-bearing aromatic groups, arylalkyls, primary alkyls, secondary alkyls, and tertiary alkyls.

9. A method for preventing or retarding the aging of skin, said method comprising: applying to said skin an effective amount of a salen-metal complex of the formula:

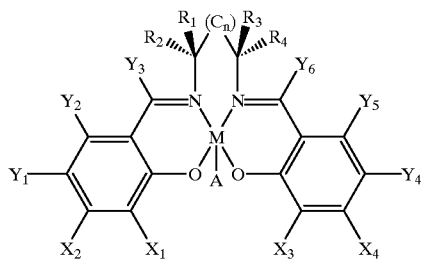

wherein:

M is selected from the group consisting of Mn, Co, Fe, V, Cr, and Ni;

A is an anion;

n is either 0, 1, or 2;

$X_1$, $X_2$, $X_3$ and $X_4$ are independently selected from the group consisting of hydrogen, silyls, aryls, arylalkyls, primary alkyls, secondary alkyls, tertiary alkyls, alkoxys, aryloxys, aminos, quaternary amines, heteroatoms, and hydrogen;

$Y_1$, $Y_2$, $Y_3$, $Y_4$, $Y_5$, and $Y_6$ are independently selected from the group consisting of hydrogen, halides, alkyls, aryls, arylalkyls, silyl groups, aminos, alkyls or aryls bearing heteroatoms, alkoxys, and halide; and $R_1$, $R_2$ $R_3$ and $R_4$ are independently selected from the group consisting of hydrogen, aryl, fatty acid esters, substituted alkoxyaryls, heteroatom-bearing aromatic groups, arylalkyls, primary alkyls, secondary alkyls, and tertiary alkyls.

10. The method in accordance with claim 9, wherein said salen-metal complex is formulated in a pharmaceutically acceptable topical carrier.

11. A method for preventing the deleterious effects of ultraviolet light exposure to skin, said method comprising: topically applying to said skin an effective amount of a salen-metal complex of the formula:

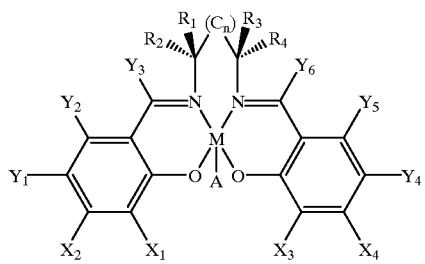

wherein:

M is selected from the group consisting of Mn, Co, Fe, V, Cr, and Ni;

A is an anion;

n is either 0, 1, or 2;

$X_1$, $X_2$, $X_3$ and $X_4$ are independently selected from the group consisting of hydrogen, silyls, aryls, arylalkyls, primary alkyls, secondary alkyls, tertiary alkyls, alkoxys, aryloxys, aminos, quaternary amines, heteroatoms, and hydrogen;

$Y_1$, $Y_2$, $Y_3$, $Y_4$, $Y_5$, and $Y_6$ are independently selected from the group consisting of hydrogen, halides, alkyls, aryls, arylalkyls, silyl groups, aminos, alkyls or aryls bearing heteroatoms, alkoxys, and halide; and $R_1$, $R_2$ $R_3$ and $R_4$ are independently selected from the group consisting of hydrogen, aryl, fatty acid esters, substituted alkoxyaryls, heteroatom-bearing aromatic groups, arylalkyls, primary alkyls, secondary alkyls, and tertiary alkyls.

12. The method in accordance with claim 11, wherein said salen-metal complex is topically applied to said skin prior to ultraviolet light exposure.

13. The method in accordance with claim 11, wherein said salen-metal complex is topically applied to said skin in conjunction with ultraviolet light exposure.

14. The method in accordance with claim 11, wherein said salen-metal complex is topically applied to said skin after ultraviolet light exposure.

15. A method for enhancing the recovery of skin of a mammal to a wound, said method comprising: applying to said skin an effective amount of a salen-metal complex of the formula:

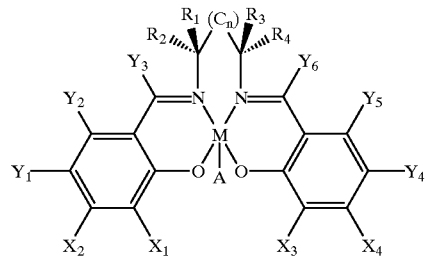

wherein:

M is selected from the group consisting of Mn, Co, Fe, V, Cr, and Ni;

A is an anion;

n is either 0, 1, or 2;

$X_1$, $X_2$, $X_3$ and $X_4$ are independently selected from the group consisting of hydrogen, silyls, aryls, arylalkyls, primary alkyls, secondary alkyls, tertiary alkyls, alkoxys, aryloxys, aminos, quaternary amines, heteroatoms, and hydrogen;

$Y_1$, $Y_2$, $Y_3$, $Y_4$, $Y_5$, and $Y_6$ are independently selected from the group consisting of hydrogen, halides, alkyls, aryls, arylalkyls, silyl groups, aminos, alkyls or aryls bearing heteroatoms, alkoxys, and halide; and $R_1$, $R_2$ $R_3$ and $R_4$ are independently selected from the group consisting of hydrogen, aryl, fatty acid esters, substituted alkoxyaryls, heteroatom-bearing aromatic groups, arylalkyls, primary alkyls, secondary alkyls, and tertiary alkyls.

16. The method in accordance with claim 15, wherein said wound is a member selected from the group consisting of surgical incisions, burns, inflammation and irritations due to oxidative damage.

17. A method for protecting cells from the deleterious effects of ionizing radiation, said method comprising: contacting said cells with an effective amount of a salen-metal complex of the formula:

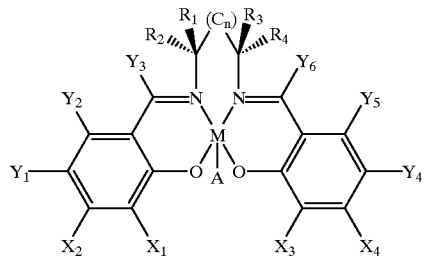

wherein:

M is selected from the group consisting of Mn, Co, Fe, V, Cr, and Ni;

A is an anion;

n is either 0, 1, or 2;

$X_1$, $X_2$, $X_3$ and $X_4$ are independently selected from the group consisting of hydrogen, silyls, aryls, arylalkyls, primary alkyls, secondary alkyls, tertiary alkyls, alkoxys, aryloxys, aminos, quaternary amines, heteroatoms, and hydrogen;

$Y_1$, $Y_2$, $Y_3$, $Y_4$, $Y_5$, and $Y_6$ are independently selected from the group consisting of hydrogen, halides, alkyls, aryls, arylalkyls, silyl groups, aminos, alkyls or aryls bearing heteroatoms, alkoxys, and halide; and $R_1$, $R_2$ $R_3$ and $R_4$ are independently selected from the group consisting of hydrogen, aryl, fatty acid esters, substituted alkoxyaryls, heteroatom-bearing aromatic groups, arylalkyls, primary alkyls, secondary alkyls, and tertiary alkyls.

18. The method in accordance with claim 17, wherein said ionizing radiation is ultraviolet radiation.

19. The method in accordance with claim 17, wherein said ionizing radiation is gamma(γ)-radiation.

20. The method in accordance with claim 17, wherein said cells are human cells.

21. The method in accordance with claim 17, wherein said contacting is carried out by administering to a human said salen-metal complex.

22. A method for protecting cells from the deleterious effects of a chemotherapeutic agent, said method comprising: contacting said cells with an effective amount of a salen-metal complex of the formula:

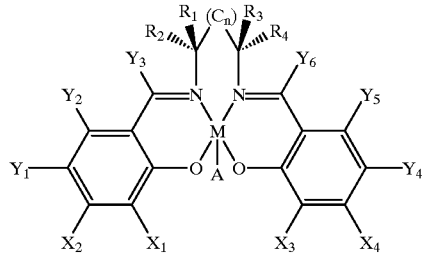

wherein:

M is selected from the group consisting of Mn, Co, Fe, V, Cr, and Ni;

A is an anion;

n is either 0, 1, or 2;

$X_1$, $X_2$, $X_3$ and $X_4$ are independently selected from the group consisting of hydrogen, silyls, aryls, arylalkyls, primary alkyls, secondary alkyls, tertiary alkyls, alkoxys, aryloxys, aminos, quaternary amines, heteroatoms, and hydrogen;

$Y_1$, $Y_2$, $Y_3$, $Y_4$, $Y_5$, and $Y_6$ are independently selected from the group consisting of hydrogen, halides, alkyls, aryls, arylalkyls, silyl groups, aminos, alkyls or aryls bearing heteroatoms, alkoxys, and halide; and $R_1$, $R_2$ $R_3$ and $R_4$ are independently selected from the group consisting of hydrogen, aryl, fatty acid esters, substituted alkoxyaryls, heteroatom-bearing aromatic groups, arylalkyls, primary alkyls, secondary alkyls, and tertiary alkyls.

23. The method in accordance with claim 22, wherein said cells are human cells.

24. A composition useful for topical application, said composition comprising a topical carrier and a salen-metal complex of the formula:

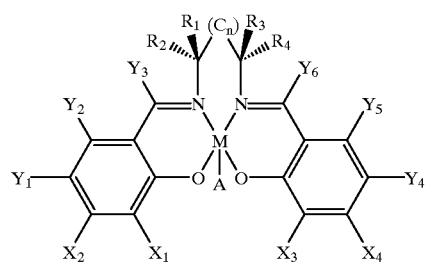

wherein:

M is selected from the group consisting of Mn, Co, Fe, V, Cr, and Ni;

A is an anion;

n is either 0, 1, or 2;

$X_1$, $X_2$, $X_3$ and $X_4$ are independently selected from the group consisting of hydrogen, silyls, aryls, arylalkyls, primary alkyls, secondary alkyls, tertiary alkyls, alkoxys, aryloxys, aminos, quaternary amines, heteroatoms, and hydrogen;

$Y_1$, $Y_2$, $Y_3$, $Y_4$, $Y_5$, and $Y_6$ are independently selected from the group consisting of hydrogen, halides, alkyls, aryls, arylalkyls, silyl groups, aminos, alkyls or aryls bearing heteroatoms, alkoxys, and halide; and $R_1$, $R_2$ $R_3$ and $R_4$ are independently selected from the group consisting of hydrogen, aryl, fatty acid esters, substituted alkoxyaryls, heteroatom-bearing aromatic groups, arylalkyls, primary alkyls, secondary alkyls, and tertiary alkyls.

* * * * *